US010494645B2

(12) United States Patent
Auricchio et al.

(10) Patent No.: US 10,494,645 B2

(45) Date of Patent: Dec. 3, 2019

(54) EFFECTIVE DELIVERY OF LARGE GENES BY DUAL AAV VECTORS

(71) Applicant: Fondazione Telethon, Rome (IT)

(72) Inventors: Alberto Auricchio, Naples (IT); Pasqualina Colella, Naples (IT); Ivana Trapani, Naples (IT)

(73) Assignee: FONDAZIONE TELETHON, Rome (IT)

( * ) Notice: Subject to any disclaimer, the term of this patent is extended or adjusted under 35 U.S.C. 154(b) by 0 days.

(21) Appl. No.: 14/785,229

(22) PCT Filed: Apr. 18, 2014

(86) PCT No.: PCT/EP2014/058000

§ 371 (c)(1),
(2) Date: Oct. 16, 2015

(87) PCT Pub. No.: WO2014/170480

PCT Pub. Date: Oct. 23, 2014

(65) Prior Publication Data

US 2016/0076054 A1 Mar. 17, 2016

Related U.S. Application Data

(60) Provisional application No. 61/813,342, filed on Apr. 18, 2013.

(51) Int. Cl.

| | |
|---|---|
| ***A61K 48/00*** | (2006.01) |
| ***C07H 21/04*** | (2006.01) |
| ***C12N 15/63*** | (2006.01) |
| ***C12N 15/00*** | (2006.01) |
| ***C12N 15/86*** | (2006.01) |
| ***C07K 14/705*** | (2006.01) |
| *A01K 67/00* | (2006.01) |

(52) U.S. Cl.

CPC ............ *C12N 15/86* (2013.01); *A61K 48/005* (2013.01); *C07K 14/705* (2013.01); *C12N 2750/14143* (2013.01); *C12N 2800/40* (2013.01); *C12N 2840/20* (2013.01); *C12N 2840/44* (2013.01); *C12N 2840/445* (2013.01)

(58) Field of Classification Search

CPC .......... C12N 15/86; C12N 2750/14143; C12N 2800/40; C12N 2840/20; C12N 2840/445; C12N 2840/44; A61K 48/005

See application file for complete search history.

(56) References Cited

U.S. PATENT DOCUMENTS

| | | | | |
|---|---|---|---|---|
| 6,255,071 | B1 * | 7/2001 | Beach | C07K 14/005 435/320.1 |
| 6,808,922 | B1 * | 10/2004 | Bebbington | C12N 15/63 424/93.1 |
| 6,846,970 | B1 * | 1/2005 | Christou | C12N 15/8201 435/470 |
| 7,250,406 | B2 * | 7/2007 | Tang | C07K 14/62 435/455 |
| 2010/0003218 | A1 | 1/2010 | Duan et al. | |
| 2010/0209414 | A1 | 8/2010 | Schmidt et al. | |
| 2014/0256802 | A1 * | 9/2014 | Boye | C07K 14/47 514/44 R |

FOREIGN PATENT DOCUMENTS

| | | |
|---|---|---|
| WO | 2008106644 | 9/2008 |
| WO | 2009103562 | 8/2009 |
| WO | 2013075008 | 5/2013 |

OTHER PUBLICATIONS

Lopes et al., "Retinal gene therapy with a large MY07A cDNA using adeno-associated virus", Gene Therapy, vol. 20, No. 8, Jan. 24, 2013, pp. 824-833.

Trapan et al., "Effective delivery of large genes to the retina by dual AAV vectors", EMBO Molecular Medicine, vol. 6, No. 2, Dec. 2013, pp. 194-211.

McClements et al., "Gene therapy for retinal disease", Transitional Research, vol. 161, No. 4, Apr. 2013, pp. 241-254.

International Search Report based on International Application PCT/EP2014/058000.

* cited by examiner

*Primary Examiner* — Quang Nguyen

(74) *Attorney, Agent, or Firm* — Lucas & Mercanti, LLP

(57) ABSTRACT

The present invention relates to constructs, vectors, relative host cells and pharmaceutical compositions which allow an effective gene therapy, in particular of genes larger than 5 Kb.

19 Claims, 15 Drawing Sheets

Figure 1:
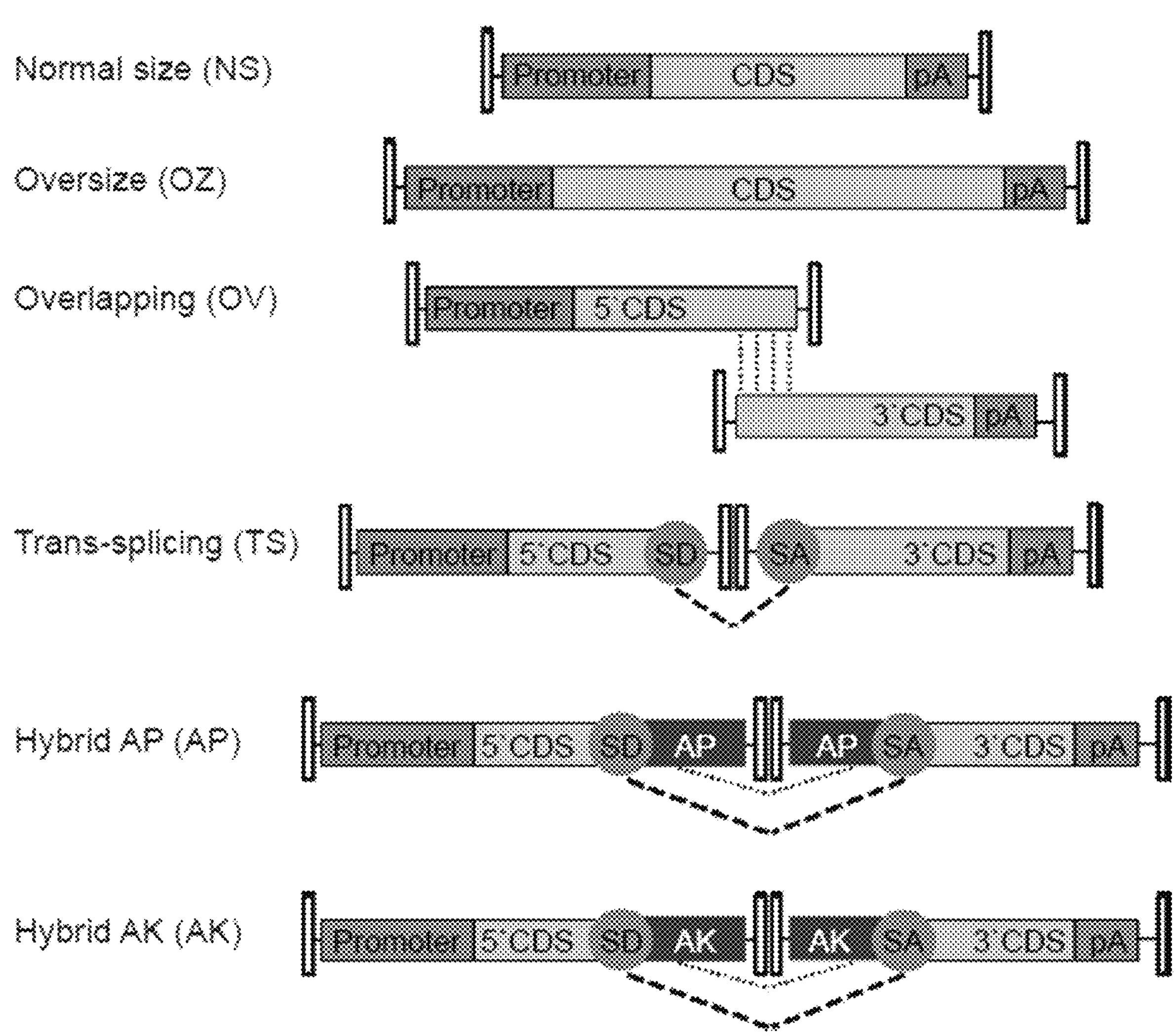

Specification includes a Sequence Listing.

A

B a

RHO-*ABCA4* b

CBA-*MYO7A* a dual AAV hybrid AK vectors with heterologous ITRs (5:2 + 2:5)

b

```
SEQUENCE LISTING

<160> NUMBER OF SEQ ID NOS: 31

<210> SEQ ID NO 1
<211> LENGTH: 82
<212> TYPE: DNA
<213> ORGANISM: Artificial Sequence
<220> FEATURE:
<223> OTHER INFORMATION: synthetic

<400> SEQUENCE: 1

gtaagtatca aggttacaag acaggtttaa ggagaccaat agaaactggg cttgtcgaga      60

cagagaagac tcttgcgttt ct                                               82


<210> SEQ ID NO 2
<211> LENGTH: 51
<212> TYPE: DNA
<213> ORGANISM: Artificial Sequence
<220> FEATURE:
<223> OTHER INFORMATION: synthetic

<400> SEQUENCE: 2

gataggcacc tattggtctt actgacatcc actttgcctt tctctccaca g               51


<210> SEQ ID NO 3
<211> LENGTH: 77
<212> TYPE: DNA
<213> ORGANISM: Artificial Sequence
<220> FEATURE:
<223> OTHER INFORMATION: synthetic

<400> SEQUENCE: 3

gggattttgc cgatttcggc ctattggtta aaaaatgagc tgatttaaca aaaatttaac      60

gcgaatttta acaaaat                                                     77


<210> SEQ ID NO 4
<211> LENGTH: 130
<212> TYPE: DNA
<213> ORGANISM: Artificial Sequence
<220> FEATURE:
```

<223> OTHER INFORMATION: synthetic

<400> SEQUENCE: 4
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct 130

<210> SEQ ID NO 5
<211> LENGTH: 175
<212> TYPE: DNA
<213> ORGANISM: Artificial Sequence
<220> FEATURE:
<223> OTHER INFORMATION: synthetic

<400> SEQUENCE: 5
ctctcccccc tgtcgcgttc gctcgctcgc tggctcgttt ggggggggtgg cagctcaaag 60 agctgccaga cgacggccct ctggccgtcg cccccccaaa cgagccagcg agcgagcgaa 120
cgcgacaggg gggagagtgc cacactctca agcaaggggg ttttgtaagc agtga 175

<210> SEQ ID NO 6
<211> LENGTH: 153
<212> TYPE: DNA
<213> ORGANISM: Artificial Sequence
<220> FEATURE:
<223> OTHER INFORMATION: synthetic

<400> SEQUENCE: 6
tcaatattgg ccattagcca tattattcat tggttatata gcataaatca atattggcta 60
ttggccattg catacgttgt atctatatca taatatgtac atttatattg gctcatgtcc 120
aatatgaccg ccatgttggc attgattatt gac 153

<210> SEQ ID NO 7
<211> LENGTH: 583
<212> TYPE: DNA
<213> ORGANISM: Artificial Sequence
<220> FEATURE:
<223> OTHER INFORMATION: synthetic

<400> SEQUENCE: 7
tagttattaa tagtaatcaa ttacggggtc attagttcat agcccatata tggagttccg 60
cgttacataa cttacggtaa atggcccgcc tggctgaccg cccaacgacc cccgcccatt 120
gacgtcaata atgacgtatg ttcccatagt aacgccaata gggactttcc attgacgtca 180
atgggtggag tatttacggt aaactgccca cttggcagta catcaagtgt atcatatgcc 240
aagtccgccc cctattgacg tcaatgacgg taaatggccc gcctggcatt atgcccagta 300
catgacctta cgggactttc ctacttggca gtacatctac gtattagtca tcgctattac 360
catggtgatg cggttttggc agtacaccaa tgggcgtgga tagcggtttg actcacgggg 420
atttccaagt ctccacccca ttgacgtcaa tgggagtttg ttttggcacc aaaatcaacg 480
ggactttcca aaatgtcgta ataaccccgc cccgttgacg caaatgggcg gtaggcgtgt 540
acggtgggag gtctatataa gcagagctcg tttagtgaac cgt 583

<210> SEQ ID NO 8
<211> LENGTH: 133
<212> TYPE: DNA
<213> ORGANISM: Artificial Sequence
<220> FEATURE:
<223> OTHER INFORMATION: synthetic

<400> SEQUENCE: 8

```
gtaagtatca aggttacaag acaggtttaa ggagaccaat agaaactggg cttgtcgaga     60

cagagaagac tcttgcgttt ctgataggca cctattggtc ttactgacat ccactttgcc    120

tttctctcca cag                                                       133
```

<210> SEQ ID NO 9
<211> LENGTH: 2918
<212> TYPE: DNA
<213> ORGANISM: Artificial Sequence
<220> FEATURE:
<223> OTHER INFORMATION: synthetic

<400> SEQUENCE: 9

```
atgggcttcg tgagacagat acagcttttg ctctggaaga actggaccct gcggaaaagg     60

caaaagattc gctttgtggt ggaactcgtg tggcctttat ctttatttct ggtcttgatc    120

tggttaagga atgccaaccc gctctacagc catcatgaat gccatttccc caacaaggcg    180

atgccctcag caggaatgct gccgtggctc caggggatct tctgcaatgt gaacaatccc    240

tgttttcaaa gccccacccc aggagaatct cctggaattg tgtcaaacta taacaactcc    300

atcttggcaa gggtatatcg agattttcaa gaactcctca tgaatgcacc agagagccag    360

caccttggcc gtatttggac agagctacac atcttgtccc aattcatgga caccctccgg    420

actcacccgg agagaattgc aggaagagga attcgaataa gggatatctt gaaagatgaa    480

gaaacactga cactatttct cattaaaaac atcggcctgt ctgactcagt ggtctacctt    540

ctgatcaact ctcaagtccg tccagagcag ttcgctcatg gagtcccgga cctggcgctg    600

aaggacatcg cctgcagcga ggccctcctg gagcgcttca tcatcttcag ccagagacgc    660

ggggcaaaga cggtgcgcta tgccctgtgc tccctctccc agggcaccct acagtggata    720

gaagacactc tgtatgccaa cgtggacttc ttcaagctct tccgtgtgct tcccacactc    780

ctagacagcc gttctcaagg tatcaatctg agatcttggg gaggaatatt atctgatatg    840

tcaccaagaa ttcaagagtt tatccatcgg ccgagtatgc aggacttgct gtgggtgacc    900

aggcccctca tgcagaatgg tggtccagag acctttacaa agctgatggg catcctgtct    960

gacctcctgt gtggctaccc cgagggaggt ggctctcggg tgctctcctt caactggtat   1020

gaagacaata actataaggc ctttctgggg attgactcca caaggaagga tcctatctat   1080

tcttatgaca gaagaacaac atccttttgt aatgcattga tccagagcct ggagtcaaat   1140

cctttaacca aaatcgcttg gagggcggca aagcctttgc tgatgggaaa aatcctgtac   1200

actcctgatt cacctgcagc acgaaggata ctgaagaatg ccaactcaac ttttgaagaa   1260

ctggaacacg ttaggaagtt ggtcaaagcc tgggaagaag tagggcccca gatctggtac   1320

ttctttgaca acagcacaca gatgaacatg atcagagata ccctggggaa cccaacagta   1380

aaagactttt tgaataggca gcttggtgaa gaaggtatta ctgctgaagc catcctaaac   1440

ttcctctaca agggccctcg ggaaagccag gctgacgaca tggccaactt cgactggagg   1500

gacatattta acatcactga tcgcaccctc cgccttgtca atcaatacct ggagtgcttg   1560

gtcctggata agtttgaaag ctacaatgat gaaactcagc tcacccaacg tgccctctct   1620

ctactggagg aaaacatgtt ctgggccgga gtggtattcc ctgacatgta tccctggacc   1680

agctctctac caccccacgt gaagtataag atccgaatgg acatagacgt ggtggagaaa   1740

accaataaga ttaaagacag gtattgggat tctggtccca gagctgatcc cgtggaagat   1800
```

```
ttccggtaca tctggggcgg gtttgcctat ctgcaggaca tggttgaaca ggggatcaca   1860

aggagccagg tgcaggcgga ggctccagtt ggaatctacc tccagcagat gccctacccc   1920

tgcttcgtgg acgattcttt catgatcatc ctgaaccgct gtttccctat cttcatggtg   1980

ctggcatgga tctactctgt ctccatgact gtgaagagca tcgtcttgga gaaggagttg   2040

cgactgaagg agaccttgaa aaatcagggt gtctccaatg cagtgatttg gtgtacctgg   2100

ttcctggaca gcttctccat catgtcgatg agcatcttcc tcctgacgat attcatcatg   2160

catggaagaa tcctacatta cagcgaccca ttcatcctct tcctgttctt gttggctttc   2220

tccactgcca ccatcatgct gtgctttctg ctcagcacct tcttctccaa ggccagtctg   2280

gcagcagcct gtagtggtgt catctatttc accctctacc tgccacacat cctgtgcttc   2340

gcctggcagg accgcatgac cgctgagctg aagaaggctg tgagcttact gtctccggtg   2400

gcatttggat ttggcactga gtacctggtt cgctttgaag agcaaggcct ggggctgcag   2460

tggagcaaca tcgggaacag tcccacggaa ggggacgaat tcagcttcct gctgtccatg   2520

cagatgatgc tccttgatgc tgctgtctat ggcttactcg cttggtacct tgatcaggtg   2580

tttccaggag actatggaac cccacttcct tggtactttc ttctacaaga gtcgtattgg   2640

cttggcggtg aagggtgttc aaccagagaa gaaagagccc tggaaaagac cgagccccta   2700

acagaggaaa cggaggatcc agagcaccca gaaggaatac acgactcctt ctttgaacgt   2760

gagcatccag ggtgggttcc tggggtatgc gtgaagaatc tggtaaagat tttgagccc    2820

tgtggccggc cagctgtgga ccgtctgaac atcaccttct acgagaacca gatcaccgca   2880

ttcctgggcc acaatggagc tgggaaaacc accacctt                           2918
```

<210> SEQ ID NO 10
<211> LENGTH: 130
<212> TYPE: DNA
<213> ORGANISM: Artificial Sequence
<220> FEATURE:
<223> OTHER INFORMATION: synthetic

<400> SEQUENCE: 10

```
aggaacccct agtgatggag ttggccactc cctctctgcg cgctcgctcg ctcactgagg     60

ccgggcgacc aaaggtcgcc cgacgcccgg gctttgcccg ggcggcctca gtgagcgagc    120

gagcgcgcag                                                          130
```

<210> SEQ ID NO 11
<211> LENGTH: 4540
<212> TYPE: DNA
<213> ORGANISM: Artificial Sequence
<220> FEATURE:
<223> OTHER INFORMATION: synthetic

<400> SEQUENCE: 11

```
ctgcgcgctc gctcgctcac tgaggccgcc cgggcaaagc ccgggcgtcg ggcgaccttt     60

ggtcgcccgg cctcagtgag cgagcgagcg cgcagagagg gagtggccaa ctccatcact    120

aggggttcct tgtagttaat gattaacccg ccatgctact tatctacgta gccatgctct    180

aggaagatct tcaatattgg ccattagcca tattattcat tggttatata gcataaatca    240

atattggcta ttggccattg catacgttgt atctatatca taatatgtac atttatattg    300

gctcatgtcc aatatgaccg ccatgttggc attgattatt gactagttat taatagtaat    360

caattacggg gtcattagtt catagcccat atatggagtt ccgcgttaca taacttacgg    420

taaatggccc gcctggctga ccgcccaacg acccccgccc attgacgtca ataatgacgt    480
```

```
atgttcccat agtaacgcca atagggactt tccattgacg tcaatgggtg gagtatttac    540
ggtaaactgc ccacttggca gtacatcaag tgtatcatat gccaagtccg ccccctattg    600
acgtcaatga cggtaaatgg cccgcctggc attatgccca gtacatgacc ttacgggact    660
ttcctacttg gcagtacatc tacgtattag tcatcgctat taccatggtg atgcggtttt    720
ggcagtacac caatgggcgt ggatagcggt ttgactcacg gggatttcca agtctccacc    780
ccattgacgt caatgggagt ttgttttggc accaaaatca acgggacttt ccaaaatgtc    840
gtaataaccc cgccccgttg acgcaaatgg gcggtaggcg tgtacggtgg gaggtctata    900
taagcagagc tcgtttagtg aaccgtcaga tcactagaag ctttattgcg gtagtttatc    960
acagttaaat tgctaacgca gtcagtgctt ctgacacaac agtctcgaac ttaagctgca   1020
gaagttggtc gtgaggcact gggcaggtaa gtatcaaggt tacaagacag gtttaaggag   1080
accaatagaa actgggcttg tcgagacaga gaagactctt gcgtttctga taggcaccta   1140
ttggtcttac tgacatccac tttgcctttc tctccacagg tgtccactcc cagttcaatt   1200
acagctctta aggctagagt acttaatacg actcactata ggctagcctc gagaattcac   1260
gcgtggtacc tctagagtcg acccgggcgg ccgccatggg cttcgtgaga cagatacagc   1320
ttttgctctg gaagaactgg accctgcgga aaaggcaaaa gattcgcttt gtggtggaac   1380
tcgtgtggcc tttatcttta tttctggtct tgatctggtt aaggaatgcc aacccgctct   1440
acagccatca tgaatgccat ttccccaaca aggcgatgcc ctcagcagga atgctgccgt   1500
ggctccaggg gatcttctgc aatgtgaaca atccctgttt tcaaagcccc accccaggag   1560
aatctcctgg aattgtgtca aactataaca actccatctt ggcaagggta tatcgagatt   1620
ttcaagaact cctcatgaat gcaccagaga gccagcacct tggccgtatt tggacagagc   1680
tacacatctt gtcccaattc atggacaccc tccggactca cccggagaga attgcaggaa   1740
gaggaattcg aataagggat atcttgaaag atgaagaaac actgacacta tttctcatta   1800
aaaacatcgg cctgtctgac tcagtggtct accttctgat caactctcaa gtccgtccag   1860
agcagttcgc tcatggagtc ccggacctgg cgctgaagga catcgcctgc agcgaggccc   1920
tcctggagcg cttcatcatc ttcagccaga gacgcggggc aaagacggtg cgctatgccc   1980
tgtgctccct ctcccagggc accctacagt ggatagaaga cactctgtat gccaacgtgg   2040
acttcttcaa gctcttccgt gtgcttccca cactcctaga cagccgttct caaggtatca   2100
atctgagatc ttggggagga atattatctg atatgtcacc aagaattcaa gagtttatcc   2160
atcggccgag tatgcaggac ttgctgtggg tgaccaggcc cctcatgcag aatggtggtc   2220
cagagacctt tacaaagctg atgggcatcc tgtctgacct cctgtgtggc taccccgagg   2280
gaggtggctc tcgggtgctc tccttcaact ggtatgaaga caataactat aaggcctttc   2340
tggggattga ctccacaagg aaggatccta tctattctta tgacagaaga acaacatcct   2400
tttgtaatgc attgatccag agcctggagt caaatccttt aaccaaaatc gcttggaggg   2460
cggcaaagcc tttgctgatg ggaaaaatcc tgtacactcc tgattcacct gcagcacgaa   2520
ggatactgaa gaatgccaac tcaacttttg aagaactgga acacgttagg aagttggtca   2580
aagcctggga agaagtaggg ccccagatct ggtacttctt tgacaacagc acacagatga   2640
acatgatcag agataccctg ggaacccaa cagtaaaaga ctttttgaat aggcagcttg    2700
gtgaagaagg tattactgct gaagccatcc taaacttcct ctacaagggc cctcgggaaa   2760
gccaggctga cgacatggcc aacttcgact ggagggacat atttaacatc actgatcgca   2820
```

```
ccctccgcct tgtcaatcaa tacctggagt gcttggtcct ggataagttt gaaagctaca   2880

atgatgaaac tcagctcacc caacgtgccc tctctctact ggaggaaaac atgttctggg   2940

ccggagtggt attccctgac atgtatccct ggaccagctc tctaccaccc cacgtgaagt   3000

ataagatccg aatggacata gacgtggtgg agaaaaccaa taagattaaa gacaggtatt   3060

gggattctgg tcccagagct gatcccgtgg aagatttccg gtacatctgg ggcgggtttg   3120

cctatctgca ggacatggtt gaacagggga tcacaaggag ccaggtgcag gcggaggctc   3180

cagttggaat ctacctccag cagatgccct acccctgctt cgtggacgat tctttcatga   3240

tcatcctgaa ccgctgtttc cctatcttca tggtgctggc atggatctac tctgtctcca   3300

tgactgtgaa gagcatcgtc ttggagaagg agttgcgact gaaggagacc ttgaaaaatc   3360

agggtgtctc caatgcagtg atttggtgta cctggttcct ggacagcttc tccatcatgt   3420

cgatgagcat cttcctcctg acgatattca tcatgcatgg aagaatccta cattacagcg   3480

acccattcat cctcttcctg ttcttgttgg ctttctccac tgccaccatc atgctgtgct   3540

ttctgctcag caccttcttc tccaaggcca gtctggcagc agcctgtagt ggtgtcatct   3600

atttcaccct ctacctgcca cacatcctgt gcttcgcctg gcaggaccgc atgaccgctg   3660

agctgaagaa ggctgtgagc ttactgtctc cggtggcatt tggatttggc actgagtacc   3720

tggttcgctt tgaagagcaa ggcctggggc tgcagtggag caacatcggg aacagtccca   3780

cggaagggga cgaattcagc ttcctgctgt ccatgcagat gatgctcctt gatgctgctg   3840

tctatggctt actcgcttgg taccttgatc aggtgtttcc aggagactat ggaaccccac   3900

ttccttggta ctttcttcta caagagtcgt attggcttgg cggtgaaggg tgttcaacca   3960

gagaagaaag agccctggaa aagaccgagc ccctaacaga ggaaacggag gatccagagc   4020

acccagaagg aatacacgac tccttctttg aacgtgagca tccagggtgg gttcctgggg   4080

tatgcgtgaa gaatctggta aagatttttg agccctgtgg ccggccagct gtggaccgtc   4140

tgaacatcac cttctacgag aaccagatca ccgcattcct gggccacaat ggagctggga   4200

aaaccaccac cttgtaagta tcaaggttac aagacaggtt taaggagacc aatagaaact   4260

gggcttgtcg agacagagaa gactcttgcg tttctgggat tttgccgatt tcggcctatt   4320

ggttaaaaaa tgagctgatt taacaaaaat ttaacgcgaa ttttaacaaa atattaacgt   4380

ttataatttc aggtggcatc tttccaattg aggaacccct agtgatggag ttggccactc   4440

cctctctgcg cgctcgctcg ctcactgagg ccgggcgacc aaaggtcgcc cgacgcccgg   4500

gctttgcccg ggcggcctca gtgagcgagc gagcgcgcag                         4540
```

<210> SEQ ID NO 12
<211> LENGTH: 3978
<212> TYPE: DNA
<213> ORGANISM: Artificial Sequence
<220> FEATURE:
<223> OTHER INFORMATION: synthetic

<400> SEQUENCE: 12

```
gtccatcctg acgggtctgt tgccaccaac ctctgggact gtgctcgttg ggggaaggga     60

cattgaaacc agcctggatg cagtccggca gagccttggc atgtgtccac agcacaacat    120

cctgttccac cacctcacgg tggctgagca catgctgttc tatgcccagc tgaaaggaaa    180

gtcccaggag gaggcccagc tggagatgga agccatgttg gaggacacag gcctccacca    240

caagcggaat gaagaggctc aggacctatc aggtggcatg cagagaaagc tgtcggttgc    300

cattgccttt gtgggagatg ccaaggtggt gattctggac gaacccacct ctggggtgga    360
```

```
cccttactcg agacgctcaa tctgggatct gctcctgaag tatcgctcag gcagaaccat    420
catcatgtcc actcaccaca tggacgaggc cgacctcctt ggggaccgca ttgccatcat    480
tgcccaggga aggctctact gctcaggcac ccccactcttc ctgaagaact gctttggcac    540
aggcttgtac ttaaccttgg tgcgcaagat gaaaaacatc cagagccaaa ggaaaggcag    600
tgaggggacc tgcagctgct cgtctaaggg tttctccacc acgtgtccag cccacgtcga    660
tgacctaact ccagaacaag tcctggatgg ggatgtaaat gagctgatgg atgtagttct    720
ccaccatgtt ccagaggcaa agctggtgga gtgcattggt caagaactta tcttccttct    780
tccaaataag aacttcaagc acagagcata tgccagcctt ttcagagagc tggaggagac    840
gctggctgac cttggtctca gcagttttgg aatttctgac actcccctgg aagagatttt    900
tctgaaggtc acggaggatt ctgattcagg acctctgttt gcgggtggcg ctcagcagaa    960
aagagaaaac gtcaaccccc gacacccctg cttgggtccc agagagaagg ctggacagac   1020
accccaggac tccaatgtct gctccccagg ggcgccggct gctcacccag agggccagcc   1080
tcccccagag ccagagtgcc caggcccgca gctcaacacg gggacacagc tggtcctcca   1140
gcatgtgcag gcgctgctgg tcaagagatt ccaacacacc atccgcagcc acaaggactt   1200
cctggcgcag atcgtgctcc cggctacctt tgtgtttttg gctctgatgc tttctattgt   1260
tatccctcct tttggcgaat accccgcttt gacccttcac ccctggatat atgggcagca   1320
gtacaccttc ttcagcatgg atgaaccagg cagtgagcag ttcacggtac ttgcagacgt   1380
cctcctgaat aagccaggct ttggcaaccg ctgcctgaag gaagggtggc ttccggagta   1440
cccctgtggc aactcaacac cctggaagac tccttctgtg tccccaaaca tcacccagct   1500
gttccagaag cagaaatgga cacaggtcaa cccttcacca tcctgcaggt gcagcaccag   1560
ggagaagctc accatgctgc cagagtgccc cgagggtgcc gggggcctcc cgccccccca   1620
gagaacacag cgcagcacgg aaattctaca agacctgacg gacaggaaca tctccgactt   1680
cttggtaaaa acgtatcctg ctcttataag aagcagctta aagagcaaat tctgggtcaa   1740
tgaacagagg tatggaggaa tttccattgg aggaaagctc ccagtcgtcc ccatcacggg   1800
ggaagcactt gttgggtttt taagcgacct tggccggatc atgaatgtga gcgggggccc   1860
tatcactaga gaggcctcta aagaaatacc tgatttcctt aaacatctag aaactgaaga   1920
caacattaag gtgtggttta ataacaaagg ctggcatgcc ctggtcagct ttctcaatgt   1980
ggcccacaac gccatcttac gggccagcct gcctaaggac agaagccccg aggagtatgg   2040
aatcaccgtc attagccaac ccctgaacct gaccaaggag cagctctcag agattacagt   2100
gctgaccact tcagtggatg ctgtggttgc catctgcgtg attttctcca tgtccttcgt   2160
cccagccagc tttgtccttt atttgatcca ggagcgggtg aacaaatcca agcacctcca   2220
gtttatcagt ggagtgagcc ccaccaccta ctgggtaacc aacttcctct gggacatcat   2280
gaattattcc gtgagtgctg ggctggtggt gggcatcttc atcgggtttc agaagaaagc   2340
ctacacttct ccagaaaacc ttcctgccct tgtggcactg ctcctgctgt atggatgggc   2400
ggtcattccc atgatgtacc cagcatcctt cctgtttgat gtccccagca cagcctatgt   2460
ggctttatct tgtgctaatc tgttcatcgg catcaacagc agtgctatta ccttcatctt   2520
ggaattattt gagaataacc ggacgctgct caggttcaac gccgtgctga ggaagctgct   2580
cattgtcttc cccccacttct gcctgggccg gggcctcatt gaccttgcac tgagccaggc   2640
tgtgacagat gtctatgccc ggtttggtga ggagcactct gcaaatccgt tccactggga   2700
```

```
cctgattggg aagaacctgt ttgccatggt ggtggaaggg gtggtgtact tcctcctgac   2760

cctgctggtc cagcgccact tcttcctctc ccaatggatt gccgagccca ctaaggagcc   2820

cattgttgat gaagatgatg atgtggctga agaaagacaa agaattatta ctggtggaaa   2880

taaaactgac atcttaaggc tacatgaact aaccaagatt tatccaggca cctccagccc   2940

agcagtggac aggctgtgtg tcggagttcg ccctggagag tgctttggcc tcctgggagt   3000

gaatggtgcc ggcaaaacaa ccacattcaa gatgctcact ggggacacca cagtgacctc   3060

aggggatgcc accgtagcag gcaagagtat tttaaccaat atttctgaag tccatcaaaa   3120

tatgggctac tgtcctcagt ttgatgcaat cgatgagctg ctcacaggac gagaacatct   3180

ttacctttat gcccggcttc gaggtgtacc agcagaagaa atcgaaaagg ttgcaaactg   3240

gagtattaag agcctgggcc tgactgtcta cgccgactgc ctggctggca cgtacagtgg   3300

gggcaacaag cggaaactct ccacagccat cgcactcatt ggctgcccac cgctggtgct   3360

gctggatgag cccaccacag ggatggaccc ccaggcacgc cgcatgctgt ggaacgtcat   3420

cgtgagcatc atcagagaag ggagggctgt ggtcctcaca tcccacagca tggaagaatg   3480

tgaggcactg tgtacccggc tggccatcat ggtaaagggc gcctttcgat gtatgggcac   3540

cattcagcat ctcaagtcca aatttggaga tggctatatc gtcacaatga agatcaaatc   3600

cccgaaggac gacctgcttc ctgacctgaa ccctgtggag cagttcttcc aggggaactt   3660

cccaggcagt gtgcagaggg agaggcacta caacatgctc cagttccagg tctcctcctc   3720

ctccctggcg aggatcttcc agctcctcct ctcccacaag gacagcctgc tcatcgagga   3780

gtactcagtc acacagacca cactggacca ggtgtttgta aattttgcta aacagcagac   3840

tgaaagtcat gacctccctc tgcaccctcg agctgctgga gccagtcgac aagcccagga   3900

cgactacaaa gaccatgacg gtgattataa agatcatgac atcgactaca aggatgacga   3960

tgacaagtga gcggccgc                                                 3978
```

<210> SEQ ID NO 13
<211> LENGTH: 261
<212> TYPE: DNA
<213> ORGANISM: Artificial Sequence
<220> FEATURE:
<223> OTHER INFORMATION: synthetic

<400> SEQUENCE: 13

```
ttcgagcaga catgataaga tacattgatg agtttggaca aaccacaact agaatgcagt     60

gaaaaaaatg ctttatttgt gaaatttgtg atgctattgc tttatttgta accattataa    120

gctgcaataa acaagttaac aacaacaatt gcattcattt tatgtttcag gttcaggggg    180

agatgtggga ggttttttaa agcaagtaaa acctctacaa atgtggtaaa atcgataagg    240

atcttcctag agcatggcta c                                              261
```

<210> SEQ ID NO 14
<211> LENGTH: 175
<212> TYPE: DNA
<213> ORGANISM: Artificial Sequence
<220> FEATURE:
<223> OTHER INFORMATION: synthetic

<400> SEQUENCE: 14

```
tcactgctta caaaaccccc ttgcttgaga gtgtggcact ctccccccctg tcgcgttcgc     60

tcgctcgctg gctcgtttgg gggggcgacg gccagagggc cgtcgtctgg cagctctttg    120

agctgccacc cccccaaacg agccagcgag cgagcgaacg cgacaggggg gagag          175
```

<210> SEQ ID NO 15
<211> LENGTH: 4636
<212> TYPE: DNA
<213> ORGANISM: Artificial Sequence
<220> FEATURE:
<223> OTHER INFORMATION: synthetic

<400> SEQUENCE: 15

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct ggatccggga ttttgccgat ttcggcctat tggttaaaaa atgagctgat    180
ttaacaaaaa tttaacgcga attttaacaa aatattaacg tttataattt caggtggcat    240
ctttcgatag gcacctattg gtcttactga catccacttt gcctttctct ccacaggtcc    300
atcctgacgg gtctgttgcc accaacctct gggactgtgc tcgttggggg aagggacatt    360
gaaaccagcc tggatgcagt ccggcagagc cttggcatgt gtccacagca caacatcctg    420
ttccaccacc tcacggtggc tgagcacatg ctgttctatg cccagctgaa aggaaagtcc    480
caggaggagg cccagctgga gatggaagcc atgttggagg acacaggcct ccaccacaag    540
cggaatgaag aggctcagga cctatcaggt ggcatgcaga gaaagctgtc ggttgccatt    600
gcctttgtgg gagatgccaa ggtggtgatt ctggacgaac ccacctctgg ggtggaccct    660
tactcgagac gctcaatctg ggatctgctc ctgaagtatc gctcaggcag aaccatcatc    720
atgtccactc accacatgga cgaggccgac ctccttgggg accgcattgc catcattgcc    780
cagggaaggc tctactgctc aggcacccca ctcttcctga agaactgctt tggcacaggc    840
ttgtacttaa ccttggtgcg caagatgaaa aacatccaga gccaaaggaa aggcagtgag    900
gggacctgca gctgctcgtc taagggtttc tccaccacgt gtccagccca cgtcgatgac    960
ctaactccag aacaagtcct ggatggggat gtaaatgagc tgatggatgt agttctccac   1020
catgttccag aggcaaagct ggtggagtgc attggtcaag aacttatctt ccttcttcca   1080
aataagaact tcaagcacag agcatatgcc agccttttca gagagctgga ggagacgctg   1140
gctgaccttg gtctcagcag ttttggaatt tctgacactc ccctggaaga gatttttctg   1200
aaggtcacgg aggattctga ttcaggacct ctgtttgcgg gtggcgctca gcagaaaaga   1260
gaaaacgtca acccccgaca cccctgcttg ggtcccagag agaaggctgg acagacaccc   1320
caggactcca atgtctgctc cccaggggcg ccggctgctc acccagaggg ccagcctccc   1380
ccagagccag agtgcccagg cccgcagctc aacacgggga cacagctggt cctccagcat   1440
gtgcaggcgc tgctggtcaa gagattccaa cacaccatcc gcagccacaa ggacttcctg   1500
gcgcagatcg tgctcccggc tacctttgtg tttttggctc tgatgctttc tattgttatc   1560
cctccttttg gcgaataccc cgctttgacc cttcacccct ggatatatgg gcagcagtac   1620
accttcttca gcatggatga accaggcagt gagcagttca cggtacttgc agacgtcctc   1680
ctgaataagc caggctttgg caaccgctgc ctgaaggaag ggtggcttcc ggagtacccc   1740
tgtggcaact caacaccctg gaagactcct tctgtgtccc caaacatcac ccagctgttc   1800
cagaagcaga aatggacaca ggtcaaccct tcaccatcct gcaggtgcag caccagggag   1860
aagctcacca tgctgccaga gtgccccgag ggtgccgggg gcctcccgcc cccccagaga   1920
acacagcgca gcacggaaat tctacaagac ctgacggaca ggaacatctc cgacttcttg   1980
gtaaaaacgt atcctgctct tataagaagc agcttaaaga gcaaattctg ggtcaatgaa   2040
```

```
cagaggtatg gaggaatttc cattggagga aagctcccag tcgtccccat cacgggggaa   2100
gcacttgttg ggtttttaag cgaccttggc cggatcatga atgtgagcgg gggccctatc   2160
actagagagg cctctaaaga aatacctgat ttccttaaac atctagaaac tgaagacaac   2220
attaaggtgt ggtttaataa caaaggctgg catgccctgg tcagctttct caatgtggcc   2280
cacaacgcca tcttacgggc cagcctgcct aaggacagaa gccccgagga gtatggaatc   2340
accgtcatta gccaacccct gaacctgacc aaggagcagc tctcagagat tacagtgctg   2400
accacttcag tggatgctgt ggttgccatc tgcgtgattt tctccatgtc cttcgtccca   2460
gccagctttg tcctttattt gatccaggag cgggtgaaca aatccaagca cctccagttt   2520
atcagtggag tgagccccac cacctactgg gtaaccaact tcctctggga catcatgaat   2580
tattccgtga gtgctgggct ggtggtgggc atcttcatcg ggtttcagaa gaaagcctac   2640
acttctccag aaaaccttcc tgcccttgtg gcactgctcc tgctgtatgg atgggcggtc   2700
attcccatga tgtacccagc atccttcctg tttgatgtcc ccagcacagc ctatgtggct   2760
ttatcttgtg ctaatctgtt catcggcatc aacagcagtg ctattacctt catcttggaa   2820
ttatttgaga ataaccggac gctgctcagg ttcaacgccg tgctgaggaa gctgctcatt   2880
gtcttccccc acttctgcct gggccggggc ctcattgacc ttgcactgag ccaggctgtg   2940
acagatgtct atgcccggtt tggtgaggag cactctgcaa atccgttcca ctgggacctg   3000
attgggaaga acctgtttgc catggtggtg gaaggggtgg tgtacttcct cctgaccctg   3060
ctggtccagc gccacttctt cctctcccaa tggattgccg agcccactaa ggagcccatt   3120
gttgatgaag atgatgatgt ggctgaagaa agacaaagaa ttattactgg tggaaataaa   3180
actgacatct taaggctaca tgaactaacc aagatttatc caggcacctc cagcccagca   3240
gtggacaggc tgtgtgtcgg agttcgccct ggagagtgct ttggcctcct gggagtgaat   3300
ggtgccggca aaacaaccac attcaagatg ctcactgggg acaccacagt gacctcaggg   3360
gatgccaccg tagcaggcaa gagtatttta accaatattt ctgaagtcca tcaaaatatg   3420
ggctactgtc ctcagtttga tgcaatcgat gagctgctca caggacgaga acatctttac   3480
ctttatgccc ggcttcgagg tgtaccagca gaagaaatcg aaaaggttgc aaactggagt   3540
attaagagcc tgggcctgac tgtctacgcc gactgcctgg ctggcacgta cagtgggggc   3600
aacaagcgga aactctccac agccatcgca ctcattggct gcccaccgct ggtgctgctg   3660
gatgagccca ccacagggat ggacccccag gcacgccgca tgctgtggaa cgtcatcgtg   3720
agcatcatca gagaagggag ggctgtggtc ctcacatccc acagcatgga agaatgtgag   3780
gcactgtgta cccggctggc catcatggta aagggcgcct ttcgatgtat gggcaccatt   3840
cagcatctca agtccaaatt tggagatggc tatatcgtca caatgaagat caaatccccg   3900
aaggacgacc tgcttcctga cctgaaccct gtggagcagt tcttccaggg gaacttccca   3960
ggcagtgtgc agagggagag gcactacaac atgctccagt tccaggtctc ctcctcctcc   4020
ctggcgagga tcttccagct cctcctctcc cacaaggaca gcctgctcat cgaggagtac   4080
tcagtcacac agaccacact ggaccaggtg tttgtaaatt ttgctaaaca gcagactgaa   4140
agtcatgacc tccctctgca ccctcgagct gctggagcca gtcgacaagc ccaggactga   4200
gcggccgctt cgagcagaca tgataagata cattgatgag tttggacaaa ccacaactag   4260
aatgcagtga aaaaaatgct ttatttgtga aatttgtgat gctattgctt tatttgtaac   4320
cattataagc tgcaataaac aagttaacaa caacaattgc attcatttta tgtttcaggt   4380
tcagggggag atgtgggagg ttttttaaag caagtaaaac ctctacaaat gtggtaaaat   4440
```

```
cgataaggat cttcctagag catggctacg tagataagta gcatggcggg ttaatcatta   4500

actacaagga acccctagtg atggagttgg ccactccctc tctgcgcgct cgctcgctca   4560

ctgaggccgg gcgaccaaag gtcgcccgac gcccgggctt tgcccgggcg gcctcagtga   4620

gcgagcgagc gcgcag                                                   4636
```

<210> SEQ ID NO 16
<211> LENGTH: 4431
<212> TYPE: DNA
<213> ORGANISM: Artificial Sequence
<220> FEATURE:
<223> OTHER INFORMATION: synthetic

<400> SEQUENCE: 16

```
ctgcgcgctc gctcgctcac tgaggccgcc cgggcaaagc ccgggcgtcg ggcgaccttt     60

ggtcgcccgg cctcagtgag cgagcgagcg cgcagagagg gagtggccaa ctccatcact    120

aggggttcct tgtagttaat gattaacccg ccatgctact tatctacgta gccatgctct    180

aggaagatct tcaatattgg ccattagcca tattattcat tggttatata gcataaatca    240

atattggcta ttggccattg catacgttgt atctatatca taatatgtac atttatattg    300

gctcatgtcc aatatgaccg ccatgttggc attgattatt gactagttat taatagtaat    360

caattacggg gtcattagtt catagcccat atatggagtt ccgcgttaca taacttacgg    420

taaatggccc gcctggctga ccgcccaacg acccccgccc attgacgtca ataatgacgt    480

atgttcccat agtaacgcca atagggactt tccattgacg tcaatgggtg gagtatttac    540

ggtaaactgc ccacttggca gtacatcaag tgtatcatat gccaagtccg ccccctattg    600

acgtcaatga cggtaaatgg cccgcctggc attatgccca gtacatgacc ttacgggact    660

ttcctacttg gcagtacatc tacgtattag tcatcgctat taccatggtg atgcggtttt    720

ggcagtacac caatgggcgt ggatagcggt ttgactcacg gggatttcca agtctccacc    780

ccattgacgt caatgggagt ttgttttggc accaaaatca acgggacttt ccaaaatgtc    840

gtaataaccc cgccccgttg acgcaaatgg gcggtaggcg tgtacggtgg gaggtctata    900

taagcagagc tcgtttagtg aaccgtcaga tcactagaag ctttattgcg gtagtttatc    960

acagttaaat tgctaacgca gtcagtgctt ctgacacaac agtctcgaac ttaagctgca   1020

gaagttggtc gtgaggcact gggcaggtaa gtatcaaggt tacaagacag gtttaaggag   1080

accaatagaa actgggcttg tcgagacaga gaagactctt gcgtttctga taggcaccta   1140

ttggtcttac tgacatccac tttgcctttc tctccacagg tgtccactcc cagttcaatt   1200

acagctctta aggctagagt acttaatacg actcactata ggctagcctc gagaattcac   1260

gcgtggtacc tctagagtcg acccgggcgg ccgccatggg cttcgtgaga cagatacagc   1320

ttttgctctg gaagaactgg accctgcgga aaaggcaaaa gattcgcttt gtggtggaac   1380

tcgtgtggcc tttatcttta tttctggtct tgatctggtt aaggaatgcc aacccgctct   1440

acagccatca tgaatgccat ttccccaaca aggcgatgcc ctcagcagga atgctgccgt   1500

ggctccaggg gatcttctgc aatgtgaaca atccctgttt tcaaagcccc accccaggag   1560

aatctcctgg aattgtgtca aactataaca actccatctt ggcaagggta tatcgagatt   1620

ttcaagaact cctcatgaat gcaccagaga gccagcacct tggccgtatt tggacagagc   1680

tacacatctt gtcccaattc atggacaccc tccggactca cccggagaga attgcaggaa   1740

gaggaattcg aataagggat atcttgaaag atgaagaaac actgacacta tttctcatta   1800
```

-continued

```
aaaacatcgg cctgtctgac tcagtggtct accttctgat caactctcaa gtccgtccag   1860
agcagttcgc tcatggagtc ccggacctgg cgctgaagga catcgcctgc agcgaggccc   1920
tcctggagcg cttcatcatc ttcagccaga gacgcggggc aaagacggtg cgctatgccc   1980
tgtgctccct ctcccagggc accctacagt ggatagaaga cactctgtat gccaacgtgg   2040
acttcttcaa gctcttccgt gtgcttccca cactcctaga cagccgttct caaggtatca   2100
atctgagatc ttggggagga atattatctg atatgtcacc aagaattcaa gagtttatcc   2160
atcggccgag tatgcaggac ttgctgtggg tgaccaggcc cctcatgcag aatggtggtc   2220
cagagacctt tacaaagctg atgggcatcc tgtctgacct cctgtgtggc taccccgagg   2280
gaggtggctc tcgggtgctc tccttcaact ggtatgaaga caataactat aaggcctttc   2340
tggggattga ctccacaagg aaggatccta tctattctta tgacagaaga acaacatcct   2400
tttgtaatgc attgatccag agcctggagt caaatccttt aaccaaaatc gcttggaggg   2460
cggcaaagcc tttgctgatg ggaaaaatcc tgtacactcc tgattcacct gcagcacgaa   2520
ggatactgaa gaatgccaac tcaacttttg aagaactgga acacgttagg aagttggtca   2580
aagcctggga agaagtaggg ccccagatct ggtacttctt tgacaacagc acacagatga   2640
acatgatcag agataccctg ggaacccaa cagtaaaaga ctttttgaat aggcagcttg   2700
gtgaagaagg tattactgct gaagccatcc taaacttcct ctacaagggc cctcgggaaa   2760
gccaggctga cgacatggcc aacttcgact ggagggacat atttaacatc actgatcgca   2820
ccctccgcct tgtcaatcaa tacctggagt gcttggtcct ggataagttt gaaagctaca   2880
atgatgaaac tcagctcacc caacgtgccc tctctctact ggaggaaaac atgttctggg   2940
ccggagtggt attccctgac atgtatccct ggaccagctc tctaccaccc cacgtgaagt   3000
ataagatccg aatggacata gacgtggtgg agaaaaccaa taagattaaa gacaggtatt   3060
gggattctgg tcccagagct gatcccgtgg aagatttccg gtacatctgg ggcgggtttg   3120
cctatctgca ggacatggtt gaacagggga tcacaaggag ccaggtgcag gcggaggctc   3180
cagttggaat ctacctccag cagatgccct accccctgctt cgtggacgat tctttcatga   3240
tcatcctgaa ccgctgtttc cctatcttca tggtgctggc atggatctac tctgtctcca   3300
tgactgtgaa gagcatcgtc ttggagaagg agttgcgact gaaggagacc ttgaaaaatc   3360
agggtgtctc caatgcagtg atttggtgta cctggttcct ggacagcttc tccatcatgt   3420
cgatgagcat cttcctcctg acgatattca tcatgcatgg aagaatccta cattacagcg   3480
acccattcat cctcttcctg ttcttgttgg ctttctccac tgccaccatc atgctgtgct   3540
ttctgctcag caccttcttc tccaaggcca gtctggcagc agcctgtagt ggtgtcatct   3600
atttcaccct ctacctgcca cacatcctgt gcttcgcctg gcaggaccgc atgaccgctg   3660
agctgaagaa ggctgtgagc ttactgtctc cggtggcatt tggatttggc actgagtacc   3720
tggttcgctt tgaagagcaa ggcctggggc tgcagtggag caacatcggg aacagtccca   3780
cggaagggga cgaattcagc ttcctgctgt ccatgcagat gatgctcctt gatgctgctg   3840
tctatggctt actcgcttgg taccttgatc aggtgtttcc aggagactat ggaaccccac   3900
ttccttggta ctttcttcta caagagtcgt attggcttgg cggtgaaggg tgttcaacca   3960
gagaagaaag agccctggaa aagaccgagc ccctaacaga ggaaacggag gatccagagc   4020
acccagaagg aatacacgac tccttctttg aacgtgagca tccagggtgg gttcctgggg   4080
tatgcgtgaa gaatctggta aagatttttg agccctgtgg ccggccagct gtggaccgtc   4140
tgaacatcac cttctacgag aaccagatca ccgcattcct gggccacaat ggagctggga   4200
```

```
aaaccaccac cttgtaagta tcaaggttac aagacaggtt taaggagacc aatagaaact   4260

gggcttgtcg agacagagaa gactcttgcg tttctcaatt gaggaacccc tagtgatgga   4320

gttggccact ccctctctgc gcgctcgctc gctcactgag gccgggcgac caaaggtcgc   4380

ccgacgcccg ggctttgccc gggcggcctc agtgagcgag cgagcgcgca g            4431
```

<210> SEQ ID NO 17
<211> LENGTH: 4521
<212> TYPE: DNA
<213> ORGANISM: Artificial Sequence
<220> FEATURE:
<223> OTHER INFORMATION: synthetic

<400> SEQUENCE: 17

```
ctgcgcgctc gctcgctcac tgaggccgcc cgggcaaagc ccgggcgtcg ggcgaccttt     60

ggtcgcccgg cctcagtgag cgagcgagcg cgcagagagg gagtggccaa ctccatcact    120

aggggttcct gataggcacc tattggtctt actgacatcc actttgcctt tctctccaca    180

ggtccatcct gacgggtctg ttgccaccaa cctctgggac tgtgctcgtt gggggaaggg    240

acattgaaac cagcctggat gcagtccggc agagccttgg catgtgtcca cagcacaaca    300

tcctgttcca ccacctcacg gtggctgagc acatgctgtt ctatgcccag ctgaaaggaa    360

agtcccagga ggaggcccag ctggagatgg aagccatgtt ggaggacaca ggcctccacc    420

acaagcggaa tgaagaggct caggacctat caggtggcat gcagagaaag ctgtcggttg    480

ccattgcctt tgtgggagat gccaaggtgg tgattctgga cgaacccacc tctggggtgg    540

acccttactc gagacgctca atctgggatc tgctcctgaa gtatcgctca ggcagaacca    600

tcatcatgtc cactcaccac atggacgagg ccgacctcct tggggaccgc attgccatca    660

ttgcccaggg aaggctctac tgctcaggca ccccactctt cctgaagaac tgctttggca    720

caggcttgta cttaaccttg gtgcgcaaga tgaaaaacat ccagagccaa aggaaaggca    780

gtgaggggac ctgcagctgc tcgtctaagg gtttctccac cacgtgtcca gcccacgtcg    840

atgacctaac tccagaacaa gtcctggatg gggatgtaaa tgagctgatg gatgtagttc    900

tccaccatgt tccagaggca aagctggtgg agtgcattgg tcaagaactt atcttccttc    960

ttccaaataa gaacttcaag cacagagcat atgccagcct tttcagagag ctggaggaga   1020

cgctggctga ccttggtctc agcagttttg gaatttctga cactcccctg gaagagattt   1080

ttctgaaggt cacggaggat tctgattcag gacctctgtt tgcgggtggc gctcagcaga   1140

aaagagaaaa cgtcaacccc cgacacccct gcttgggtcc cagagagaag gctggacaga   1200

caccccagga ctccaatgtc tgctccccag gggcgccggc tgctcaccca gagggccagc   1260

ctcccccaga gccagagtgc ccaggcccgc agctcaacac ggggacacag ctggtcctcc   1320

agcatgtgca ggcgctgctg gtcaagagat tccaacacac catccgcagc cacaaggact   1380

tcctggcgca gatcgtgctc ccggctacct ttgtgttttt ggctctgatg ctttctattg   1440

ttatccctcc ttttggcgaa taccccgctt tgacccttca cccctggata tatgggcagc   1500

agtacacctt cttcagcatg gatgaaccag gcagtgagca gttcacggta cttgcagacg   1560

tcctcctgaa taagccaggc tttggcaacc gctgcctgaa ggaagggtgg cttccggagt   1620

acccctgtgg caactcaaca ccctggaaga ctccttctgt gtccccaaac atcacccagc   1680

tgttccagaa gcagaaatgg acacaggtca acccttcacc atcctgcagg tgcagcacca   1740

gggagaagct caccatgctg ccagagtgcc ccgagggtgc cgggggcctc ccgccccccc   1800
```

-continued

```
agagaacaca gcgcagcacg gaaattctac aagacctgac ggacaggaac atctccgact   1860
tcttggtaaa aacgtatcct gctcttataa gaagcagctt aaagagcaaa ttctgggtca   1920
atgaacagag gtatggagga atttccattg gaggaaagct cccagtcgtc cccatcacgg   1980
gggaagcact tgttgggttt ttaagcgacc ttggccggat catgaatgtg agcgggggcc   2040
ctatcactag agaggcctct aaagaaatac ctgatttcct taaacatcta gaaactgaag   2100
acaacattaa ggtgtggttt aataacaaag gctggcatgc cctggtcagc tttctcaatg   2160
tggcccacaa cgccatctta cgggccagcc tgcctaagga cagaagcccc gaggagtatg   2220
gaatcaccgt cattagccaa cccctgaacc tgaccaagga gcagctctca gagattacag   2280
tgctgaccac ttcagtggat gctgtggttg ccatctgcgt gattttctcc atgtccttcg   2340
tcccagccag ctttgtcctt tatttgatcc aggagcgggt gaacaaatcc aagcacctcc   2400
agtttatcag tggagtgagc cccaccacct actgggtaac caacttcctc tgggacatca   2460
tgaattattc cgtgagtgct gggctggtgg tgggcatctt catcgggttt cagaagaaag   2520
cctacacttc tccagaaaac cttcctgccc ttgtggcact gctcctgctg tatggatggg   2580
cggtcattcc catgatgtac ccagcatcct tcctgtttga tgtccccagc acagcctatg   2640
tggctttatc ttgtgctaat ctgttcatcg gcatcaacag cagtgctatt accttcatct   2700
tggaattatt tgagaataac cggacgctgc tcaggttcaa cgccgtgctg aggaagctgc   2760
tcattgtctt cccccacttc tgcctgggcc ggggcctcat tgaccttgca ctgagccagg   2820
ctgtgacaga tgtctatgcc cggtttggtg aggagcactc tgcaaatccg ttccactggg   2880
acctgattgg gaagaacctg tttgccatgg tggtggaagg ggtggtgtac ttcctcctga   2940
ccctgctggt ccagcgccac ttcttcctct cccaatggat tgccgagccc actaaggagc   3000
ccattgttga tgaagatgat gatgtggctg aagaaagaca aagaattatt actggtggaa   3060
ataaaactga catcttaagg ctacatgaac taaccaagat ttatccaggc acctccagcc   3120
cagcagtgga caggctgtgt gtcggagttc gccctggaga gtgctttggc ctcctgggag   3180
tgaatggtgc cggcaaaaca accacattca agatgctcac tggggacacc acagtgacct   3240
caggggatgc caccgtagca ggcaagagta ttttaaccaa tatttctgaa gtccatcaaa   3300
atatgggcta ctgtcctcag tttgatgcaa tcgatgagct gctcacagga cgagaacatc   3360
tttacccttta tgcccggctt cgaggtgtac cagcagaaga aatcgaaaag gttgcaaact   3420
ggagtattaa gagcctgggc ctgactgtct acgccgactg cctggctggc acgtacagtg   3480
ggggcaacaa gcggaaactc tccacagcca tcgcactcat tggctgccca ccgctggtgc   3540
tgctggatga gcccaccaca gggatggacc cccaggcacg ccgcatgctg tggaacgtca   3600
tcgtgagcat catcagagaa gggagggctg tggtcctcac atcccacagc atggaagaat   3660
gtgaggcact gtgtacccgg ctggccatca tggtaaaggg cgcctttcga tgtatgggca   3720
ccattcagca tctcaagtcc aaatttggag atggctatat cgtcacaatg aagatcaaat   3780
ccccgaagga cgacctgctt cctgacctga accctgtgga gcagttcttc caggggaact   3840
tcccaggcag tgtgcagagg gagaggcact acaacatgct ccagttccag gtctcctcct   3900
cctccctggc gaggatcttc cagctcctcc tctcccacaa ggacagcctg ctcatcgagg   3960
agtactcagt cacacagacc acactggacc aggtgtttgt aaattttgct aaacagcaga   4020
ctgaaagtca tgacctccct ctgcaccctc gagctgctgg agccagtcga caagcccagg   4080
actgagcggc cgcttcgagc agacatgata agatacattg atgagtttgg acaaaccaca   4140
actagaatgc agtgaaaaaa atgctttatt tgtgaaattt gtgatgctat tgctttattt   4200
```

```
gtaaccatta taagctgcaa taaacaagtt aacaacaaca attgcattca ttttatgttt   4260

caggttcagg gggagatgtg ggaggttttt taaagcaagt aaaacctcta caaatgtggt   4320

aaaatcgata aggatcttcc tagagcatgg ctacgtagat aagtagcatg gcgggttaat   4380

cattaactac aaggaacccc tagtgatgga gttggccact ccctctctgc gcgctcgctc   4440

gctcactgag gccgggcgac caaaggtcgc ccgacgcccg ggctttgccc gggcggcctc   4500

agtgagcgag cgagcgcgca g                                              4521
```

<210> SEQ ID NO 18
<211> LENGTH: 175
<212> TYPE: DNA
<213> ORGANISM: Artificial Sequence
<220> FEATURE:
<223> OTHER INFORMATION: synthetic

<400> SEQUENCE: 18

```
ctctccccccc tgtcgcgttc gctcgctcgc tggctcgttt gggggggtgg cagctcaaag     60

agctgccaga cgacggccct ctggccgtcg ccccccccaaa cgagccagcg agcgagcgaa    120

cgcgacaggg gggagagtgc cacactctca agcaaggggg ttttgtaagc agtga          175
```

<210> SEQ ID NO 19
<211> LENGTH: 400
<212> TYPE: DNA
<213> ORGANISM: Artificial Sequence
<220> FEATURE:
<223> OTHER INFORMATION: synthetic

<400> SEQUENCE: 19

```
gctagcgtgc cacctggtcg acattgatta ttgactagtt attaatagta atcaattacg     60

gggtcattag ttcatagccc atatatggag ttccgcgtta cataacttac ggtaaatggc    120

ccgcctggct gaccgcccaa cgacccccgc ccattgacgt caataatgac gtatgttccc    180

atagtaacgc caatagggac tttccattga cgtcaatggg tggactattt acggtaaact    240

gcccacttgg cagtacatca agtgtatcat atgccaagta cgccccctat tgacgtcaat    300

gacggtaaat ggcccgcctg gcattatgcc cagtacatga ccttatggga ctttcctact    360

tggcagtaca tctacgtatt agtcatcgct attaccatgg                          400
```

<210> SEQ ID NO 20
<211> LENGTH: 277
<212> TYPE: DNA
<213> ORGANISM: Artificial Sequence
<220> FEATURE:
<223> OTHER INFORMATION: synthetic

<400> SEQUENCE: 20

```
tcgaggtgag ccccacgttc tgcttcactc tccccatctc ccccccctcc ccacccccaa     60

ttttgtattt atttattttt taattatttt gtgcagcgat gggggcgggg gggggggggg    120

cgcgcgccag gcggggcggg gcggggcgag gggcggggcg gggcgaggcg gagaggtgcg    180

gcggcagcca atcagagcgg cgcgctccga aagtttcctt ttatggcgag gcggcggcgg    240

cggcggccct ataaaaagcg aagcgcgcgg cgggcgg                             277
```

<210> SEQ ID NO 21
<211> LENGTH: 133
<212> TYPE: DNA
<213> ORGANISM: Artificial Sequence
<220> FEATURE:

<223> OTHER INFORMATION: synthetic

<400> SEQUENCE: 21

```
gtaagtatca aggttacaag acaggtttaa ggagaccaat agaaactggg cttgtcgaga     60

cagagaagac tcttgcgttt ctgataggca cctattggtc ttactgacat ccactttgcc    120

tttctctcca cag                                                       133
```

<210> SEQ ID NO 22
<211> LENGTH: 3108
<212> TYPE: DNA
<213> ORGANISM: Artificial Sequence
<220> FEATURE:
<223> OTHER INFORMATION: synthetic

<400> SEQUENCE: 22

```
atggtgattc ttcagcaggg ggaccatgtg tggatggacc tgagattggg gcaggagttc     60

gacgtgccca tcggggcggt ggtgaagctc tgcgactctg ggcaggtcca ggtggtggat    120

gatgaagaca atgaacactg gatctctccg cagaacgcaa cgcacatcaa gcctatgcac    180

cccacgtcgg tccacggcgt ggaggacatg atccgcctgg gggacctcaa cgaggcgggc    240

atcttgcgca acctgcttat ccgctaccgg gaccacctca tctacacgta tacgggctcc    300

atcctggtgg ctgtgaaccc ctaccagctg ctctccatct actcgccaga gcacatccgc    360

cagtatacca acaagaagat tggggagatg cccccccaca tctttgccat tgctgacaac    420

tgctacttca acatgaaacg caacagccga gaccagtgct gcatcatcag tggggaatct    480

ggggccggga agacggagag cacaaagctg atcctgcagt tcctggcagc catcagtggg    540

cagcactcgt ggattgagca gcaggtcttg gaggccaccc ccattctgga agcatttggg    600

aatgccaaga ccatccgcaa tgacaactca agccgtttcg gaaagtacat cgacatccac    660

ttcaacaagc ggggcgccat cgagggcgcg aagattgagc agtacctgct ggaaaagtca    720

cgtgtctgtc gccaggccct ggatgaaagg aactaccacg tgttctactg catgctggag    780

ggcatgagtg aggatcagaa gaagaagctg ggcttgggcc aggcctctga ctacaactac    840

ttggccatgg gtaactgcat aacctgtgag ggccgggtgg acagccagga gtacgccaac    900

atccgctccg ccatgaaggt gctcatgttc actgacaccg agaactggga gatctcgaag    960

ctcctggctg ccatcctgca cctgggcaac ctgcagtatg aggcacgcac atttgaaaac   1020

ctggatgcct gtgaggttct cttctcccca tcgctggcca cagctgcatc cctgcttgag   1080

gtgaaccccc cagacctgat gagctgcctg actagccgca ccctcatcac ccgcggggag   1140

acggtgtcca ccccactgag cagggaacag gcactggacg tgcgcgacgc cttcgtaaag   1200

gggatctacg ggcggctgtt cgtgtggatt gtggacaaga tcaacgcagc aatttacaag   1260

cctccctccc aggatgtgaa gaactctcgc aggtccatcg gcctcctgga catctttggg   1320

tttgagaact ttgctgtgaa cagctttgag cagctctgca tcaacttcgc caatgagcac   1380

ctgcagcagt tctttgtgcg gcacgtgttc aagctggagc aggaggaata tgacctggag   1440

agcattgact ggctgcacat cgagttcact gacaaccagg atgccctgga catgattgcc   1500

aacaagccca tgaacatcat ctccctcatc gatgaggaga gcaagttccc caagggcaca   1560

gacaccacca tgttacacaa gctgaactcc cagcacaagc tcaacgccaa ctacatcccc   1620

cccaagaaca accatgagac ccagtttggc atcaaccatt ttgcaggcat cgtctactat   1680

gagacccaag gcttcctgga gaagaaccga gacaccctgc atggggacat tatccagctg   1740

gtccactcct ccaggaacaa gttcatcaag cagatcttcc aggccgatgt cgccatgggc   1800
```

```
gccgagacca ggaagcgctc gcccacactt agcagccagt tcaagcggtc actggagctg   1860
ctgatgcgca cgctgggtgc ctgccagccc ttctttgtgc gatgcatcaa gcccaatgag   1920
ttcaagaagc ccatgctgtt cgaccggcac ctgtgcgtgc gccagctgcg gtactcagga   1980
atgatggaga ccatccgaat ccgccgagct ggctacccca tccgctacag cttcgtagag   2040
tttgtggagc ggtaccgtgt gctgctgcca ggtgtgaagc cggcctacaa gcagggcgac   2100
ctccgcggga cttgccagcg catggctgag gctgtgctgg gcacccacga tgactggcag   2160
ataggcaaaa ccaagatctt tctgaaggac caccatgaca tgctgctgga agtggagcgg   2220
gacaaagcca tcaccgacag agtcatcctc cttcagaaag tcatccgggg attcaaagac   2280
aggtctaact ttctgaagct gaagaacgct gccacactga tccagaggca ctggcggggt   2340
cacaactgta ggaagaacta cgggctgatg cgtctgggct tcctgcggct gcaggccctg   2400
caccgctccc ggaagctgca ccagcagtac cgcctggccc gccagcgcat catccagttc   2460
caggcccgct gccgcgccta tctggtgcgc aaggccttcc gccaccgcct ctgggctgtg   2520
ctcaccgtgc aggcctatgc ccggggcatg atcgcccgca ggctgcacca acgcctcagg   2580
gctgagtatc tgtggcgcct cgaggctgag aaaatgcggc tggcggagga agagaagctt   2640
cggaaggaga tgagcgccaa gaaggccaag gaggaggccg agcgcaagca tcaggagcgc   2700
ctggcccagc tggctcgtga ggacgctgag cgggagctga aggagaagga ggccgctcgg   2760
cggaagaagg agctcctgga gcagatggaa agggcccgcc atgagcctgt caatcactca   2820
gacatggtgg acaagatgtt tggcttcctg gggacttcag gtggcctgcc aggccaggag   2880
ggccaggcac ctagtggctt tgaggacctg gagcgagggc ggagggagat ggtggaggag   2940
gacctggatg cagccctgcc cctgcctgac gaggatgagg aggacctctc tgagtataaa   3000
tttgccaagt tcgcggccac ctacttccag gggacaacta cgcactccta cacccggcgg   3060
ccactcaaac agccactgct ctaccatgac gacgagggtg accagctg                3108
```

```
<210> SEQ ID NO 23
<211> LENGTH: 4577
<212> TYPE: DNA
<213> ORGANISM: Artificial Sequence
<220> FEATURE:
<223> OTHER INFORMATION: synthetic

<400> SEQUENCE: 23

ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct tgtagttaat gattaacccg ccatgctact tatctacgta gccatgctct    180
aggaagatcc taatcgggaa ttcgccctta agctagcgtg ccacctggtc gacattgatt    240
attgactagt tattaatagt aatcaattac ggggtcatta gttcatagcc catatatgga    300
gttccgcgtt acataactta cggtaaatgg cccgcctggc tgaccgccca acgacccccg    360
cccattgacg tcaataatga cgtatgttcc catagtaacg ccaataggga ctttccattg    420
acgtcaatgg gtggactatt tacggtaaac tgcccacttg gcagtacatc aagtgtatca    480
tatgccaagt acgcccccta ttgacgtcaa tgacggtaaa tggcccgcct ggcattatgc    540
ccagtacatg accttatggg actttcctac ttggcagtac atctacgtat tagtcatcgc    600
tattaccatg ggtcgaggtg agccccacgt tctgcttcac tctccccatc tcccccccct    660
ccccaccccc aattttgtat ttatttattt tttaattatt ttgtgcagcg atgggggcgg    720
```

```
gggggggggg ggcgcgcgcc aggcggggcg gggcggggcg aggggcgggg cggggcgagg    780
cggagaggtg cggcggcagc caatcagagc ggcgcgctcc gaaagtttcc ttttatggcg    840
aggcggcggc ggcggcggcc ctataaaaag cgaagcgcgc ggcgggcggc tgcagaagtt    900
ggtcgtgagg cactgggcag gtaagtatca aggttacaag acaggtttaa ggagaccaat    960
agaaactggg cttgtcgaga cagagaagac tcttgcgttt ctgataggca cctattggtc   1020
ttactgacat ccactttgcc tttctctcca caggtgtcca ggcggccgcc atggtgattc   1080
ttcagcaggg ggaccatgtg tggatggacc tgagattggg gcaggagttc gacgtgccca   1140
tcggggcggt ggtgaagctc tgcgactctg ggcaggtcca ggtggtggat gatgaagaca   1200
atgaacactg gatctctccg cagaacgcaa cgcacatcaa gcctatgcac cccacgtcgg   1260
tccacggcgt ggaggacatg atccgcctgg gggacctcaa cgaggcgggc atcttgcgca   1320
acctgcttat ccgctaccgg gaccacctca tctacacgta tacgggctcc atcctggtgg   1380
ctgtgaaccc ctaccagctg ctctccatct actcgccaga gcacatccgc cagtatacca   1440
acaagaagat tggggagatg cccccccaca tctttgccat tgctgacaac tgctacttca   1500
acatgaaacg caacagccga gaccagtgct gcatcatcag tggggaatct ggggccggga   1560
agacggagag cacaaagctg atcctgcagt tcctggcagc catcagtggg cagcactcgt   1620
ggattgagca gcaggtcttg gaggccaccc ccattctgga agcatttggg aatgccaaga   1680
ccatccgcaa tgacaactca agccgtttcg gaaagtacat cgacatccac ttcaacaagc   1740
ggggcgccat cgagggcgcg aagattgagc agtacctgct ggaaaagtca cgtgtctgtc   1800
gccaggccct ggatgaaagg aactaccacg tgttctactg catgctggag ggcatgagtg   1860
aggatcagaa gaagaagctg ggcttgggcc aggcctctga ctacaactac ttggccatgg   1920
gtaactgcat aacctgtgag ggccgggtgg acagccagga gtacgccaac atccgctccg   1980
ccatgaaggt gctcatgttc actgacaccg agaactggga gatctcgaag ctcctggctg   2040
ccatcctgca cctgggcaac ctgcagtatg aggcacgcac atttgaaaac ctggatgcct   2100
gtgaggttct cttctcccca tcgctggcca cagctgcatc cctgcttgag gtgaaccccc   2160
cagacctgat gagctgcctg actagccgca ccctcatcac ccgcggggag acggtgtcca   2220
ccccactgag cagggaacag gcactggacg tgcgcgacgc cttcgtaaag gggatctacg   2280
ggcggctgtt cgtgtggatt gtggacaaga tcaacgcagc aatttacaag cctccctccc   2340
aggatgtgaa gaactctcgc aggtccatcg gcctcctgga catctttggg tttgagaact   2400
ttgctgtgaa cagctttgag cagctctgca tcaacttcgc caatgagcac ctgcagcagt   2460
tctttgtgcg gcacgtgttc aagctggagc aggaggaata tgacctggag agcattgact   2520
ggctgcacat cgagttcact gacaaccagg atgccctgga catgattgcc aacaagccca   2580
tgaacatcat ctccctcatc gatgaggaga gcaagttccc caagggcaca gacaccacca   2640
tgttacacaa gctgaactcc cagcacaagc tcaacgccaa ctacatcccc cccaagaaca   2700
accatgagac ccagtttggc atcaaccatt ttgcaggcat cgtctactat gagacccaag   2760
gcttcctgga gaagaaccga gacaccctgc atggggacat tatccagctg gtccactcct   2820
ccaggaacaa gttcatcaag cagatcttcc aggccgatgt cgccatgggc gccgagacca   2880
ggaagcgctc gcccacactt agcagccagt tcaagcggtc actggagctg ctgatgcgca   2940
cgctgggtgc ctgccagccc ttctttgtgc gatgcatcaa gcccaatgag ttcaagaagc   3000
ccatgctgtt cgaccggcac ctgtgcgtgc gccagctgcg gtactcagga atgatggaga   3060
ccatccgaat ccgccgagct ggctacccca tccgctacag cttcgtagag tttgtggagc   3120
```

```
ggtaccgtgt gctgctgcca ggtgtgaagc cggcctacaa gcagggcgac ctccgcggga   3180
cttgccagcg catggctgag gctgtgctgg gcacccacga tgactggcag ataggcaaaa   3240
ccaagatctt tctgaaggac caccatgaca tgctgctgga agtggagcgg gacaaagcca   3300
tcaccgacag agtcatcctc cttcagaaag tcatccgggg attcaaagac aggtctaact   3360
ttctgaagct gaagaacgct gccacactga tccagaggca ctggcggggt cacaactgta   3420
ggaagaacta cgggctgatg cgtctgggct tcctgcggct gcaggccctg caccgctccc   3480
ggaagctgca ccagcagtac cgcctggccc gccagcgcat catccagttc caggcccgct   3540
gccgcgccta tctggtgcgc aaggccttcc gccaccgcct ctgggctgtg ctcaccgtgc   3600
aggcctatgc ccggggcatg atcgcccgca ggctgcacca acgcctcagg gctgagtatc   3660
tgtggcgcct cgaggctgag aaaatgcggc tggcggagga agagaagctt cggaaggaga   3720
tgagcgccaa gaaggccaag gaggaggccg agcgcaagca tcaggagcgc ctggcccagc   3780
tggctcgtga ggacgctgag cgggagctga aggagaagga ggccgctcgg cggaagaagg   3840
agctcctgga gcagatggaa agggcccgcc atgagcctgt caatcactca gacatggtgg   3900
acaagatgtt tggcttcctg gggacttcag gtggcctgcc aggccaggag ggccaggcac   3960
ctagtggctt tgaggacctg gagcgagggc ggagggagat ggtggaggag gacctggatg   4020
cagccctgcc cctgcctgac gaggatgagg aggacctctc tgagtataaa tttgccaagt   4080
tcgcggccac ctacttccag gggacaacta cgcactccta cacccggcgg ccactcaaac   4140
agccactgct ctaccatgac gacgagggtg accagctggt aagtatcaag gttacaagac   4200
aggtttaagg agaccaatag aaactgggct tgtcgagaca gagaagactc ttgcgtttct   4260
gggattttgc cgatttcggc ctattggtta aaaaatgagc tgatttaaca aaaatttaac   4320
gcgaatttta acaaaatatt aacgtttata atttcaggtg gcatctttcc aattgaaggg   4380
cgaattccga tcttcctaga gcatggctac gtagataagt agcatggcgg gttaatcatt   4440
aactacaagg aacccctagt gatggagttg gccactccct ctctgcgcgc tcgctcgctc   4500
actgaggccg ggcgaccaaa ggtcgcccga cgcccgggct ttgcccgggc ggcctcagtg   4560
agcgagcgag cgcgcag                                                  4577
```

<210> SEQ ID NO 24
<211> LENGTH: 3540
<212> TYPE: DNA
<213> ORGANISM: Artificial Sequence
<220> FEATURE:
<223> OTHER INFORMATION: synthetic

<400> SEQUENCE: 24

```
gcagccctgg cggtctggat caccatcctc cgcttcatgg gggacctccc tgagcccaag     60
taccacacag ccatgagtga tggcagtgag aagatccctg tgatgaccaa gatttatgag    120
accctgggca agaagacgta caagagggag ctgcaggccc tgcagggcga gggcgaggcc    180
cagctccccg agggccagaa gaagagcagt gtgaggcaca agctggtgca tttgactctg    240
aaaaagaagt ccaagctcac agaggaggtg accaagaggc tgcatgacgg ggagtccaca    300
gtgcagggca acagcatgct ggaggaccgg cccacctcca acctggagaa gctgcacttc    360
atcatcggca atggcatcct gcggccagca ctccgggacg agatctactg ccagatcagc    420
aagcagctga cccacaaccc ctccaagagc agctatgccc ggggctggat tctcgtgtct    480
ctctgcgtgg gctgtttcgc cccctccgag aagtttgtca agtacctgcg gaacttcatc    540
```

```
cacgggggcc cgcccggcta cgccccgtac tgtgaggagc gcctgagaag gacctttgtc    600
aatgggacac ggacacagcc gcccagctgg ctggagctgc aggccaccaa gtccaagaag    660
ccaatcatgt tgcccgtgac attcatggat gggaccacca agaccctgct gacggactcg    720
gcaaccacgg ccaaggagct ctgcaacgcg ctggccgaca agatctctct caaggaccgg    780
ttcgggttct ccctctacat tgccctgttt gacaaggtgt cctccctggg cagcggcagt    840
gaccacgtca tggacgccat ctcccagtgc gagcagtacg ccaaggagca gggcgcccag    900
gagcgcaacg ccccctggag gctcttcttc cgcaaagagg tcttcacgcc ctggcacagc    960
ccctccgagg acaacgtggc caccaacctc atctaccagc aggtggtgcg aggagtcaag   1020
tttggggagt acaggtgtga gaaggaggac gacctggctg agctggcctc ccagcagtac   1080
tttgtagact atggctctga gatgatcctg gagcgcctcc tgaacctcgt gcccacctac   1140
atccccgacc gcgagatcac gcccctgaag acgctggaga agtgggccca gctggccatc   1200
gccgcccaca agaaggggat ttatgcccag aggagaactg atgcccagaa ggtcaaagag   1260
gatgtggtca gttatgcccg cttcaagtgg cccttgctct tctccaggtt ttatgaagcc   1320
tacaaattct caggccccag tctccccaag aacgacgtca tcgtggccgt caactggacg   1380
ggtgtgtact ttgtggatga gcaggagcag gtacttctgg agctgtcctt cccagagatc   1440
atggccgtgt ccagcagcag ggagtgccgt gtctggctct cactgggctg ctctgatctt   1500
ggctgtgctg cgcctcactc aggctgggca ggactgaccc cggcggggcc ctgttctccg   1560
tgttggtcct gcaggggagc gaaaacgacg gcccccagct tcacgctggc caccatcaag   1620
ggggacgaat acaccttcac ctccagtaat gctgaggaca ttcgtgacct ggtggtcacc   1680
ttcctagagg ggctccggaa gagatctaag tatgttgtgg ccctgcagga taaccccaac   1740
cccgcaggcg aggagtcagg cttcctcagc tttgccaagg gagacctcat catcctggac   1800
catgacacgg gcgagcaggt catgaactcg ggctgggcca acggcatcaa tgagaggacc   1860
aagcagcgtg ggacttccc caccgactgt gtgtacgtca tgcccactgt caccatgcca   1920
cctcgtgaga ttgtggccct ggtcaccatg actcccgatc agaggcagga cgttgtccgg   1980
ctcttgcagc tgcgaacggc ggagcccgag gtgcgtgcca agccctacac gctggaggag   2040
ttttcctatg actacttcag gcccccaccc aagcacacgc tgagccgtgt catggtgtcc   2100
aaggcccgag gcaaggaccg gctgtggagc cacacgcggg aaccgctcaa gcaggcgctg   2160
ctcaagaagc tcctgggcag tgaggagctc tcgcaggagg cctgcctggc cttcattgct   2220
gtgctcaagt acatgggcga ctacccgtcc aagaggacac gctccgtcaa tgagctcacc   2280
gaccagatct ttgagggtcc cctgaaagcc gagcccctga aggacgaggc atatgtgcag   2340
atcctgaagc agctgaccga caaccacatc aggtacagcg aggagcgggg ttgggagctg   2400
ctctggctgt gcacgggcct tttcccaccc agcaacatcc tcctgcccca cgtgcagcgc   2460
ttcctgcagt cccgaaagca ctgcccactc gccatcgact gcctgcaacg gctccagaaa   2520
gccctgagaa acgggtcccg gaagtaccct ccgcacctgg tggaggtgga ggccatccag   2580
cacaagacca cccagatttt ccacaaggtc tacttccctg atgacactga cgaggccttc   2640
gaagtggagt ccagcaccaa ggccaaggac ttctgccaga acatcgccac caggctgctc   2700
ctcaagtcct cagagggatt cagcctcttt gtcaaaattg cagacaaggt catcagcgtt   2760
cctgagaatg acttcttctt tgactttgtt cgacacttga cagactggat aaagaaagct   2820
cggcccatca aggacggaat tgtgccctca ctcacctacc aggtgttctt catgaagaag   2880
ctgtggacca ccacggtgcc agggaaggat cccatggccg attccatctt ccactattac   2940
```

caggagttgc ccaagtatct ccgaggctac cacaagtgca cgcgggagga ggtgctgcag 3000
ctgggggcgc tgatctacag ggtcaagttc gaggaggaca agtcctactt ccccagcatc 3060
cccaagctgc tgcgggagct ggtgccccag gaccttatcc ggcaggtctc acctgatgac 3120
tggaagcggt ccatcgtcgc ctacttcaac aagcacgcag ggaagtccaa ggaggaggcc 3180
aagctggcct tcctgaagct catcttcaag tggcccacct ttggctcagc cttcttcgag 3240
gtgaagcaaa ctacggagcc aaacttccct gagatcctcc taattgccat caacaagtat 3300
ggggtcagcc tcatcgatcc caaaacgaag gatatcctca ccactcatcc cttcaccaag 3360
atctccaact ggagcagcgg caacacctac ttccacatca ccattgggaa cttggtgcgc 3420
gggagcaaac tgctctgcga gacgtcactg ggctacaaga tggatgacct cctgacttcc 3480
tacattagcc agatgctcac agccatgagc aaacagcggg gctccaggag cggcaagtga 3540

<210> SEQ ID NO 25
<211> LENGTH: 215
<212> TYPE: DNA
<213> ORGANISM: Artificial Sequence
<220> FEATURE:
<223> OTHER INFORMATION: synthetic

<400> SEQUENCE: 25
gcctcgactg tgccttctag ttgccagcca tctgttgttt gcccctcccc cgtgccttcc 60
ttgaccctgg aaggtgccac tcccactgtc ctttcctaat aaaatgagga aattgcatcg 120
cattgtctga gtaggtgtca ttctattctg gggggtgggg tggggcagga cagcaagggg 180
gaggattggg aagacaatag caggcatgct gggga 215

<210> SEQ ID NO 26
<211> LENGTH: 4389
<212> TYPE: DNA
<213> ORGANISM: Artificial Sequence
<220> FEATURE:
<223> OTHER INFORMATION: synthetic

<400> SEQUENCE: 26
ctgcgcgctc gctcgctcac tgaggccgcc cgggcaaagc ccgggcgtcg ggcgaccttt 60
ggtcgcccgg cctcagtgag cgagcgagcg cgcagagagg gagtggccaa ctccatcact 120
aggggttcct tgtagttaat gattaacccg ccatgctact tatctacgta gccatgctct 180
aggaagatcg gaattcgccc tttgatcagg gattttgccg atttcggcct attggttaaa 240
aaatgagctg atttaacaaa aatttaacgc gaattttaac aaaatattaa cgtttataat 300
ttcaggtggc atctttcgat aggcacctat tggtcttact gacatccact ttgcctttct 360
ctccacaggc agccctggcg gtctggatca ccatcctccg cttcatgggg gacctccctg 420
agcccaagta ccacacagcc atgagtgatg gcagtgagaa gatccctgtg atgaccaaga 480
tttatgagac cctgggcaag aagacgtaca agagggagct gcaggccctg cagggcgagg 540
gcgaggccca gctccccgag ggccagaaga agagcagtgt gaggcacaag ctggtgcatt 600
tgactctgaa aaagaagtcc aagctcacag aggaggtgac caagaggctg catgacgggg 660
agtccacagt gcagggcaac agcatgctgg aggaccggcc cacctccaac ctggagaagc 720
tgcacttcat catcggcaat ggcatcctgc ggccagcact ccgggacgag atctactgcc 780
agatcagcaa gcagctgacc cacaacccct ccaagagcag ctatgcccgg ggctggattc 840
tcgtgtctct ctgcgtgggc tgtttcgccc cctccgagaa gtttgtcaag tacctgcgga 900

```
acttcatcca cgggggcccg cccggctacg ccccgtactg tgaggagcgc ctgagaagga    960
cctttgtcaa tgggacacgg acacagccgc ccagctggct ggagctgcag gccaccaagt   1020
ccaagaagcc aatcatgttg cccgtgacat tcatggatgg gaccaccaag accctgctga   1080
cggactcggc aaccacggcc aaggagctct gcaacgcgct ggccgacaag atctctctca   1140
aggaccggtt cgggttctcc ctctacattg ccctgtttga caaggtgtcc tccctgggca   1200
gcggcagtga ccacgtcatg gacgccatct cccagtgcga gcagtacgcc aaggagcagg   1260
gcgcccagga gcgcaacgcc ccctggaggc tcttcttccg caaagaggtc ttcacgccct   1320
ggcacagccc ctccgaggac aacgtggcca ccaacctcat ctaccagcag gtggtgcgag   1380
gagtcaagtt tggggagtac aggtgtgaga aggaggacga cctggctgag ctggcctccc   1440
agcagtactt tgtagactat ggctctgaga tgatcctgga gcgcctcctg aacctcgtgc   1500
ccacctacat ccccgaccgc gagatcacgc ccctgaagac gctggagaag tgggcccagc   1560
tggccatcgc cgcccacaag aaggggattt atgcccagag gagaactgat gcccagaagg   1620
tcaaagagga tgtggtcagt tatgcccgct tcaagtggcc cttgctcttc tccaggtttt   1680
atgaagccta caaattctca ggccccagtc tccccaagaa cgacgtcatc gtggccgtca   1740
actggacggg tgtgtacttt gtggatgagc aggagcaggt acttctggag ctgtccttcc   1800
cagagatcat ggccgtgtcc agcagcaggg agtgccgtgt ctggctctca ctgggctgct   1860
ctgatcttgg ctgtgctgcg cctcactcag gctgggcagg actgaccccg gcggggccct   1920
gttctccgtg ttggtcctgc aggggagcga aaacgacggc ccccagcttc acgctggcca   1980
ccatcaaggg ggacgaatac accttcacct ccagtaatgc tgaggacatt cgtgacctgg   2040
tggtcacctt cctagagggg ctccggaaga gatctaagta tgttgtggcc ctgcaggata   2100
accccaaccc cgcaggcgag gagtcaggct tcctcagctt tgccaaggga gacctcatca   2160
tcctggacca tgacacgggc gagcaggtca tgaactcggg ctgggccaac ggcatcaatg   2220
agaggaccaa gcagcgtggg gacttcccca ccgactgtgt gtacgtcatg cccactgtca   2280
ccatgccacc tcgtgagatt gtggccctgg tcaccatgac tcccgatcag aggcaggacg   2340
ttgtccggct cttgcagctg cgaacggcgg agcccgaggt gcgtgccaag ccctacacgc   2400
tggaggagtt ttcctatgac tacttcaggc ccccacccaa gcacacgctg agccgtgtca   2460
tggtgtccaa ggcccgaggc aaggaccggc tgtggagcca cacgcgggaa ccgctcaagc   2520
aggcgctgct caagaagctc ctgggcagtg aggagctctc gcaggaggcc tgcctggcct   2580
tcattgctgt gctcaagtac atgggcgact acccgtccaa gaggacacgc tccgtcaatg   2640
agctcaccga ccagatcttt gagggtcccc tgaaagccga gcccctgaag gacgaggcat   2700
atgtgcagat cctgaagcag ctgaccgaca accacatcag gtacagcgag gagcggggtt   2760
gggagctgct ctggctgtgc acgggccttt tcccacccag caacatcctc ctgccccacg   2820
tgcagcgctt cctgcagtcc cgaaagcact gcccactcgc catcgactgc ctgcaacggc   2880
tccagaaagc cctgagaaac gggtcccgga agtaccctcc gcacctggtg gaggtggagg   2940
ccatccagca caagaccacc cagattttcc acaaggtcta cttccctgat gacactgacg   3000
aggccttcga agtggagtcc agcaccaagg ccaaggactt ctgccagaac atcgccacca   3060
ggctgctcct caagtcctca gagggattca gcctctttgt caaaattgca gacaaggtca   3120
tcagcgttcc tgagaatgac ttcttctttg actttgttcg acacttgaca gactggataa   3180
agaaagctcg gcccatcaag gacggaattg tgccctcact cacctaccag gtgttcttca   3240
tgaagaagct gtggaccacc acggtgccag ggaaggatcc catggccgat tccatcttcc   3300
```

```
actattacca ggagttgccc aagtatctcc gaggctacca caagtgcacg cgggaggagg   3360

tgctgcagct gggggcgctg atctacaggg tcaagttcga ggaggacaag tcctacttcc   3420

ccagcatccc caagctgctg cgggagctgg tgccccagga ccttatccgg caggtctcac   3480

ctgatgactg gaagcggtcc atcgtcgcct acttcaacaa gcacgcaggg aagtccaagg   3540

aggaggccaa gctggccttc ctgaagctca tcttcaagtg gcccaccttt ggctcagcct   3600

tcttcgaggt gaagcaaact acggagccaa acttccctga gatcctccta attgccatca   3660

acaagtatgg ggtcagcctc atcgatccca aaacgaagga tatcctcacc actcatccct   3720

tcaccaagat ctccaactgg agcagcggca acacctactt ccacatcacc attgggaact   3780

tggtgcgcgg gagcaaactg ctctgcgaga cgtcactggg ctacaagatg gatgacctcc   3840

tgacttccta cattagccag atgctcacag ccatgagcaa acagcggggc tccaggagcg   3900

gcaagtgacc gcggcctgct gccggctctg cggcctcttc cgcgtcttcg agatctgcct   3960

cgactgtgcc ttctagttgc cagccatctg ttgtttgccc ctcccccgtg ccttccttga   4020

ccctggaagg tgccactccc actgtccttt cctaataaaa tgaggaaatt gcatcgcatt   4080

gtctgagtag gtgtcattct attctggggg gtggggtggg gcaggacagc aagggggagg   4140

attgggaaga caatagcagg catgctgggg actcgagtta agggcgcaat tcccgattag   4200

gatcttccta gagcatggct acgtagataa gtagcatggc gggttaatca ttaactacaa   4260

ggaaccccta gtgatggagt tggccactcc ctctctgcgc gctcgctcgc tcactgaggc   4320

cgggcgacca aaggtcgccc gacgcccggg ctttgcccgg gcggcctcag tgagcgagcg   4380

agcgcgcag                                                           4389
```

```
<210> SEQ ID NO 27
<211> LENGTH: 4468
<212> TYPE: DNA
<213> ORGANISM: Artificial Sequence
<220> FEATURE:
<223> OTHER INFORMATION: synthetic

<400> SEQUENCE: 27

ctgcgcgctc gctcgctcac tgaggccgcc cgggcaaagc ccgggcgtcg ggcgaccttt     60

ggtcgcccgg cctcagtgag cgagcgagcg cgcagagagg gagtggccaa ctccatcact    120

aggggttcct tgtagttaat gattaacccg ccatgctact tatctacgta gccatgctct    180

aggaagatcc taatcgggaa ttcgccctta agctagcgtg ccacctggtc gacattgatt    240

attgactagt tattaatagt aatcaattac ggggtcatta gttcatagcc catatatgga    300

gttccgcgtt acataactta cggtaaatgg cccgcctggc tgaccgccca acgacccccg    360

cccattgacg tcaataatga cgtatgttcc catagtaacg ccaataggga ctttccattg    420

acgtcaatgg gtggactatt tacggtaaac tgcccacttg gcagtacatc aagtgtatca    480

tatgccaagt acgcccccta ttgacgtcaa tgacggtaaa tggcccgcct ggcattatgc    540

ccagtacatg accttatggg actttcctac ttggcagtac atctacgtat tagtcatcgc    600

tattaccatg gtcgaggtg agccccacgt tctgcttcac tctccccatc tcccccccct    660

ccccaccccc aattttgtat ttatttattt tttaattatt ttgtgcagcg atgggggcgg    720

gggggggggg ggcgcgcgcc aggcggggcg gggcggggcg aggggcgggg cggggcgagg    780

cggagaggtg cggcggcagc caatcagagc ggcgcgctcc gaaagtttcc ttttatggcg    840

aggcggcggc ggcggcggcc ctataaaaag cgaagcgcgc ggcgggcggc tgcagaagtt    900
```

```
ggtcgtgagg cactgggcag gtaagtatca aggttacaag acaggtttaa ggagaccaat    960
agaaactggg cttgtcgaga cagagaagac tcttgcgttt ctgataggca cctattggtc   1020
ttactgacat ccactttgcc tttctctcca caggtgtcca ggcggccgcc atggtgattc   1080
ttcagcaggg ggaccatgtg tggatggacc tgagattggg gcaggagttc gacgtgccca   1140
tcggggcggt ggtgaagctc tgcgactctg ggcaggtcca ggtggtggat gatgaagaca   1200
atgaacactg gatctctccg cagaacgcaa cgcacatcaa gcctatgcac cccacgtcgg   1260
tccacggcgt ggaggacatg atccgcctgg gggacctcaa cgaggcgggc atcttgcgca   1320
acctgcttat ccgctaccgg gaccacctca tctacacgta tacgggctcc atcctggtgg   1380
ctgtgaaccc ctaccagctg ctctccatct actcgccaga gcacatccgc cagtatacca   1440
acaagaagat tggggagatg cccccccaca tctttgccat tgctgacaac tgctacttca   1500
acatgaaacg caacagccga gaccagtgct gcatcatcag tggggaatct ggggccggga   1560
agacggagag cacaaagctg atcctgcagt tcctggcagc catcagtggg cagcactcgt   1620
ggattgagca gcaggtcttg gaggccaccc ccattctgga agcatttggg aatgccaaga   1680
ccatccgcaa tgacaactca agccgtttcg gaaagtacat cgacatccac ttcaacaagc   1740
ggggcgccat cgagggcgcg aagattgagc agtacctgct ggaaaagtca cgtgtctgtc   1800
gccaggccct ggatgaaagg aactaccacg tgttctactg catgctggag ggcatgagtg   1860
aggatcagaa gaagaagctg ggcttgggcc aggcctctga ctacaactac ttggccatgg   1920
gtaactgcat aacctgtgag ggccgggtgg acagccagga gtacgccaac atccgctccg   1980
ccatgaaggt gctcatgttc actgacaccg agaactggga gatctcgaag ctcctggctg   2040
ccatcctgca cctgggcaac ctgcagtatg aggcacgcac atttgaaaac ctggatgcct   2100
gtgaggttct cttctcccca tcgctggcca cagctgcatc cctgcttgag gtgaaccccc   2160
cagacctgat gagctgcctg actagccgca ccctcatcac ccgcggggag acggtgtcca   2220
ccccactgag cagggaacag gcactggacg tgcgcgacgc cttcgtaaag gggatctacg   2280
ggcggctgtt cgtgtggatt gtggacaaga tcaacgcagc aatttacaag cctccctccc   2340
aggatgtgaa gaactctcgc aggtccatcg gcctcctgga catctttggg tttgagaact   2400
ttgctgtgaa cagctttgag cagctctgca tcaacttcgc caatgagcac ctgcagcagt   2460
tctttgtgcg gcacgtgttc aagctggagc aggaggaata tgacctggag agcattgact   2520
ggctgcacat cgagttcact gacaaccagg atgccctgga catgattgcc aacaagccca   2580
tgaacatcat ctccctcatc gatgaggaga gcaagttccc caagggcaca gacaccacca   2640
tgttacacaa gctgaactcc cagcacaagc tcaacgccaa ctacatcccc cccaagaaca   2700
accatgagac ccagtttggc atcaaccatt ttgcaggcat cgtctactat gagacccaag   2760
gcttcctgga gaagaaccga gacaccctgc atggggacat tatccagctg gtccactcct   2820
ccaggaacaa gttcatcaag cagatcttcc aggccgatgt cgccatgggc gccgagacca   2880
ggaagcgctc gcccacactt agcagccagt tcaagcggtc actggagctg ctgatgcgca   2940
cgctgggtgc ctgccagccc ttctttgtgc gatgcatcaa gcccaatgag ttcaagaagc   3000
ccatgctgtt cgaccggcac ctgtgcgtgc gccagctgcg gtactcagga atgatggaga   3060
ccatccgaat ccgccgagct ggctacccca tccgctacag cttcgtagag tttgtggagc   3120
ggtaccgtgt gctgctgcca ggtgtgaagc cggcctacaa gcagggcgac ctccgcggga   3180
cttgccagcg catggctgag gctgtgctgg gcacccacga tgactggcag ataggcaaaa   3240
ccaagatctt tctgaaggac caccatgaca tgctgctgga agtggagcgg gacaaagcca   3300
```

```
tcaccgacag agtcatcctc cttcagaaag tcatccgggg attcaaagac aggtctaact   3360

ttctgaagct gaagaacgct gccacactga tccagaggca ctggcggggt cacaactgta   3420

ggaagaacta cgggctgatg cgtctgggct tcctgcggct gcaggccctg caccgctccc   3480

ggaagctgca ccagcagtac cgcctggccc gccagcgcat catccagttc caggcccgct   3540

gccgcgccta tctggtgcgc aaggccttcc gccaccgcct ctgggctgtg ctcaccgtgc   3600

aggcctatgc ccggggcatg atcgcccgca ggctgcacca acgcctcagg gctgagtatc   3660

tgtggcgcct cgaggctgag aaaatgcggc tggcggagga agagaagctt cggaaggaga   3720

tgagcgccaa gaaggccaag gaggaggccg agcgcaagca tcaggagcgc ctggcccagc   3780

tggctcgtga ggacgctgag cgggagctga aggagaagga ggccgctcgg cggaagaagg   3840

agctcctgga gcagatggaa agggcccgcc atgagcctgt caatcactca gacatggtgg   3900

acaagatgtt tggcttcctg gggacttcag gtggcctgcc aggccaggag ggccaggcac   3960

ctagtggctt tgaggacctg gagcgagggc ggagggagat ggtggaggag gacctggatg   4020

cagccctgcc cctgcctgac gaggatgagg aggacctctc tgagtataaa tttgccaagt   4080

tcgcggccac ctacttccag gggacaacta cgcactccta cacccggcgg ccactcaaac   4140

agccactgct ctaccatgac gacgagggtg accagctggt aagtatcaag gttacaagac   4200

aggtttaagg agaccaatag aaactgggct tgtcgagaca gagaagactc ttgcgtttct   4260

caattgaagg gcgaattccg atcttcctag agcatggcta cgtagataag tagcatggcg   4320

ggttaatcat taactacaag gaacccctag tgatggagtt ggccactccc tctctgcgcg   4380

ctcgctcgct cactgaggcc gggcgaccaa aggtcgcccg acgcccgggc tttgcccggg   4440

cggcctcagt gagcgagcga gcgcgcag                                      4468
```

<210> SEQ ID NO 28
<211> LENGTH: 4268
<212> TYPE: DNA
<213> ORGANISM: Artificial Sequence
<220> FEATURE:
<223> OTHER INFORMATION: synthetic

<400> SEQUENCE: 28

```
ctgcgcgctc gctcgctcac tgaggccgcc cgggcaaagc ccgggcgtcg ggcgaccttt     60

ggtcgcccgg cctcagtgag cgagcgagcg cgcagagagg gagtggccaa ctccatcact    120

aggggttcct tgtagttaat gattaacccg ccatgctact tatctacgta gccatgctct    180

aggaagatcg gaattcgata ggcacctatt ggtcttactg acatccactt tgcctttctc    240

tccacaggca gccctggcgg tctggatcac catcctccgc ttcatggggg acctccctga    300

gcccaagtac cacacagcca tgagtgatgg cagtgagaag atccctgtga tgaccaagat    360

ttatgagacc ctgggcaaga agacgtacaa gagggagctg caggccctgc agggcgaggg    420

cgaggcccag ctccccgagg gccagaagaa gagcagtgtg aggcacaagc tggtgcattt    480

gactctgaaa aagaagtcca agctcacaga ggaggtgacc aagaggctgc atgacgggga    540

gtccacagtg cagggcaaca gcatgctgga ggaccggccc acctccaacc tggagaagct    600

gcacttcatc atcggcaatg gcatcctgcg gccagcactc cgggacgaga tctactgcca    660

gatcagcaag cagctgaccc acaacccctc caagagcagc tatgcccggg gctggattct    720

cgtgtctctc tgcgtgggct gtttcgcccc ctccgagaag tttgtcaagt acctgcggaa    780

cttcatccac gggggcccgc ccggctacgc cccgtactgt gaggagcgcc tgagaaggac    840
```

-continued

```
ctttgtcaat gggacacgga cacagccgcc cagctggctg gagctgcagg ccaccaagtc    900
caagaagcca atcatgttgc ccgtgacatt catggatggg accaccaaga ccctgctgac    960
ggactcggca accacggcca aggagctctg caacgcgctg gccgacaaga tctctctcaa   1020
ggaccggttc gggttctccc tctacattgc cctgtttgac aaggtgtcct ccctgggcag   1080
cggcagtgac cacgtcatgg acgccatctc ccagtgcgag cagtacgcca aggagcaggg   1140
cgcccaggag cgcaacgccc cctggaggct cttcttccgc aaagaggtct tcacgccctg   1200
gcacagcccc tccgaggaca acgtggccac caacctcatc taccagcagg tggtgcgagg   1260
agtcaagttt ggggagtaca ggtgtgagaa ggaggacgac ctggctgagc tggcctccca   1320
gcagtacttt gtagactatg gctctgagat gatcctggag cgcctcctga acctcgtgcc   1380
cacctacatc cccgaccgcg agatcacgcc cctgaagacg ctggagaagt gggcccagct   1440
ggccatcgcc gcccacaaga aggggattta tgcccagagg agaactgatg cccagaaggt   1500
caaagaggat gtggtcagtt atgcccgctt caagtggccc ttgctcttct ccaggtttta   1560
tgaagcctac aaattctcag gccccagtct ccccaagaac gacgtcatcg tggccgtcaa   1620
ctggacgggt gtgtactttg tggatgagca ggagcaggta cttctggagc tgtccttccc   1680
agagatcatg gccgtgtcca gcagcaggga gtgccgtgtc tggctctcac tgggctgctc   1740
tgatcttggc tgtgctgcgc ctcactcagg ctgggcagga ctgaccccgg cggggccctg   1800
ttctccgtgt tggtcctgca ggggagcgaa aacgacggcc cccagcttca cgctggccac   1860
catcaagggg gacgaataca ccttcacctc cagtaatgct gaggacattc gtgacctggt   1920
ggtcaccttc ctagaggggc tccggaagag atctaagtat gttgtggccc tgcaggataa   1980
ccccaacccc gcaggcgagg agtcaggctt cctcagcttt gccaagggag acctcatcat   2040
cctggaccat gacacgggcg agcaggtcat gaactcgggc tgggccaacg gcatcaatga   2100
gaggaccaag cagcgtgggg acttccccac cgactgtgtg tacgtcatgc ccactgtcac   2160
catgccacct cgtgagattg tggccctggt caccatgact cccgatcaga ggcaggacgt   2220
tgtccggctc ttgcagctgc gaacggcgga gcccgaggtg cgtgccaagc cctacacgct   2280
ggaggagttt tcctatgact acttcaggcc cccacccaag cacacgctga gccgtgtcat   2340
ggtgtccaag gcccgaggca aggaccggct gtggagccac acgcgggaac cgctcaagca   2400
ggcgctgctc aagaagctcc tgggcagtga ggagctctcg caggaggcct gcctggcctt   2460
cattgctgtg ctcaagtaca tgggcgacta cccgtccaag aggacacgct ccgtcaatga   2520
gctcaccgac cagatctttg agggtcccct gaaagccgag cccctgaagg acgaggcata   2580
tgtgcagatc ctgaagcagc tgaccgacaa ccacatcagg tacagcgagg agcggggttg   2640
ggagctgctc tggctgtgca cgggcctttt cccacccagc aacatcctcc tgccccacgt   2700
gcagcgcttc ctgcagtccc gaaagcactg cccactcgcc atcgactgcc tgcaacggct   2760
ccagaaagcc ctgagaaacg ggtcccggaa gtaccctccg cacctggtgg aggtggaggc   2820
catccagcac aagaccaccc agattttcca caaggtctac ttccctgatg acactgacga   2880
ggccttcgaa gtggagtcca gcaccaaggc caaggacttc tgccagaaca tcgccaccag   2940
gctgctcctc aagtcctcag agggattcag cctctttgtc aaaattgcag acaaggtcat   3000
cagcgttcct gagaatgact tcttctttga ctttgttcga cacttgacag actggataaa   3060
gaaagctcgg cccatcaagg acggaattgt gccctcactc acctaccagg tgttcttcat   3120
gaagaagctg tggaccacca cggtgccagg gaaggatccc atggccgatt ccatcttcca   3180
ctattaccag gagttgccca agtatctccg aggctaccac aagtgcacgc gggaggaggt   3240
```

gctgcagctg ggggcgctga tctacagggt caagttcgag gaggacaagt cctacttccc 3300
cagcatcccc aagctgctgc gggagctggt gccccaggac cttatccggc aggtctcacc 3360
tgatgactgg aagcggtcca tcgtcgccta cttcaacaag cacgcaggga agtccaagga 3420
ggaggccaag ctggccttcc tgaagctcat cttcaagtgg cccacctttg gctcagcctt 3480
cttcgaggtg aagcaaacta cggagccaaa cttccctgag atcctcctaa ttgccatcaa 3540
caagtatggg gtcagcctca tcgatcccaa aacgaaggat atcctcacca ctcatccctt 3600
caccaagatc tccaactgga gcagcggcaa cacctacttc cacatcacca ttgggaactt 3660
ggtgcgcggg agcaaactgc tctgcgagac gtcactgggc tacaagatgg atgacctcct 3720
gacttcctac attagccaga tgctcacagc catgagcaaa cagcggggct ccaggagcgg 3780
caagtgaccg cggcctgctg ccggctctgc ggcctcttcc gcgtcttcga gatctgcctc 3840
gactgtgcct tctagttgcc agccatctgt tgtttgcccc tcccccgtgc cttccttgac 3900
cctggaaggt gccactccca ctgtcctttc ctaataaaat gaggaaattg catcgcattg 3960
tctgagtagg tgtcattcta ttctgggggg tggggtgggg caggacagca agggggagga 4020
ttgggaagac aatagcaggc atgctgggga ctcgagttaa gggcgcaatt cccgattagg 4080
atcttcctag agcatggcta cgtagataag tagcatggcg ggttaatcat taactacaag 4140
gaacccctag tgatggagtt ggccactccc tctctgcgcg ctcgctcgct cactgaggcc 4200
gggcgaccaa aggtcgcccg acgcccgggc tttgcccggg cggcctcagt gagcgagcga 4260
gcgcgcag 4268

<210> SEQ ID NO 29
<211> LENGTH: 278
<212> TYPE: DNA
<213> ORGANISM: Artificial Sequence
<220> FEATURE:
<223> OTHER INFORMATION: synthetic

<400> SEQUENCE: 29
gtgatcctag gtggaggccg aaagtacatg tttcgcatgg gaaccccaga ccctgagtac 60
ccagatgact acagccaagg tgggaccagg ctggacggga agaatctggt gcaggaatgg 120
ctggcgaagc gccagggtgc ccggtacgtg tggaaccgca ctgagctcat gcaggcttcc 180
ctggacccgt ctgtgaccca tctcatgggt ctctttgagc ctggagacat gaaatacgag 240
atccaccgag actccacact ggacccctcc ctgatgga 278

<210> SEQ ID NO 30
<211> LENGTH: 66
<212> TYPE: DNA
<213> ORGANISM: Artificial Sequence
<220> FEATURE:
<223> OTHER INFORMATION: synthetic

<400> SEQUENCE: 30
gactacaaag accatgacgg tgattataaa gatcatgaca tcgactacaa ggatgacgat 60
gacaag 66

<210> SEQ ID NO 31
<211> LENGTH: 30
<212> TYPE: DNA
<213> ORGANISM: Artificial Sequence -continued

```
<220> FEATURE:
<223> OTHER INFORMATION: synthetic

<400> SEQUENCE: 31

atgtatgatg ttcctgatta tgctagcctc                                    30
```

EFFECTIVE DELIVERY OF LARGE GENES BY DUAL AAV VECTORS

CROSS-REFERENCE TO RELATED APPLICATIONS

This application is a 371 of PCT/EP2014/058000 filed on Apr. 18, 2014 which claims the benefit of priority from U.S. 61/813,342 filed on Apr. 18, 2013.

STATEMENT OF FUNDING

This invention was made with the support of the Italian Telethon Foundation (grant TGM11MT1 and European funds). The Italian Telethon Foundation has rights in this invention.

Studies on the dual AAV trans-splicing and dual AAV hybrid AP strategies were made with U.S. Government support under Contract No. R24RY019861 awarded by the National Eye Institute. The U.S. Government has certain rights in this invention.

TECHNICAL FIELD

The present invention relates to constructs, vectors, relative host cells and pharmaceutical compositions which allow an effective gene therapy, in particular of genes larger than 5 Kb.

BACKGROUND OF THE INVENTION

Inherited retinal degenerations (IRDs), with an overall global prevalence of ½,000 (1), are a major cause of blindness worldwide. Among the most frequent and severe IRDs are retinitis pigmentosa (RP), Leber congenital amaurosis (LCA), and Stargardt disease (STGD), which are most often inherited as monogenic conditions. The majority of mutations causing IRDs occur in genes expressed in neuronal photoreceptors (PR), rods and/or cones in the retina (2). No therapy is currently available for these blinding diseases.

Gene therapy holds great promise for the treatment of IRDs. Among the available gene transfer vectors, those based on the small adeno-associated virus (AAV) are most efficient at targeting both PR and retinal pigment epithelium (RPE) (3-4) for long-term treatment upon a single subretinal administration (3-4). Recently the inventors and others, have demonstrated that subretinal administration of AAV is well-tolerated and effective for improving vision in patients affected with type 2 LCA, which is caused by mutations in RPE65, a gene expressed in the RPE (5-9). These results bode well for the treatment of other forms of LCA and IRDs in general. The availability of AAV vector serotypes such as AAV2/8, which efficiently targets PR (10-14) and RPE, further supports this approach. However, a major limitation of AAV is its cargo capacity, which is thought to be limited to around 5 kb, the size of the parental viral genome (15-19). This limits the application of AAV gene therapy approaches for common IRDs that are caused by mutations in genes whose coding sequence (CDS) is larger than 5 kb (herein referred to as large genes). These include:

| DISEASE | GENE | CDS | EXPRESSION |
|---|---|---|---|
| Stargardt Disease | ABCA4 | 6.8 Kb | rod&cone PRs |
| Usher 1B | MYO7A | 6.7 Kb | RPE and PRs |
| Leber Congenital Amaurosis10 | CEP290 | 7.5 Kb | mainly PRs (pan retinal) |
| Usher1D, Nonsyndromic deafness, autosomal recessive (DFNB12) | CDH23 | 10.1 Kb | PRs |
| Retinitis Pigmentosa | EYS | 9.4 Kb | PR ECM |
| Usher 2A | USH2a | 15.6 Kb | rod&cone PRs |
| Usher 2C | GPR98 | 18.0 Kb | mainly PRs |
| Alstrom Syndrome | ALMS1 | 12.5 Kb | rod&cone PRs |

Stargardt disease (STGD; MIM#248200) is the most common form of inherited macular degeneration caused by mutations in the ABCA4 gene (CDS: 6822 bp), which encodes the all-trans retinal transporter located in the PR outer segment (20); Usher syndrome type IB (USH1B; MIM#276900) is the most severe form of RP and deafness caused by mutations in the MYO7A gene (CDS: 6648 bp) (21) encoding the unconventional MYO7A, an actin-based motor expressed in both PR and RPE within the retina (22-24).

Cone-rod dystrophy type 3, fundus flavimaculatus, age-related macular degeneration type 2, Early-onset severe retinal dystrophy, and Retinitis pigmentosa type 19 are also associated with ABCA4 mutations (ABCA4-associated diseases).

Various strategies have been investigated to overcome the limitation of AAV cargo capacity. Several groups, including the inventors' own, have attempted to "force" large genes into one of the many AAV caspids available by developing the so-called oversize vectors (25-27). Although administration of oversize AAV vectors achieves therapeutically-relevant levels of transgene expression in rodent and canine models of human inherited diseases (27-30), including the retina of the Abca4−/− and shaker 1 (sh1) mouse models of STGD and USH1B (27, 30), the mechanism underlying oversize AAV-mediated transduction remains elusive. In contrast to what the inventors and others originally proposed (25-27), oversize AAV vectors do not contain a pure population of intact large size genomes but rather a heterogeneous mixture of mostly truncated genomes≤5 kb in length (15-18). Following infection, reassembly of these truncated genomes in the target cell nucleus has been proposed as a mechanism for oversize AAV vector transduction (15-17, 31). Independent of transduction mechanism and in vivo efficacy, the heterogeneity in oversize AAV genome sizes is a major limitation for their application in human gene therapy.

Alternatively, the inherent ability of AAV genomes to undergo intermolecular concatemerization (32) is exploited to transfer large genes in vivo by splitting a large gene expression cassette into halves (<5 kb in size), each contained in one of two separate (dual) AAV vectors (33-35). In the dual AAV trans-splicing strategy, a splice donor (SD) signal is placed at the 3' end of the 5'-half vector and a splice acceptor (SA) signal is placed at the 5' end of the 3'-half vector. Upon co-infection of the same cell by the dual AAV vectors and inverted terminal repeat (ITR)-mediated head-to-tail concatemerization of the two halves, trans-splicing results in the production of a mature mRNA and full-size protein (33). Trans-splicing has been successfully used to express large genes in muscle and retina (36-37).

In particular, Reich et al. (37) used the trans-splicing strategy with AAV2 and AAV5 capsids and show that both vectors transduce both retinal pigment epithelium and photoreceptors using LacZ gene as a reporter gene. This strategy was not employed using a therapeutic and/or large gene.

Alternatively, the two halves of a large transgene expression cassette contained in dual AAV vectors may contain homologous overlapping sequences (at the 3' end of the 5'-half vector and at the 5' end of the 3'-half vector, dual AAV overlapping), which will mediate reconstitution of a single large genome by homologous recombination (34). This strategy depends on the recombinogenic properties of the transgene overlapping sequences (38). A third dual AAV strategy (hybrid) is based on adding a highly recombinogenic region from an exogenous gene [i.e. alkaline phosphatase, AP (35, 39)] to the trans-splicing vector. The added region is placed downstream of the SD signal in the 5'-half vector and upstream of the SA signal in the 3'-half vector in order to increase recombination between the dual AAVs. The document US2010/003218 is directed to an AP-based hybrid dual vector system. The document shows the transduction efficiency of the AP-based hybrid dual vector expressing mini-dystrophin but no data concerning efficacy.

Lopes et al. (30) studied retinal gene therapy with a large MYO7A cDNA using adeno-associated virus and found that MYO7A therapy with AAV2 or AAV5 single vectors is efficacious to some extent, while the dual AAV2 approach proved to be less effective.

Therefore there is still the need for constructs and vectors that can be exploited to reconstitute large gene expression for an effective gene therapy.

SUMMARY OF THE INVENTION

Retinal gene therapy with adeno-associated viral (AAV) vectors is safe and effective in humans. However, AAV cargo capacity limited to 5 kb prevents it from being applied to therapies of those inherited retinal diseases, such as Stargardt disease (STGD) or Usher syndrome type IB (USH1B) that are due to mutations of genes exceeding 5 kb. Previous methods for large gene transfer tested in the retina and based on “forced” packaging of large genes into AAV capsids (oversize AAV) may not be easily translated to the clinical arena due to the heterogeneity of vector genome size, which represents a safety concern.

Taking advantage of AAV ability to undergo intermolecular concatemerization, the inventors generated dual AAV vectors which reconstitute a large gene by either splicing (trans-splicing), homologous recombination (overlapping), or a combination of the two (hybrid).

To determine which AAV-based strategy most efficiently transduces large genes in the retina, the inventors compared several AAV-based strategies side-by-side in HEK293 cells and in mouse and pig retina in vivo using EGFP, ABCA4 or MYO7A.

The inventors found that dual trans-splicing and hybrid but not overlapping AAV vectors transduce efficiently mouse and pig photoreceptors, the major cell target for treatment of inherited retinal degenerations. The levels of retinal transduction by dual trans-splicing or hybrid AAV resulted in a significant improvement of the phenotype of Abca4−/− and sh1 mouse models of STGD and USH1B. Dual AAV trans-splicing or hybrid vectors are an attractive strategy for gene therapy of retinal diseases that require delivery of large genes.

It is therefore an embodiment of the present invention a dual construct system to express the coding sequence of a gene of interest in an host cell, said coding sequence consisting of a 5' end portion and of a 3' end portion, comprising:

a) a first plasmid comprising in a 5'-3' direction:
a 5'-inverted terminal repeat (5'-ITR) sequence;
a promoter sequence;
the 5' end portion of said coding sequence, said 5'end portion being operably linked to and under control of said promoter;
a nucleic acid sequence of a splicing donor signal; and
a 3'-inverted terminal repeat (3'-ITR) sequence; and
b) a second plasmid comprising in a 5'-3' direction:
a 5'-inverted terminal repeat (5'-ITR) sequence;
a nucleic acid sequence of a splicing acceptor signal;
the 3'end of said coding sequence;
a poly-adenylation signal nucleic acid sequence; and
a 3'-inverted terminal repeat (3'-ITR) sequence.

A preferred embodiment of the present invention is a dual construct system to express the coding sequence of a gene of interest in an host cell, said coding sequence consisting of a 5'end portion and of a 3' end portion, comprising:

a) a first plasmid comprising in a 5'-3' direction:
a 5'-inverted terminal repeat (5'-ITR) sequence;
a promoter sequence;
the 5' end portion of said coding sequence, said 5'end portion being operably linked to and under control of said promoter;
a nucleic acid sequence of a splicing donor signal; and
a 3'-inverted terminal repeat (3'-ITR) sequence; and
b) a second plasmid comprising in a 5'-3' direction:
a 5'-inverted terminal repeat (5'-ITR) sequence;
a nucleic acid sequence of a splicing acceptor signal;
the 3'end of said coding sequence;
a poly-adenylation signal nucleic acid sequence; and
a 3'-inverted terminal repeat (3'-ITR) sequence, wherein upon introduction of said first plasmid and said second plasmid into the host cell, said coding sequence reconstitutes by means of the splicing donor and the splicing acceptor signals. The dual construct system of the present invention is advantageously exploited to reconstitute large gene expression. When the coding sequence reconstitutes, gene expression occurs.

Preferably, said first plasmid and said second plasmid further comprise a nucleic acid sequence of a recombinogenic region in 5' position of the 3'ITR and in 3' position of the 5'-ITR, respectively.

More preferably, the recombinogenic region is a F1 phage recombinogenic region.

Still preferably the nucleic acid sequence of a recombinogenic region consists essentially of the sequence:

```
                                        (SEQ ID NO. 3)
GGGATTTTGCCGATTTCGGCCTATTGGTTAAAAAATGAGCTGATTTAACA

AAAATTTAACGCGAATTTTAACAAAAT.
```

The recombinogenic region may also be a fragment of SEQ ID NO. 3, said fragment maintaining the recombinogenic properties of the full length sequence. Preferably the fragment has 70%, 75%, 80%, 85%, 90%, 95% or 99% identity with SEQ ID NO. 3.

Still preferably, the nucleotide sequence of the ITRs derives from the same or different AAV serotype.

Preferably, the 3'-ITR of the first plasmid and the 5'-ITR of the second plasmid are from the same AAV serotype.

Yet preferably, the 5'-ITR and 3'-ITR of the first plasmid and the 5'-ITR and 3'-ITR of the second plasmid are respectively from different AAV serotypes.

Preferably, the 5'-ITR of the first plasmid and the 3'-ITR of the second plasmid are from different AAV serotypes.

Yet preferably the coding sequence is split into the 5' end portion and the 3' end portion at a natural exon-exon junction.

In a preferred embodiment the nucleic acid sequence of the splicing donor signal consists essentially of the sequence:

```
                                        (SEQ ID No. 1)
GTAAGTATCAAGGTTACAAGACAGGTTTAAGGAGACCAATAGAAACTGGG

CTTGTCGAGACAGAGAAGACTCTTGCGTTTCT.
```

In a preferred embodiment the nucleic acid sequence of the splicing acceptor signal consists essentially of the sequence:

```
                                        (SEQ ID No. 2)
GATAGGCACCTATTGGTCTTACTGACATCCACTTTGCCTTTCTCTCCACA

G.
```

The spicing acceptor signal and the splicing donor signal may also be chosen by the skilled person in the art among sequences known in the art.

Spliceosomal introns often reside within the sequence of eukaryotic protein-coding genes. Within the intron, a donor site (5' end of the intron), a branch site (near the 3' end of the intron) and an acceptor site (3' end of the intron) are required for splicing. The splice donor site includes an almost invariant sequence GU at the 5' end of the intron, within a larger, less highly conserved region. The splice acceptor site at the 3' end of the intron terminates the intron with an almost invariant AG sequence. Upstream (5'-ward) from the AG there is a region high in pyrimidines (C and U), or polypyrimidine tract. Upstream from the polypyrimidine tract is the branchpoint, which includes an adenine nucleotide.

In a preferred embodiment the first plasmid further comprises at least one enhancer sequence, operably linked to the coding sequence. Any known suitable enhancer sequence may be selected by the skilled person in the art.

Preferably the coding sequence is a nucleotide sequence encoding a protein able to correct a genetic disease, in particular an inherited retinal degeneration.

Still preferably the coding sequence is selected from the group consisting of: ABCA4, MYO7A, CEP290, CDH23, EYS, USH2a, GPR98 or ALMS1.

It is a further embodiment of the invention a dual viral vector system comprising:

a) a first viral vector containing the first plasmid comprising in a 5'-3' direction: a 5'-inverted terminal repeat (5'-ITR) sequence, a promoter sequence, the 5' end portion of said coding sequence, said 5'end portion being operably linked to and under control of said promoter, a nucleic acid sequence of a splicing donor signal, and a 3'-inverted terminal repeat (3'-ITR) sequence; and b) a second viral vector containing the second plasmid comprising in a 5'-3' direction: a 5'-inverted terminal repeat (5'-ITR) sequence, a nucleic acid sequence of a splicing acceptor signal, the 3'end of said coding sequence, a poly-adenylation signal nucleic acid sequence; and a 3'-inverted terminal repeat (3'-ITR) sequence.

Preferably the vectors are adeno-associated virus (AAV) vectors.

Still preferably the adeno-associated virus (AAV) vectors are selected from the same or different AAV serotypes.

Still preferably the adeno-associated virus is selected from the serotype 2, the serotype 8, the serotype 5, the serotype 7 or the serotype 9.

It is a further embodiment of the invention a host cell transformed with the dual viral vector system according to the invention.

Preferably the host cell is a mammalian cell, a human cell, a retinal cell, a non-embryonic stem cell.

It is a further embodiment of the invention the dual construct system of the invention, the dual viral vector system of the invention or the host cell of the invention for medical use, preferably for use in a gene therapy, still preferably for the treatment and/or prevention of a pathology or disease characterized by a retinal degeneration. Preferably, the retinal degeneration is inherited.

Still preferably the pathology or disease is selected from the group consisting of: retinitis pigmentosa, Leber congenital amaurosis (LCA), Stargardt disease, Usher disease, Alstrom syndrome, a disease caused by a mutation in the ABCA4 gene (also named a ABCA4-associated disease). Cone-rod dystrophy type 3, fundus flavimaculatus, age-related macular degeneration type 2, Early-onset severe retinal dystrophy, and Retinitis pigmentosa type 19 are examples of disease caused by a mutation in the ABCA4 gene (ABCA4-associated diseases).

It is a further embodiment of the invention a pharmaceutical composition comprising the dual construct system according to the invention, the dual viral vector system according to the invention or the host cell according to the invention and pharmaceutically acceptable vehicle.

It is a further embodiment of the invention a method for treating and/or preventing a pathology or disease characterized by a retinal degeneration comprising administering to a subject in need thereof an effective amount of the dual construct system as described herein, the dual viral vector system as described herein or the host cell as described herein.

It is a further embodiment of the invention a nucleic acid consisting of SEQ ID No. 3 for use as a recombinogenic region.

It is a further embodiment of the invention a method to induce genetic recombination comprising using the sequence consisting of SEQ ID No. 3.

In the present invention preferably the promoter is selected from the group consisting of: cytomegalovirus promoter, Rhodopsin promoter, Rhodopsin kinase promoter, Interphotoreceptor retinoid binding protein promoter, vitelliform macular dystrophy 2 promoter. However any suitable promoter known in the art may be used.

In the present invention, the coding sequence is split into a first and a second fragment (5' end portion and 3' end portion) at a natural exon-exon junction. Preferably each fragment of the coding sequence should not exceed a size of 10 kb. Preferably each 5' end portion and 3' end portion may have a size of 4.5 Kb, 5 Kb, 5.5 Kb, 6 Kb, 6.5 Kb, 7 kb, 7.5 Kb, 8 Kb, 8.5 Kb, 9 Kb, 9.5 Kb or a smaller size.

During the past decade, gene therapy has been applied to the treatment of disease in hundreds of clinical trials. Various tools have been developed to deliver genes into human cells; among them, genetically engineered viruses, including adenoviruses, are currently amongst the most popular tool for gene delivery. Most of the systems contain vectors that are capable of accommodating genes of interest and helper cells that can provide the viral structural proteins and enzymes to allow for the generation of vector-containing infectious viral particles. Adeno-associated virus is a family of viruses that differs in nucleotide and amino acid sequence, genome structure, pathogenicity, and host range. This diversity provides opportunities to use viruses with different biological characteristics to develop different therapeutic applications. As with any delivery tool, the efficiency, the ability to target certain tissue or cell type, the expression of the gene of interest, and the safety of adenoviral-based systems are important for successful application of gene therapy. Significant efforts have been dedicated to these areas of research in recent years. Various modifications have been made to Adeno-associated virus-based vectors and helper cells to alter gene expression, target delivery, improve viral titers, and increase safety. The present invention represents an improvement in this design process in that it acts to efficiently deliver genes of interest into such viral vectors. Viruses are logical tools for gene delivery. They replicate inside cells and therefore have evolved mechanisms to enter the cells and use the cellular machinery to express their genes. The concept of virus-based gene delivery is to engineer the virus so that it can express the gene of interest. Depending on the specific application and the type of virus, most viral vectors contain mutations that hamper their ability to replicate freely as wild-type viruses in the host. Viruses from several different families have been modified to generate viral vectors for gene delivery. These viruses include retroviruses, lentivirus, adenoviruses, adeno-associated viruses, herpes simplex viruses, picornaviruses, and alphaviruses. The present invention preferably employs adeno-associated viruses.

An ideal adeno-associated virus based vector for gene delivery must be efficient, cell-specific, regulated, and safe. The efficiency of delivery is important because it can determine the efficacy of the therapy. Current efforts are aimed at achieving cell-type-specific infection and gene expression with adeno-associated viral vectors. In addition, adeno-associated viral vectors are being developed to regulate the expression of the gene of interest, since the therapy may require long-lasting or regulated expression. Safety is a major issue for viral gene delivery because most viruses are either pathogens or have a pathogenic potential. It is important that during gene delivery, the patient does not also inadvertently receive a pathogenic virus that has full replication potential.

Adeno-associated virus (AAV) is a small virus which infects humans and some other primate species. AAV is not currently known to cause disease and consequently the virus causes a very mild immune response. Gene therapy vectors using AAV can infect both dividing and quiescent cells and persist in an extrachromosomal state without integrating into the genome of the host cell. These features make AAV a very attractive candidate for creating viral vectors for gene therapy, and for the creation of isogenic human disease models.

Wild-type AAV has attracted considerable interest from gene therapy researchers due to a number of features. Chief amongst these is the virus's apparent lack of pathogenicity. It can also infect non-dividing cells and has the ability to stably integrate into the host cell genome at a specific site (designated AAVS1) in the human chromosome 19. The feature makes it somewhat more predictable than retroviruses, which present the threat of a random insertion and of mutagenesis, which is sometimes followed by development of a cancer. The AAV genome integrates most frequently into the site mentioned, while random incorporations into the genome take place with a negligible frequency. Development of AAVs as gene therapy vectors, however, has eliminated this integrative capacity by removal of the rep and cap from the DNA of the vector. The desired gene together with a promoter to drive transcription of the gene is inserted between the inverted terminal repeats (ITR) that aid in concatamer formation in the nucleus after the single-stranded vector DNA is converted by host cell DNA polymerase complexes into double-stranded DNA. AAV-based gene therapy vectors form episomal concatamers in the host cell nucleus. In non-dividing cells, these concatemers remain intact for the life of the host cell. In dividing cells, AAV DNA is lost through cell division, since the episomal DNA is not replicated along with the host cell DNA. Random integration of AAV DNA into the host genome is detectable but occurs at very low frequency. AAVs also present very low immunogenicity, seemingly restricted to generation of neutralizing antibodies, while they induce no clearly defined cytotoxic response. This feature, along with the ability to infect quiescent cells present their dominance over adenoviruses as vectors for the human gene therapy.

AAV Genome, Transcriptome and Proteome

The AAV genome is built of single-stranded deoxyribonucleic acid (ssDNA), either positive- or negative-sensed, which is about 4.7 kilobase long. The genome comprises inverted terminal repeats (ITRs) at both ends of the DNA strand, and two open reading frames (ORFs): rep and cap. The former is composed of four overlapping genes encoding Rep proteins required for the AAV life cycle, and the latter contains overlapping nucleotide sequences of capsid proteins: VP1, VP2 and VP3, which interact together to form a capsid of an icosahedral symmetry.

ITR Sequences

The Inverted Terminal Repeat (ITR) sequences comprise 145 bases each. They were named so because of their symmetry, which was shown to be required for efficient multiplication of the AAV genome. Another property of these sequences is their ability to form a hairpin, which contributes to so-called self-priming that allows primase-independent synthesis of the second DNA strand. The ITRs were also shown to be required for both integration of the AAV DNA into the host cell genome (19th chromosome in humans) and rescue from it, as well as for efficient encapsidation of the AAV DNA combined with generation of a fully assembled, deoxyribonuclease-resistant AAV particles.

With regard to gene therapy, ITRs seem to be the only sequences required in cis next to the therapeutic gene: structural (cap) and packaging (rep) genes can be delivered in trans. With this assumption many methods were established for efficient production of recombinant AAV (rAAV) vectors containing a reporter or therapeutic gene. However, it was also published that the ITRs are not the only elements required in cis for the effective replication and encapsidation. A few research groups have identified a sequence designated cis-acting Rep-dependent element (CARE) inside the coding sequence of the rep gene. CARE was shown to augment the replication and encapsidation when present in cis.

As of 2006 there have been 11 AAV serotypes described, the 11th in 2004. All of the known serotypes can infect cells from multiple diverse tissue types. Tissue specificity is determined by the capsid serotype and pseudotyping of AAV vectors to alter their tropism range will likely be important to their use in therapy. In the present invention ITRs of AVV serotype 2 and serotype 5 are preferred.

Serotype 2

Serotype 2 (AAV2) has been the most extensively examined so far. AAV2 presents natural tropism towards skeletal muscles, neurons, vascular smooth muscle cells and hepatocytes.

Three cell receptors have been described for AAV2: heparan sulfate proteoglycan (HSPG), $\alpha_v\beta_5$ integrin and fibroblast growth factor receptor 1 (FGFR-1). The first functions as a primary receptor, while the latter two have a co-receptor activity and enable AAV to enter the cell by receptor-mediated endocytosis. These study results have been disputed by Qiu, Handa, et al. HSPG functions as the primary receptor, though its abundance in the extracellular matrix can scavenge AAV particles and impair the infection efficiency.

Serotype 2 and Cancer

Studies have shown that serotype 2 of the virus (AAV-2) apparently kills cancer cells without harming healthy ones. "Our results suggest that adeno-associated virus type 2, which infects the majority of the population but has no known ill effects, kills multiple types of cancer cells yet has no effect on healthy cells," said Craig Meyers, a professor of immunology and microbiology at the Penn State College of Medicine in Pennsylvania. This could lead to a new anti-cancer agent.

Other Serotypes

Although AAV2 is the most popular serotype in various AAV-based research, it has been shown that other serotypes can be more effective as gene delivery vectors. For instance AAV6 appears much better in infecting airway epithelial cells, AAV7 presents very high transduction rate of murine skeletal muscle cells (similarly to AAV1 and AAV5), AAV8 is superb in transducing hepatocytes and AAV1 and 5 were shown to be very efficient in gene delivery to vascular endothelial cells. In the brain, most AAV serotypes show neuronal tropism, while AAV5 also transduces astrocytes. AAV6, a hybrid of AAV1 and AAV2, also shows lower immunogenicity than AAV2.

Serotypes can differ with the respect to the receptors they are bound to. For example AAV4 and AAV5 transduction can be inhibited by soluble sialic acids (of different form for each of these serotypes), and AAV5 was shown to enter cells via the platelet-derived growth factor receptor.

In the present invention the delivery vehicles of the present invention may be administered to a patient. A skilled worker would be able to determined appropriate dosage rates. The term "administered" includes delivery by viral or non-viral techniques. Viral delivery mechanisms include but are not limited to adenoviral vectors, adeno-associated viral (AAV) vectors, herpes viral vectors, retroviral vectors, lentiviral vectors, and baculoviral vectors etc as described above. Non-viral delivery mechanisms include lipid mediated transfection, liposomes, immunoliposomes, lipofectin, cationic facial amphiphiles (CFAs) and combinations thereof.

The delivery of one or more therapeutic genes by a vector system according to the present invention may be used alone or in combination with other treatments or components of the treatment.

The present invention also provides a pharmaceutical composition for treating an individual by gene therapy, wherein the composition comprises a therapeutically effective amount of the vector/construct or host cell of the present invention comprising one or more deliverable therapeutic and/or diagnostic transgenes(s) or a viral particle produced by or obtained from same. The pharmaceutical composition may be for human or animal usage. Typically, a physician will determine the actual dosage which will be most suitable for an individual subject and it will vary with the age, weight and response of the particular individual. The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s), and other carrier agents that may aid or increase the viral entry into the target site (such as for example a lipid delivery system). Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

The man skilled in the art is well aware of the standard methods for incorporation of a polynucleotide or vector into a host cell, for example transfection, lipofection, electroporation, microinjection, viral infection, thermal shock, transformation after chemical permeabilisation of the membrane or cell fusion.

As used herein, the term "host cell or host cell genetically engineered" relates to host cells which have been transduced, transformed or transfected with the construct or with the vector described previously.

As representative examples of appropriate host cells, one can cites bacterial cells, such as *E. coli, Streptomyces, Salmonella typhimurium*, fungal cells such as yeast, insect cells such as Sf9, animal cells such as CHO or COS, plant cells, etc. The selection of an appropriate host is deemed to be within the scope of those skilled in the art from the teachings herein. Preferably, said host cell is an animal cell, and most preferably a human cell. The invention further provides a host cell comprising any of the recombinant expression vectors described herein. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α, *E. coli* cells, Chinese hamster ovarian cells, monkey VERO cells, COS cells, HEK293 cells, and the like.

The present invention will now be illustrated by means of non-limiting examples in reference to the following drawings.

FIG. 1. Schematic representation of AAV-based strategies for large gene transduction.

CDS: coding sequence; pA: poly-adenilation signal; SD: splicing donor signal; SA: splicing acceptor signal; AP: alkaline phosphatase recombinogenic region (39); AK: F1 phage recombinogenic region. Dotted lines show the splicing occurring between SD and SA, pointed lines show overlapping regions available for homologous recombination. The inventors found that dual trans-splicing and hybrid AK may be used to successfully reconstitute large gene expression. In particular dual trans-splicing and hybrid AK vectors, but not overlapping and hybrid AP vectors, transduce efficiently mouse and pig photoreceptors. Normal size and oversize AAV vector plasmids contained full length expression cassettes including the promoter, the full-length transgene CDS and the poly-adenilation signal (pA) (Table 1). The two separate AAV vector plasmids (5' and 3') required to generate dual AAV vectors contained either the promoter followed by the N-terminal portion of the transgene CDS (5' plasmid) or the C-terminal portion of the transgene CDS followed by the pA signal (3' plasmid, Table 1). The structure of all plasmids is indicated in the material and method section.

Figure 2:
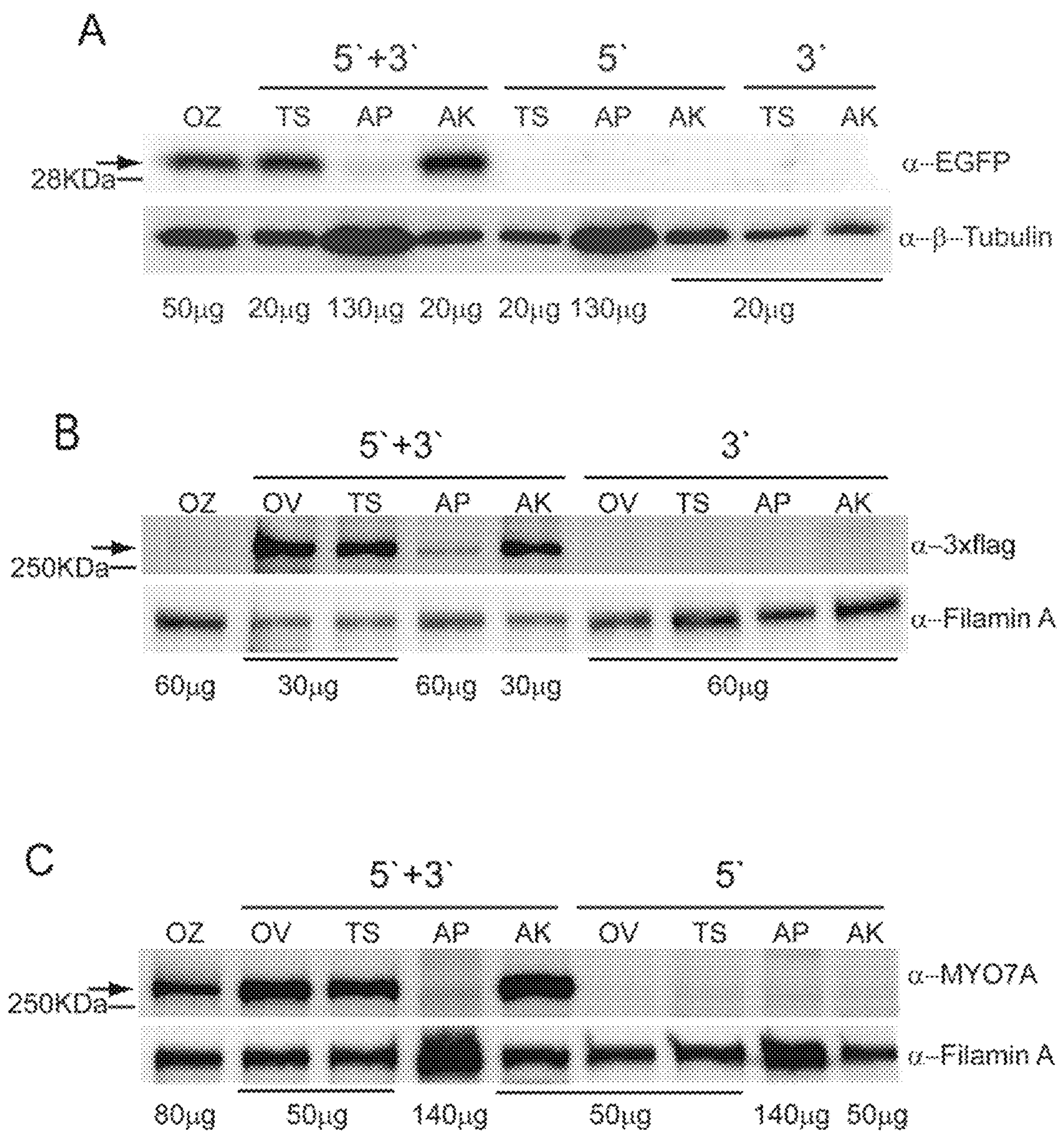
Figure 2:
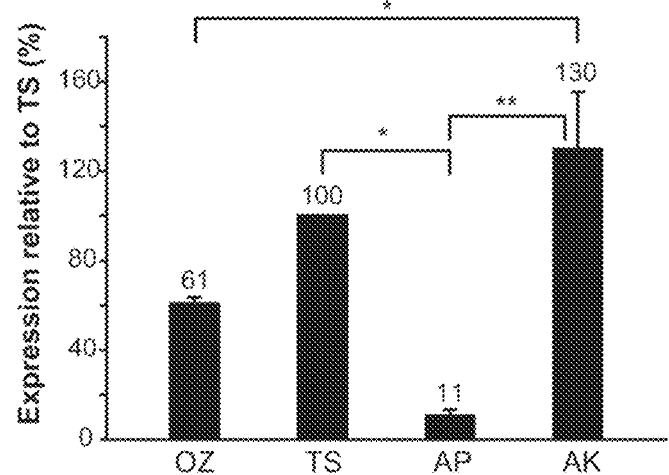
Figure 2:
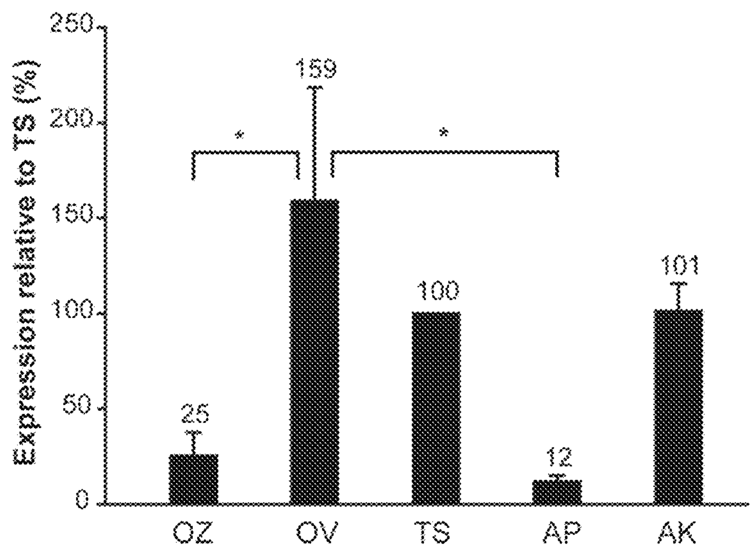
Figure 2:
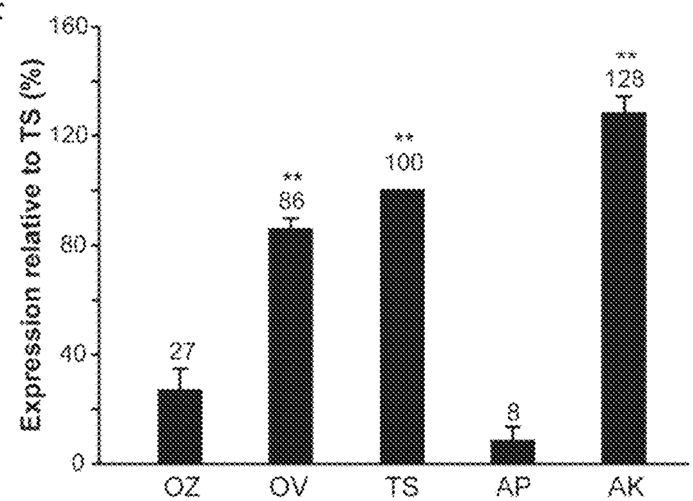

FIG. 2. Dual AAV overlapping, trans-splicing and hybrid AK vectors efficiently transduce large genes in vitro.

Figure 3:
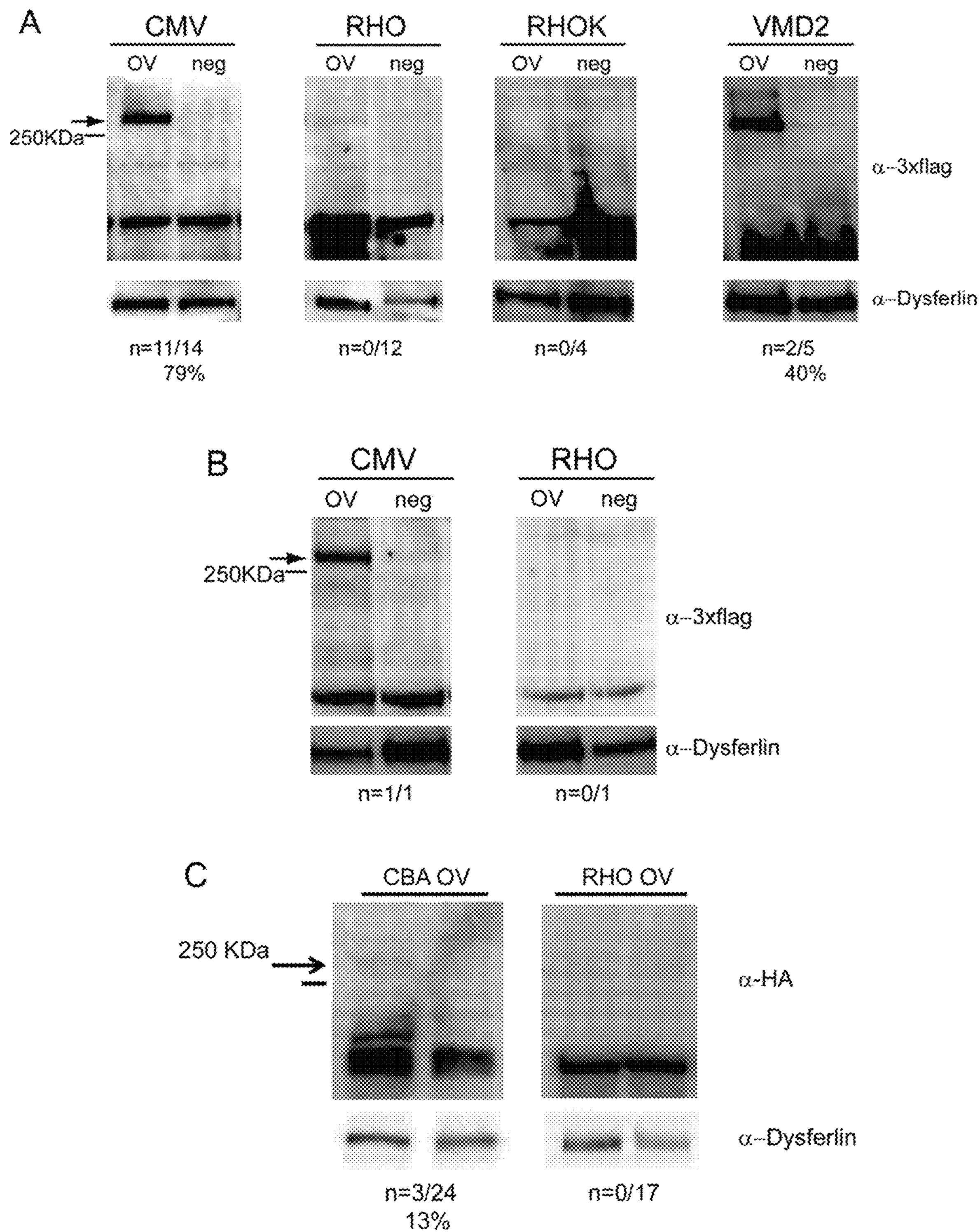

Western blot of HEK293 cells infected with AAV2/2 vectors encoding for EGFP (A and D), ABCA4 (B and E) and MYO7A (C and F). (A to C) The arrows indicate full-length proteins, the micrograms of proteins loaded are depicted under each lane, the molecular weight ladder is depicted on the left. (D to F) Quantification of EGFP (D), ABCA4 (E) and MYO7A (F) protein bands. The intensity of the EGFP, ABCA4 and MYO7A bands was divided by the intensity of the Tubulin (D) or Filamin A (E-F) bands. The histograms show the expression of proteins as a percentage relative to dual AAV trans-splicing (TS) vectors, the mean value is depicted above the corresponding bar. Error bars: mean±s.e.m. (standard error of the mean). (A-C) The Western blot images are representative of and the quantifications are from n=4 (A-B) or n=3 (C) independent experiments. OZ: AAV oversize; OV: dual AAV overlapping; TS: dual AAV trans-splicing; AP: dual AAV hybrid AP; AK: dual AAV hybrid AK; 5'+3': cells co-infected with 5'- and 3'-half vectors; 5': control cells infected with the 5'-half vector only; 3': control cells infected with the 3'-half only; α-EGFP: anti-EGFP antibody; α-3×flag: anti-3×flag antibody; α-MYO7A: anti-MYO7A antibody; α-β-Tubulin: anti-β-tubulin antibody; α-Filamin A: anti-filamin A antibody. * ANOVA p value<0.05;  ANOVA p value<0.001. (F) The asterisks depicted in the lower panel represent significant differences with both OZ and AP. In FIG. 3**. Dual AAV overlapping vectors transduce RPE but not photoreceptors in the mouse and pig retina.

Western blot analysis of C57BL/6 (A) and Large White pig (B) retinal lysates one month following injection of AAV2/8 dual AAV overlapping vectors encoding for ABCA4-3×flag (OV) or AAV2/8 vectors encoding for normal size EGFP (EGFP), under the control of the ubiquitous cytomegalovirus (CMV) promoter, the PR-specific Rhodopsin (RHO) and Rhodopsin kinase (RHOK) promoters, or the RPE-specific vitelliform macular dystrophy 2 (VMD2) promoter. (A-B) The arrows indicate full-length proteins, the molecular weight ladder is depicted on the left, 150 micrograms of proteins were loaded in each lane. The number (n) and percentage of ABCA4-positive retinas out of total retinas analyzed is depicted; α-3×flag: anti-3×flag antibody; α-Dysferlin: anti-Dysferlin antibody (C) Western blot analysis on C57/BL6 eyecups (left panel) and retinas (right panel) at 3 months following the injection of AAV2/8 overlapping vectors encoding for MYO7A-HA (OV) under the control of the ubiquitous chicken-beta-actin (CBA) promoter or the photoreceptor-specific rhodopsin (RHO) promoter. The arrow points at full-length proteins, the molecular weight ladder is depicted on the left, 100 micrograms of protein were loaded in each lane. The number (n) and percentage of MYO7A positive retinas out of total retinas analyzed is depicted. α-HA: anti-hemagglutinin (HA) antibody.

Figure 4:
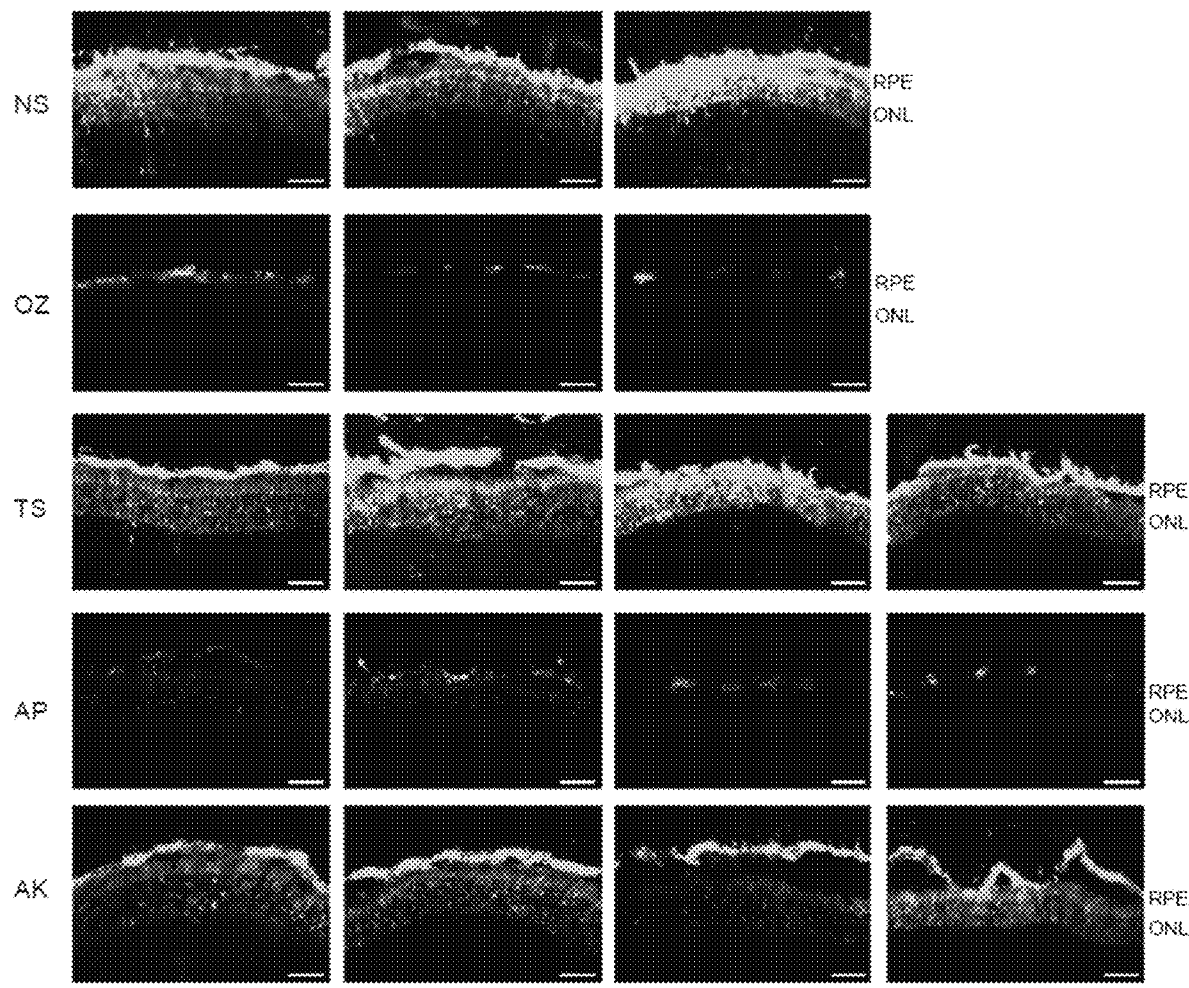

FIG. 4. Dual AAV trans-splicing and hybrid AK vectors efficiently transduce both RPE and photoreceptors.

Fluorescence analysis of retinal cryosections from C57BL/6 mice one month following subretinal injection of AAV2/8 vectors encoding for EGFP under the control of the ubiquitous cytomegalovirus (CMV) promoter. The scale bar (20 μm) is depicted in the figure. NS: AAV normal size; OZ: AAV oversize; TS: dual AAV trans-splicing; AP: dual AAV hybrid AP; AK: dual AAV hybrid AK; RPE: retinal pigmented epithelium; ONL: outer nuclear layer.

Figure 5:
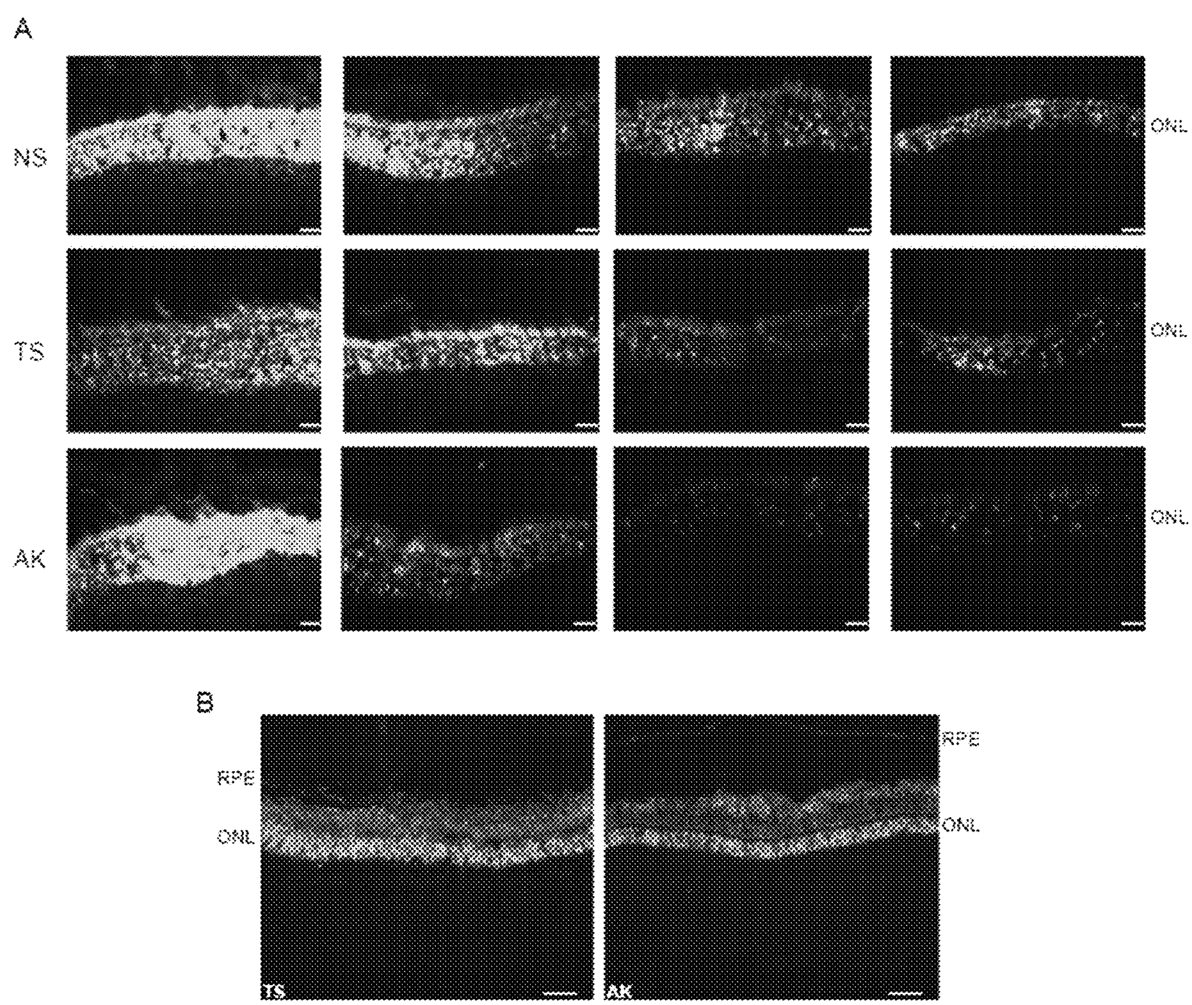

FIG. 5. Dual AAV trans-splicing and hybrid AK efficiently transduce mouse and pig photoreceptors.

(A) Fluorescence analysis of retinal cryosections from C57BL/6 mice one month following subretinal injection of AAV2/8 vectors encoding for EGFP under the control of the PR-specific Rhodopsin promoter (RHO). The scale bar (20 μm) is depicted in the figure. (B) Fluorescence analysis of retinal cryosections from Large White pigs one month following subretinal injection of AAV2/8 vectors encoding for EGFP under the control of the PR-specific RHO promoter. The scale bar (50 μm) is depicted in the figure. NS: AAV normal size; TS: dual AAV trans-splicing; AK: dual AAV hybrid AK; RPE: retinal pigmented epithelium; ONL: outer nuclear layer.

Figure 6:
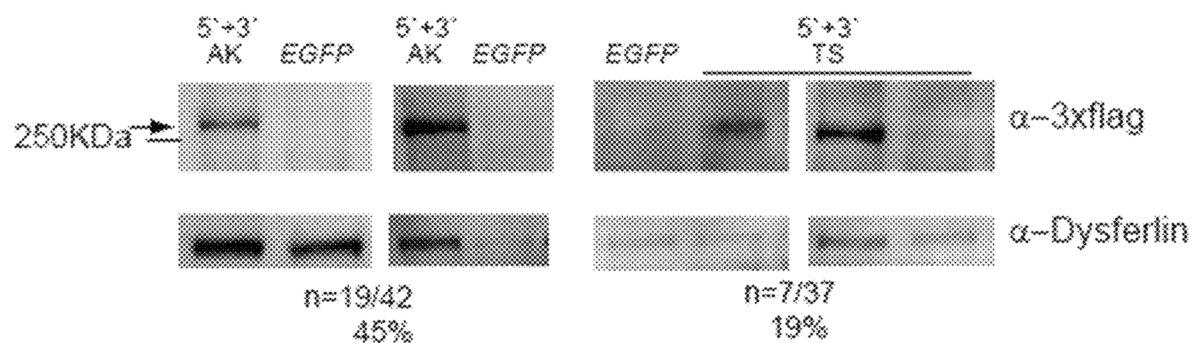
Figure 6:
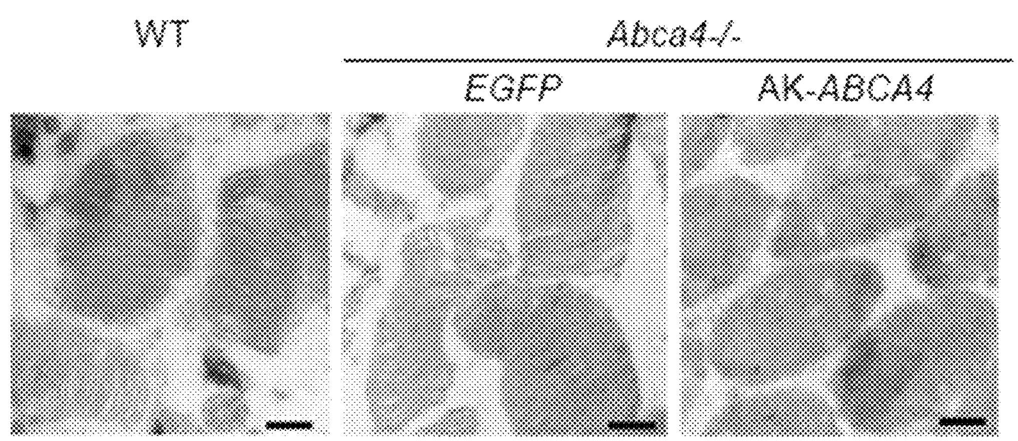

FIG. 6. Subretinal administration of dual AAV trans-splicing and hybrid AK vectors results in robust yet variable levels of ABCA4 expression in mouse photoreceptors.

(A) Western blot analysis of C57BL/6 retinal lysates one month following the injection of dual AAV trans-splicing (TS) and dual AAV hybrid AK (AK) vectors encoding for ABCA4 under the control of the PR-specific Rhodopsin promoter (RHO). The arrow points at full-length proteins, the molecular weight ladder is depicted on the left, 150 micrograms of protein were loaded in each lane. The number (n) and percentage of ABCA4-positive retinas out of total retinas analysed is depicted. 5'+3': retinas co-injected with 5'- and 3'-half vectors; α-3×flag: anti-3×flag antibody; α-Dysferlin: anti-Dysferlin antibody. (B) Immuno-electron microscopy analysis with anti-HA antibody of retinal sections from wild-type Balb/C (WT; n=3 eyes) and Abca4−/− mice injected with dual AAV hybrid AK vectors (AK-ABCA4; n=5 eyes) or with AAV normal size EGFP (EGFP, n=3 eyes) as control. The black dots represent the immunogold labelling of the ABCA4-HA protein. The scale bar (200 nm) is depicted in the figure.

Figure 7:
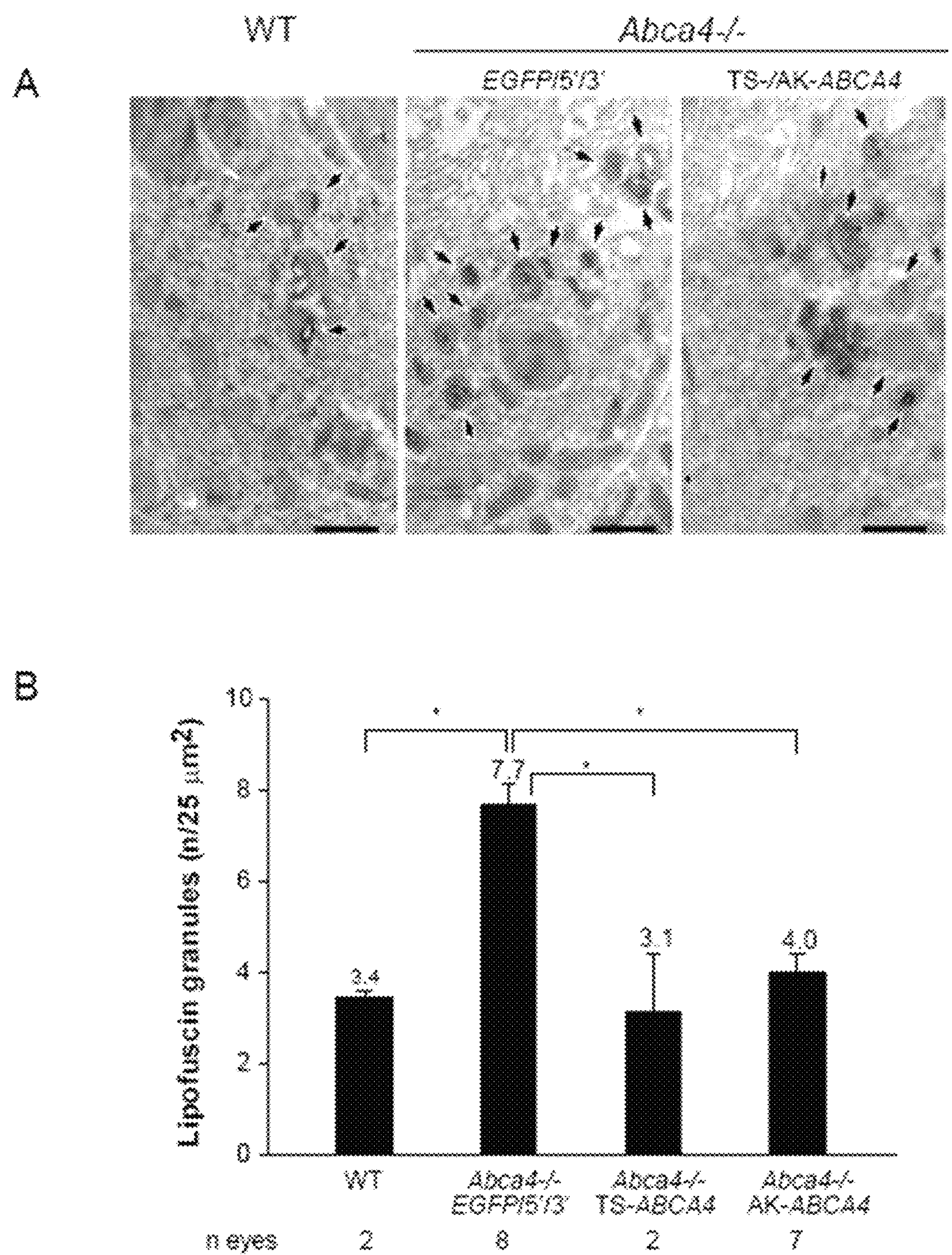

FIG. 7. Subretinal injection of dual AAV hybrid AK vectors reduces accumulation of lipofuscin granules in Abca4−/− mice.

(A) Transmission electron microscopy analysis of retinal sections from wild-type Balb/c (WT) and Abca4−/− mice injected with either dual AAV hybrid AK vectors (Abca4−/− AK-ABCA4) or with AAV normal size EGFP (Abca4−/− EGFP) as control. The black arrows indicate lipofuscin granules. The scale bar (1.6 μm) is depicted in the figure. (B) Quantification of the mean number of lipofuscin granules counted in at least 30 fields (25 $\mu m^2$) for each sample. WT: Balb/c mice; Abca4−/− EGFP/5'/3': Abca4−/− mice injected with either AAV normal size EGFP or the 5' or 3' half vector of the dual AAV hybrid AK, as control; Abca4−/− AK-ABCA4: mice injected with dual AAV hybrid AK vectors; Abca4−/− TS-ABCA4: mice injected with dual AAV trans-splicing vectors. The number (n) of eyes analysed is depicted. The mean value is depicted above the corresponding bar. Error bars: mean±s.e.m. (standard error of the mean). * p ANOVA<0.05

Figure 8:
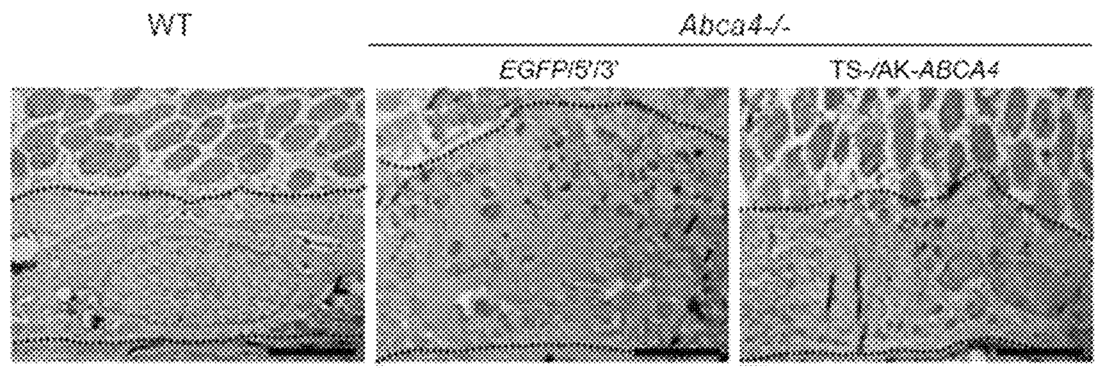
Figure 8:
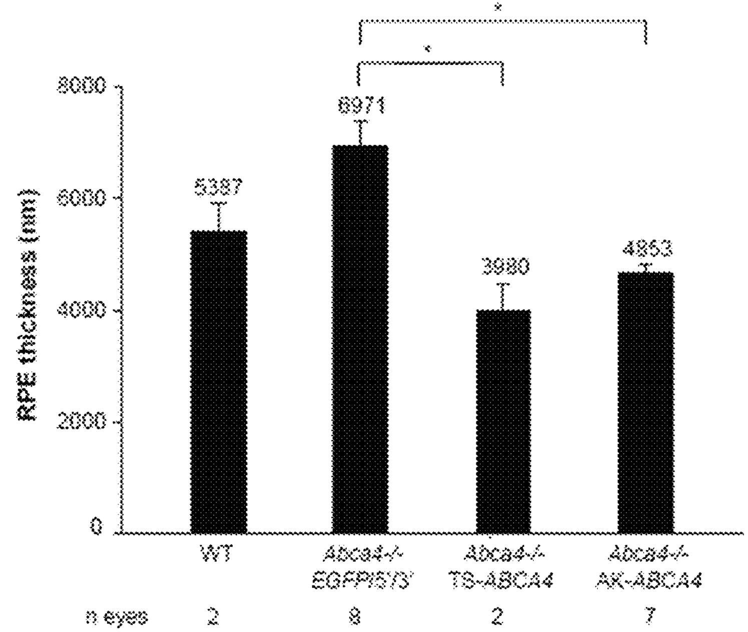

FIG. 8. Subretinal injections of dual AAV hybrid AK vectors reduces the thickness of Abca4−/− RPE.

(A) Representative pictures of transmission electron microscopy analysis of retinal sections from wild-type Balb/c (WT) and Abca4−/− mice injected with either dual AAV trans-splicing (TS-ABCA4) and hybrid AK vectors (AK-ABCA4) or with AAV normal size EGFP (EGFP) and 5' or 3' half of the dual hybrid AK vectors (5'/3') as control. The dotted lines indicate the edges of RPE cells. The scale bar (3.8 μm) is depicted in the figure. (B) Quantification of the mean RPE thickness counted in at least 30 fields for each sample. The number (n) of eyes analysed is depicted. The mean value is depicted above the corresponding bar. Error bars: mean±s.e.m (standard error of the mean). s.d.m: WT: ±716; TS-ABCA4: ±698.

Figure 9:
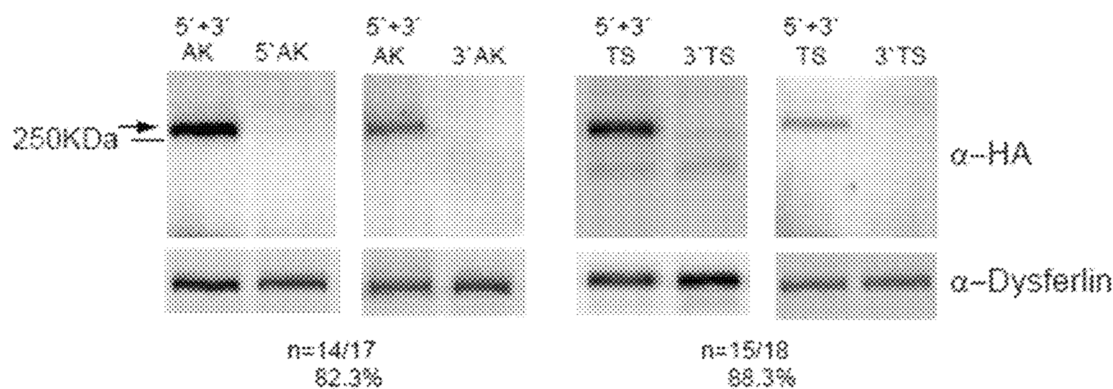

FIG. 9. Subretinal administration of dual AAV trans-splicing and hybrid AK vectors results in robust MYO7A expression in mice.

Western blot analysis of C57BL/6 eyecups one month following the injection of dual AAV trans-splicing (TS) and hybrid AK (AK) vectors encoding for MYO7A-HA under the control of the ubiquitous chicken beta-actin (CBA) promoter. The arrow indicates full-length proteins, the molecular weight ladder is depicted on the left, 100 micrograms of proteins were loaded in each lane. The number (n) and percentage of MYO7A-positive eyecups out of total retinas analyzed is depicted. 5'+3': eyes co-injected with 5'- and 3'-half vectors; 5': eyes injected with 5'-half vectors; 3': eyes injected with 3'-half vectors; α-HA: anti-hemagglutinin (HA) antibody; α-Dysferlin: anti-Dysferlin antibody.

Figure 10:
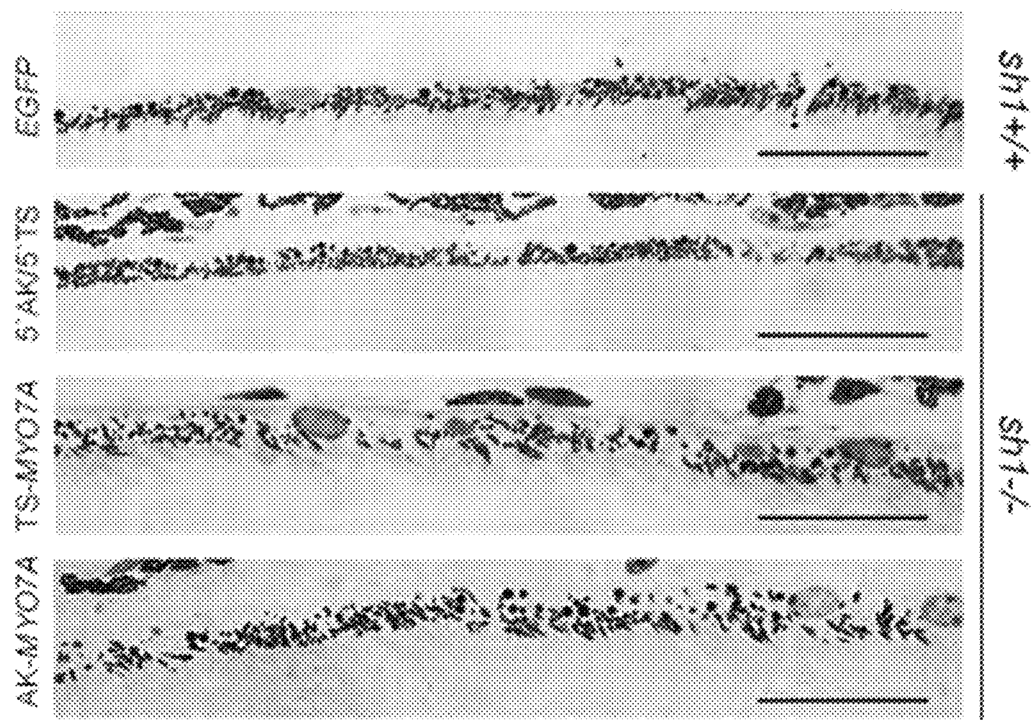
Figure 10:
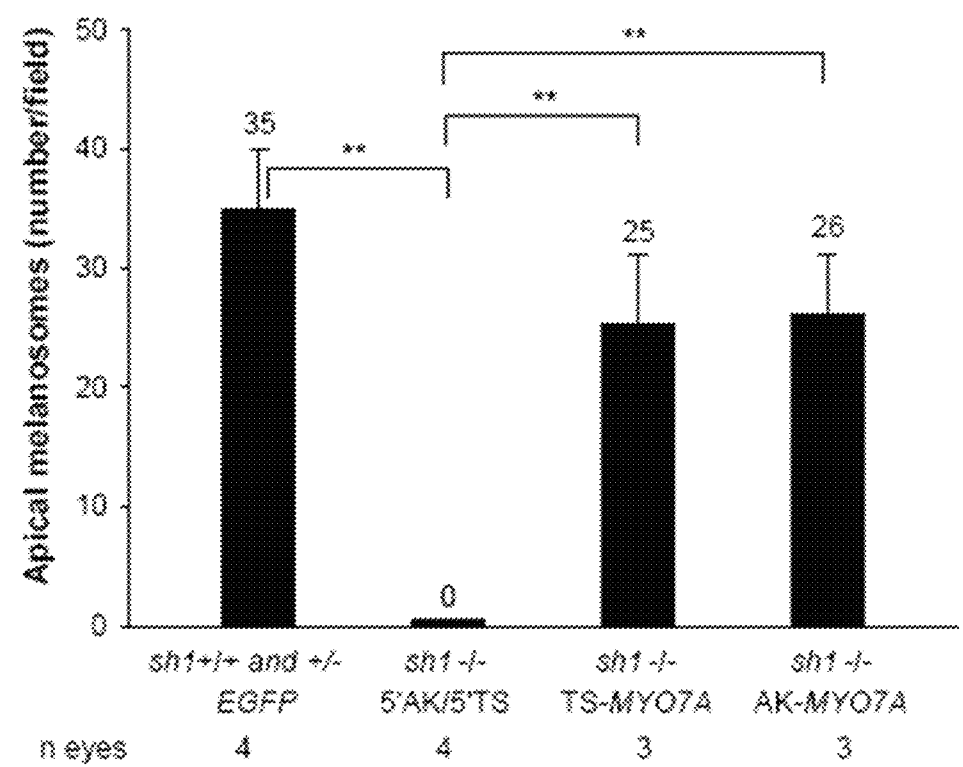

FIG. 10. Subretinal administration of dual AAV trans-splicing and hybrid AK vectors rescues melanosome localization in sh1−/− RPE.

(A) Representative semi-thin retinal sections stained with Epoxy tissue stain of sh1+/+ and sh1+/− eyes injected with AAV normal size EGFP (EGFP, n=4 eyes), and of sh1−/− eyes injected with dual AAV trans-splicing (TS-MYO7A, n=3 eyes), hybrid AK (AK-MYO7A; n=3 eyes) or 5'-half vectors (5'TS/5'AK, n=4 eyes), as control. The scale bar (10 μm) is depicted in the figure. (B) Quantification of melanosome localization in the RPE villi of sh1 mice two months following subretinal delivery of dual AAV vectors. The quantification is depicted as the mean number of apical melanosomes/field, the mean value is depicted above the corresponding bar. Error bars: mean±s.e.m. (standard error of the mean). * p ANOVA<0.05, ** p ANOVA<0.001.

Figure 11:
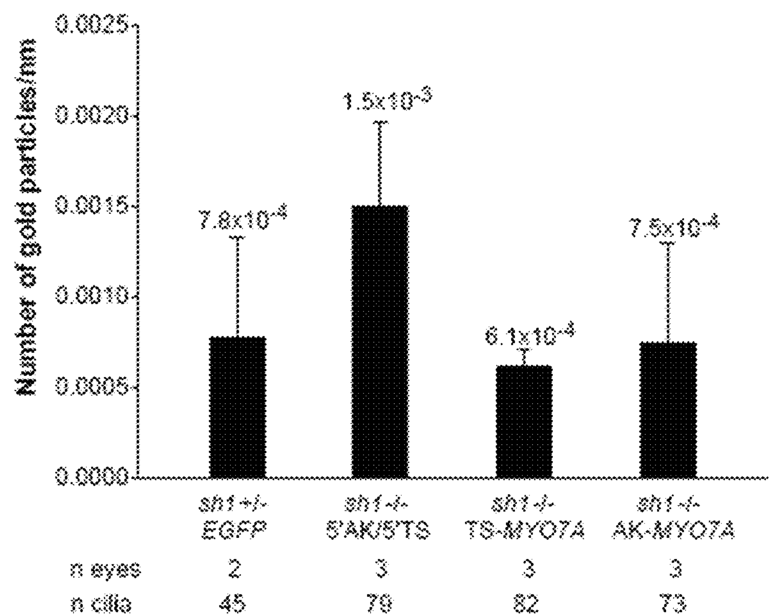

FIG. 11. Subretinal administration of dual AAV trans-splicing and hybrid AK vectors reduces rhodopsin accumulation at sh1−/− PR connecting cilia.

Quantification of the number of rhodopsin gold particles at the PR connecting cilium of sh1 mice two months following subretinal delivery of dual AAV vectors. The quantification is depicted as the mean number of gold particles per length of connecting cilia (nm), the mean value is depicted above the corresponding bar. Error bars: mean±s.e.m. (standard error of the mean).

Figure 12:
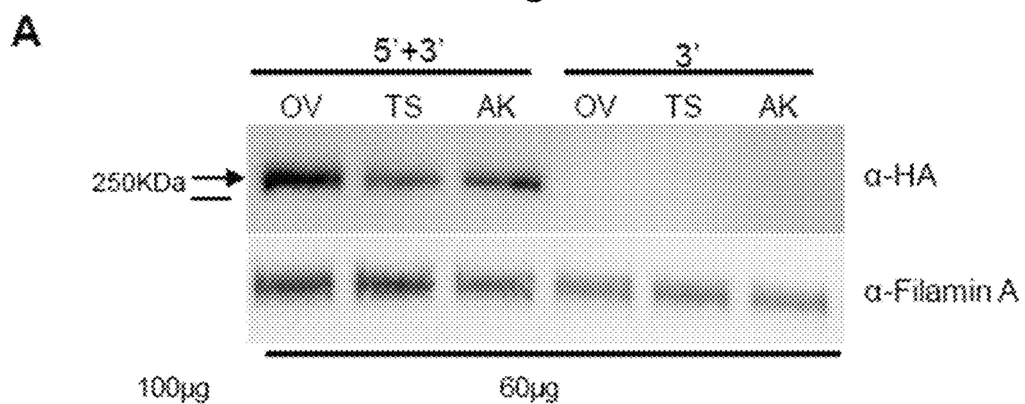
Figure 12:
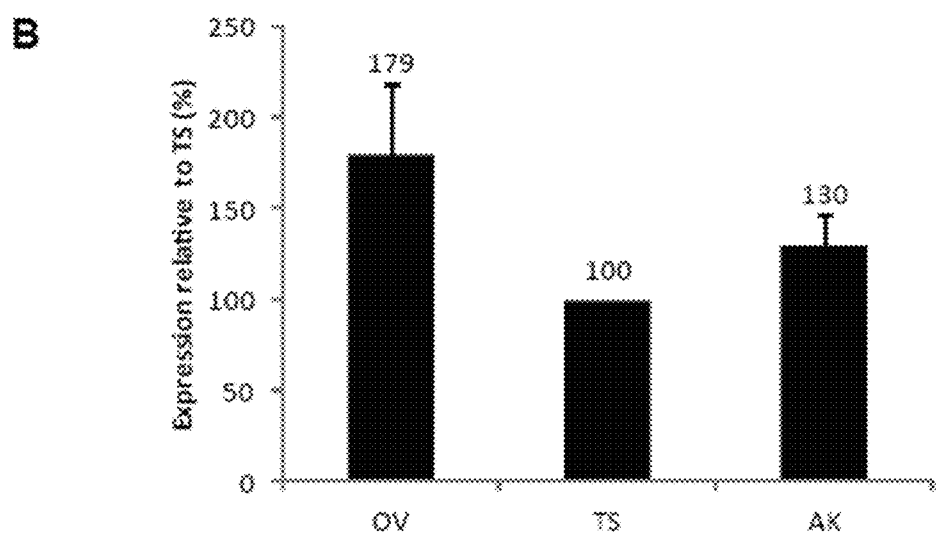

FIG. 12. Dual AAV trans-splicing and hybrid AK vectors efficiently transduce the large gene CEP290 in vitro.

Western blot of HEK293 cells infected with AAV2/2 vectors encoding for CEP290 tagged at its C-terminus with the hemagglutinin (HA) tag (A-B). (A) The arrow indicate the full-length protein, 60 micrograms of proteins were loaded for each lane, the molecular weight ladder is depicted on the left. (B) Quantification of CEP290 protein bands. The intensity of the CEP290 bands was divided by the intensity of the Filamin A bands. The histogram shows the expression of proteins as a percentage relative to dual AAV trans-splicing (TS) vectors, the mean value is depicted above the corresponding bar. Error bars: mean±s.e.m. (standard error of the mean). The Western blot image is representative of and the quantification is from n=5 independent experiments. OV: dual AAV overlapping; TS: dual AAV trans-splicing; AK: dual AAV hybrid AK; 5'+3': cells co-infected with 5'- and 3'-half vectors; 3': control cells infected with the 3'-half only; α-HA: anti-HA antibody; α-Filamin A: anti-filamin A antibody.

Figure 13:
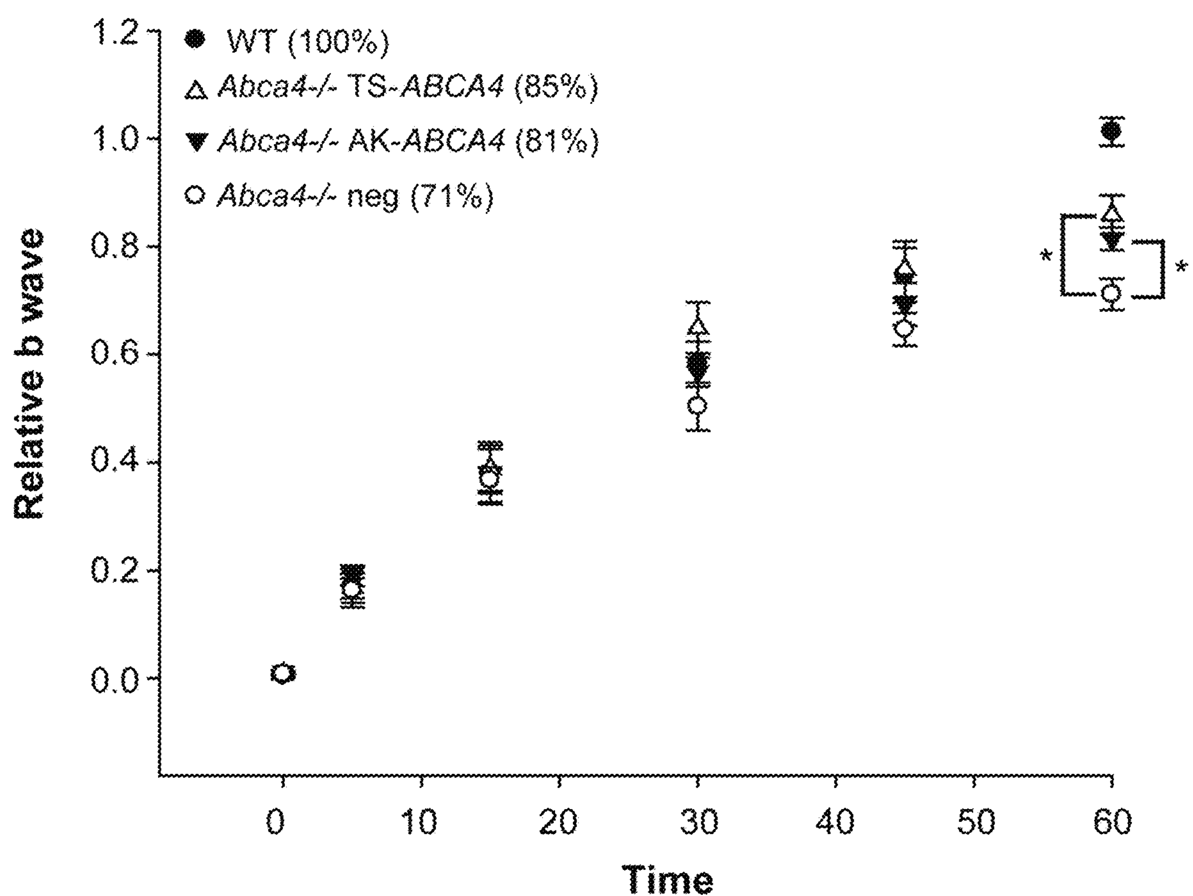

FIG. 13. Improved recovery from light desensitization in 3 months old Abca4−/− mice treated with dual AAV trans-splicing and hybrid AK vectors Recovery from light desensitization in Abca4−/− and Balb/c mice at 6 weeks post-injection. The relative b-wave is the ratio between the post- and the pre-desensitization b-wave amplitudes (μV) both evoked by 1 cd s/m$^2$. The time (minutes) refers to the time post-desensitization. The mean recovery (%) at 60 minutes is depicted. p ANOVA Abca4−/− AK-ABCA4 vs Abca4−/− uninjected/5': 0.05; p ANOVA Abca4−/− TS-ABCA4 vs Abca4−/− uninjected/5': 0.009; p ANOVA Abca4−/− AK-ABCA4 vs WT: 0.002; p ANOVA Abca4−/− TS-ABCA4 vs WT: 0.02; p ANOVA WT vs Abca4−/− uninjected/5': 0.00001. WT: Balb/c mice (n=4); Abca4−/− TS-ABCA4: mice injected with dual AAV trans-splicing vectors (n=5); Abca4−/− AK-ABCA4: mice injected with dual AAV hybrid AK vectors (n=5); Abca4−/− uninjected/5': Abca4−/− mice either not injected (n=2) or injected with the 5' half of the dual AAV TS or hybrid AK vectors (n=5). Data are depicted as mean±s.e.m (standard error of the mean). * p ANOVA<0.05.

Figure 14:
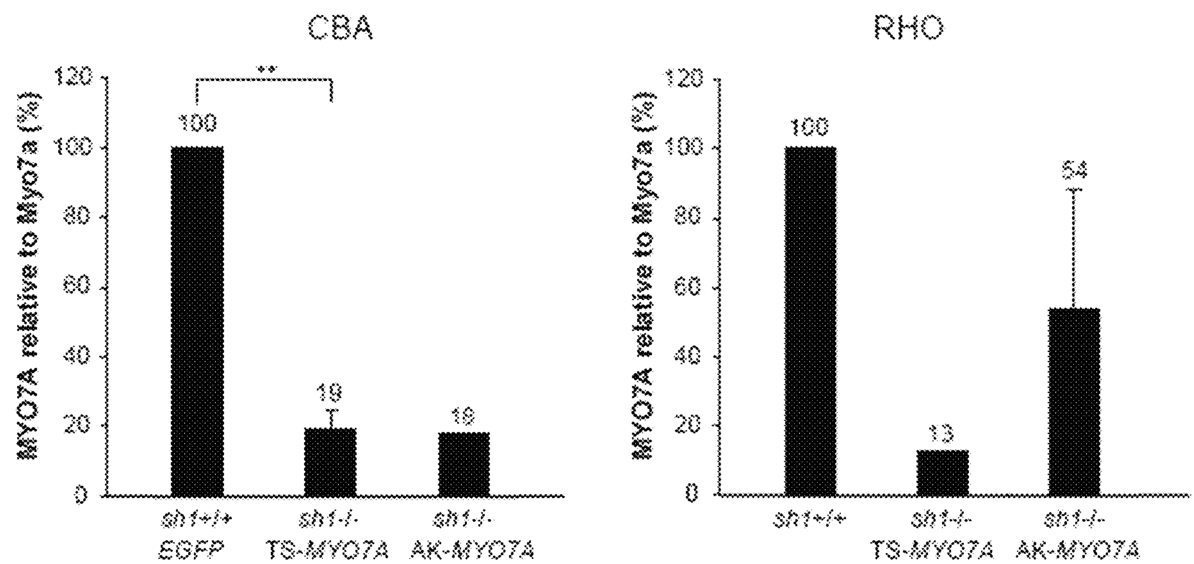

FIG. 14. Dual AAV hybrid AK vectors induce stronger MYO7A expression than dual AAV trans-splicing vectors in sh1−/− photoreceptors.

Quantification of MYO7A levels from dual AAV vectors in sh1−/− eyes relative to endogenous Myo7a expressed in sh1+/+ eyes. Sh1−/− eyes were injected with dual AAV TS and hybrid AK vectors encoding MYO7A under the control of either the CBA (left panel) or RHO (right panel) promoters. The histograms show the expression of MYO7A protein as percentage relative to sh1+/+Myo7a; the mean value is depicted above the corresponding bar. The quantification was performed by Western blot analysis using the anti-MYO7A antibody and measurements of MYO7A and Myo7a band intensities normalized to Dysferlin (data not shown). Error bars: mean±s.d.m. (standard deviation of the mean). The quantification is representative of: i. left panel: n=2 sh1+/+ eyecups, and n=5 or n=1 sh1−/− eyecups treated with either TS-MYO7A or AK-MYO7A, respectively; ii. right panel: n=2 sh1+/+ retinas, and n=1 or n=3 sh1−/− retinas treated with either TS-MYO7A or AK-MYO7A, respectively. ** p Student's t-test<0.001.

Figure 15:
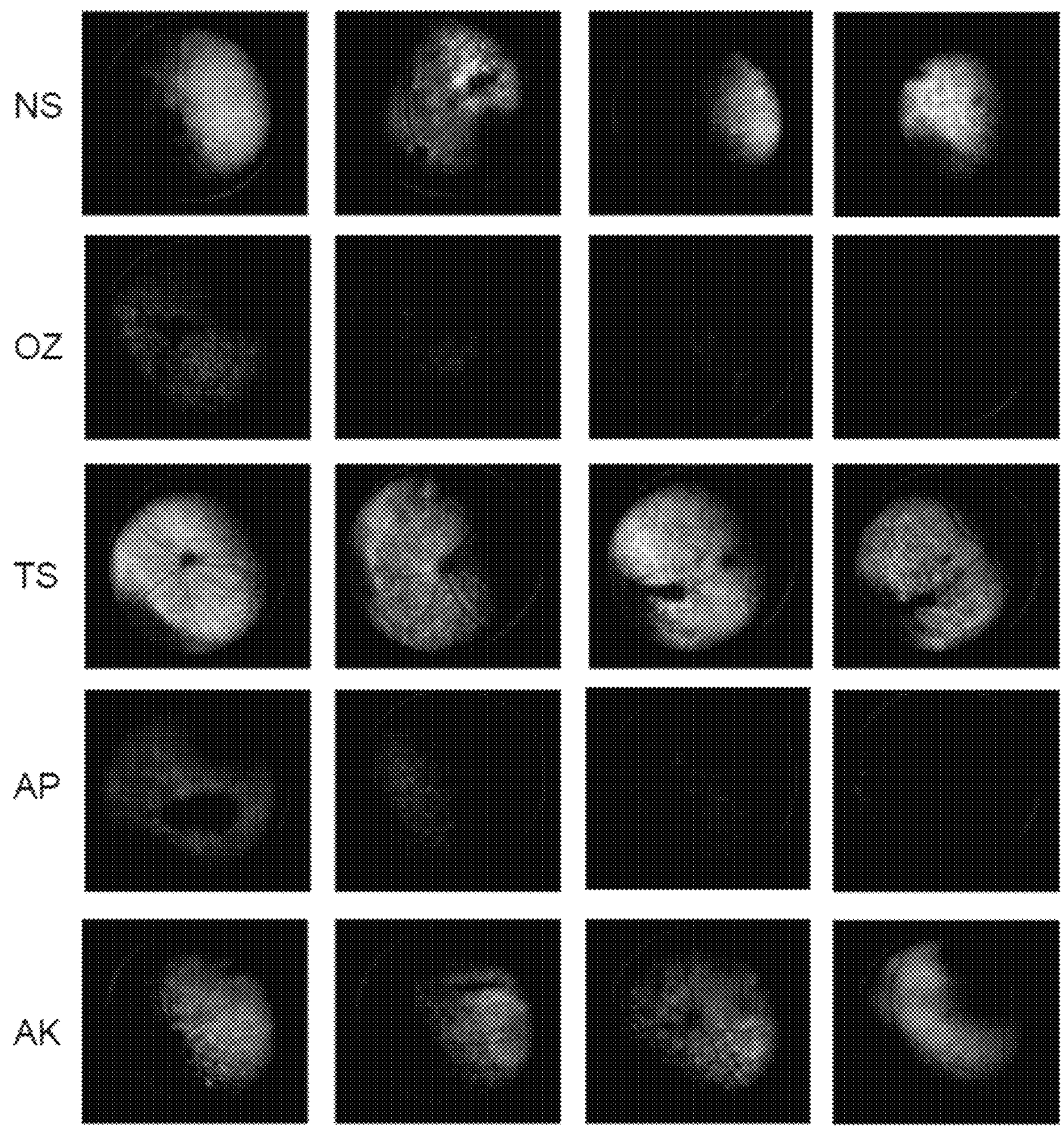

FIG. 15. AAV normal size, dual AAV trans-splicing and hybrid AK vectors provide the most robust transduction following subretinal delivery in mice.

Live-imaging fundus fluorescence of C57BL/6 eyes one month following subretinal injection of AAV2/8 vectors encoding for EGFP. NZ: Normal Size; OZ: AAV oversize; TS: dual AAV trans-splicing; AP: dual AAV hybrid AP; AK: dual AAV hybrid AK. Each panel shows a different eye.

Figure 16:
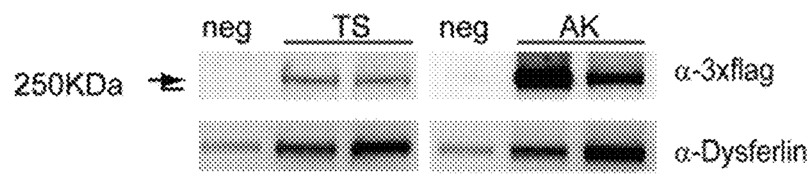
Figure 16:
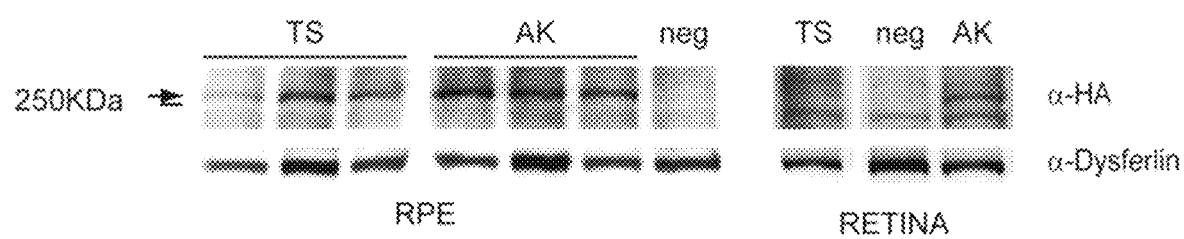

FIG. 16. Robust ABCA4 and MYO7A expression following delivery of dual AAV trans-splicing and hybrid AK vectors to the pig retina. (a) Western blot analysis of large white pig retinal lysates 1 month following injection of dual AAV2/8 trans-splicing (TS; n=2) and hybrid AK (AK; n=3) vectors encoding for ABCA4-3×flag or AAV2/8 vectors encoding for NS EGFP (neg), as negative control, under the control of the photoreceptor-specific rhodopsin (RHO) promoter. (b) Western blot analysis of large white pig retinal lysates one month following injection of dual AAV2/8 trans-splicing (TS: n=5 RPE; n=3 retina) and hybrid AK (AK: n=5 RPE, n=5 retina) vectors encoding for MYO7A-

HA under the control of the ubiquitous chicken beta actin (CBA) promoter or single 3'-half of dual AAV-MYO7A-HA (neg), as negative control. (a-b) The arrows indicate full-length proteins, the molecular weight ladder is depicted on the left, 150-180 μg of proteins were loaded in each lane. α-3×flag, anti-3×flag antibody; α-HA, anti-hemagglutinin antibody; α-dysferlin, anti-dysferlin antibody.

Figure 17:
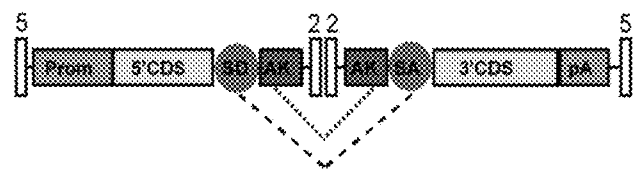
Figure 17:
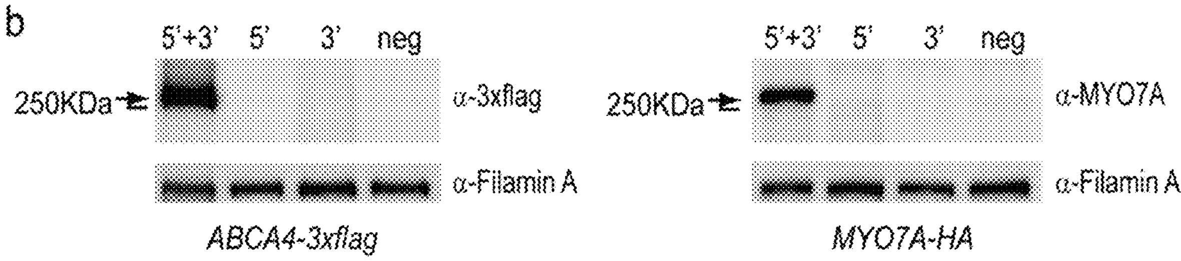

FIG. 17. Dual AAV hybrid AK vectors with heterologous ITRs transduce large genes in vitro. (a) Design of dual AAV hybrid AK vectors with heterologous ITR2 and ITR5. (b) Western blot analysis of HEK293 cells infected with dual AAV hybrid AK vectors with heterologous ITRs encoding for ABCA4 (left panel) and MYO7A (right panel). The arrows indicate full-length proteins, 50 micrograms of proteins were loaded, the molecular weight ladder is depicted on the left. 5'+3': cells co-infected with 5'- and 3'-half vectors; 5': control cells infected with the 5'-half vector only; 3': control cells infected with the 3'-half vector only; neg: cells infected with AAV2/8 vectors encoding for EGFP. α-3×flag: anti-3×flag antibody; α-MYO7A: anti-MYO7A antibody; α-Filamin: anti-filamin A antibody. (a) Prom: promoter; CDS: coding sequence; pA: poly-adenylation signal; SD: splicing donor signal; SA: splicing acceptor signal; Pointed lines show overlapping regions available for homologous recombination, dotted lines show the splicing occurring between SD and SA. The position of the heterologous ITR2 and ITR5 is depicted.

DETAILED DESCRIPTION OF THE INVENTION

Materials and Methods

Generation of AAV Vector Plasmids

The plasmids used for AAV vector production were derived from either the pZac2.1 (52) or pAAV2.1 (53) plasmids that contain the inverted terminal repeats (ITRs) of AAV serotype 2 (Table 1).

TABLE 1

Plasmids for AAV vector production.

| | Plasmid | Size ITR- ITR (bp) | AAV serotype 2/2 | 2/8 |
|---|---|---|---|---|
| Normal Size (NS) | pZac2.1-CMV-EGFP-SV40 | 3006 | X | X |
| | pZac2.1-RHO-EGFP-SV40 | 2900 | | X |
| Oversize (OZ) | pAAV2.1-CMV-EGFP-9.9-BGH | 9951 | X | X |
| | pZac2.1-CMV-ABCA4_3xflag-SV40 | 8619 | X | |
| | pAAV2.1-CBA-MYO7A_HA-BGH | 8220 | X | |
| Overlapping (OV) | pZac2.1-CMV-ABCA4_5' | 4900 | X | X |
| | pZac2.1-RHO-ABCA4_5' | 4805 | | X |
| | pZac2.1-RHOK-ABCA4_5' | 4169 | | X |
| | pZac2.1-VMD2-ABCA4_5' | 4658 | | X |
| | pAAV2.1-CBA-MYO7A_5' | 4708 | X | X |
| | pAAV2.1-RHO-MYO7A_5' | 4699 | | X |
| | pZac2.1-ABCA4_3'_3xflag_SV40 | 4740 | X | X |
| | pAAV2.1-MYO7A_3'_HA_BGH | 4655 | X | X |
| Trans-splicing (TS) | pZac2.1-CMV-ABCA4 _5'TS | 4431 | X | |
| | pZac2.1-RHO-ABCA4_ 5'TS | 4321 | | X |
| | pZac2.1-ABCA4 _3'TS_3xflag_SV40 | 4587 | X | X |
| | pAAV2.1-CBA-MYO7A _5'TS | 4468 | X | X |
| | pAAV2.1-RHO-MYO7A _5'TS | 4459 | | X |
| | pAAV2.1-MYO7A_3'TS_HA_BGH | 4298 | X | X |
| | pZac2.1-CMV-EGFP_5'TS | 1906 | X | X |
| | pZac2.1-RHO-EGFP_5'TS | 1802 | | X |
| | pZac2.1-EGFP_3'TS_SV40 | 1510 | X | X |
| Hybrid AP (AP) | pZac2.1-CMV-ABCA4_5'AP | 4708 | X | |
| | pZac2.1-ABCA4 _3'AP_3xflag_SV40 | 4871 | X | |
| | pAAV2.1-CBA-MYO7A_5'AP | 4746 | X | |
| | pAAV2.1-MYO7A_3'AP_HA_BGH | 4576 | X | |
| | pZac2.1-CMV-EGFP_5'AP | 2183 | X | X |
| | pZac2.1-EGFP_3'AP_SV40 | 1783 | X | X |
| Hybrid AK (AK) | pZac2.1-CMV-ABCA4 _5'AK | 4540 | X | |
| | pZac2.1 (ITR5:2)-CMV-ABCA4_5'AK | 4604 | X | |
| | pZac2.1-RHO-ABCA4_ 5'AK | 4436 | | X |
| | pZac2.1-ABCA4 _3'AK_3xflag_SV40 | 4702 | X | X |
| | pZac2.1 (ITR2:5)- ABCA4 _3'AK_3xflag_SV40 | 5192 | X | |
| | pZac2.1-ABCA4_ 3'AK_HA_SV40 | 4663 | | X |
| | pAAV2.1-CBA-MYO7A_5'AK | 4577 | X | X |
| | pAAV2.1 (ITR5:2)-CBA-MYO7A_5'AK | 4503 | X | |
| | pAAV2.1-RHO-MYO7A _5'AK | 4568 | | X |
| | pAAV2.1-MYO7A_3'AK_HA_BGH | 4421 | X | X |
| | pAAV2.1 (ITR2:5)-MYO7A_3'AK_HA_BGH | 4386 | X | |
| | pZac2.1-CMV-EGFP_5'AK | 2015 | X | X |
| | pZac2.1-RHO-EGFP_5'AK | 1911 | | X |
| | pZac2.1-EGFP_3'AK_SV40 | 1614 | X | X |

N.B. CMV: cytomegalovirus promoter; CBA: chicken beta-actin; RHO: human Rhodopsin promoter; RHOK: human Rhodopsin kinase promoter; Vmd2: vitelliform macular dystrophy 2 promoter; EGFP: enhanced green fluorescent protein; ABCA4: human ATP-binding cassette, sub-family A, member 4; MYO7A: human MYOSIN VIIA; SV40: simian virus 40 poly-adenilation signal; BGH: bovine growth hormone poly-adenilation signal; 3xflag: 3xflag tag; HA: hemagglutinin tag; AP: alkaline phosphatase recombinogenic region; AK: F1 phage recombinogenic region; TS: trans-splicing; ITR5:2: plasmid with the left ITR from AAV serotype 5 and the right ITR from AAV serotype 2; ITR2:5: plasmid with the left ITR from AAV serotype 2 and the right ITR from AAV serotype 5. When not specified the left and right ITR are from AAV serotype 2.

Normal size and oversize AAV vector plasmids contained full length expression cassettes including the promoter, the full-length transgene CDS and the poly-adenilation signal (pA) (Table 1). The two separate AAV vector plasmids (5' and 3') required to generate dual AAV vectors contained either the promoter followed by the N-terminal portion of the transgene CDS (5' plasmid) or the C-terminal portion of the transgene CDS followed by the pA signal (3' plasmid, Table 1). Normal size EGFP plasmids were generated by cloning the EGFP CDS of pAAV2.1-CMV-EGFP plasmid (720 bp) (53) in pZac2.1 (52); oversize EGFP was generated from pAAV2.1-CMV-EGFP (53) by inserting a DNA stuffer sequence of 3632 bp from human ABCA4 (NM_000350.2, bp 1960-5591) upstream of the CMV promoter and a second DNA stuffer sequence of 3621 bp, composed of: murine ABCA4 (NM 007378.1, 1066-1 and 7124-6046 bp; 2145 total bp) and human Harmonin (NM153676.3 131-1606 bp; 1476 total bp), downstream of the pA signal (This construct was used in the experiments of FIG. 1*a, d*, FIG. 4 and FIG. 15). To generate dual AAV vector plasmids, the EGFP CDS (720 bp) was split into two constructs: one containing the N-terminal CDS (PMID: 9759496, bp 1-393) and the other containing the C-terminal CDS (PMID: 9759496, bp 394-720).

The oversize ABCA4 plasmids contained the full-length human ABCA4 CDS (GeneNM_000350.2, bp 105-6926), while the oversize MYO7A plasmids contained the full-length human MYO7A CDS from isoform 1 (NM_000260.3, bp 273-6920). To generate plasmids for dual AAV OV vectors the ABCA4 and MYO7A CDS were split into two constructs, one containing N-terminal CDS (ABCA4: NM_000350.2, bp 105-3588; MYO7A: NM_000350.2, bp 273-3782) and the other containing C-terminal CDS (ABCA4: NM_000350.2, bp 2819-6926; MYO7A: NM_000350.2, bp 2913-6920). Therefore, the region of homology shared by overlapping vector plasmids was 770 bp for ABCA4 and 870 bp for MYO7A. To generate plasmids for dual AAV OV vectors the human CEP290 CDS was split into two constructs, one containing N-terminal CDS (CEP290: NM_025114, bp 345-4076) and the other containing C-terminal CDS (CEP290: NM_025114, bp 3575-7784). Therefore, the region of homology shared by overlapping vector plasmids was 502 bp.

To generate trans-splicing and hybrid vector plasmids the ABCA4 and MYO7A CDS were split at a natural exon-exon junction. ABCA4 was split between exons 19-20 (5' half: NM_000350.2, 105-3022 bp; 3' half: NM_000350.2, bp 3023-6926) and MYO7A was split between exons 24-25 (5' half: NM_000350.2, bp 273-3380; 3' half: NM_000350.2, bp 3381-6926). The ABCA4 and MYO7A proteins were both tagged at their C-terminus: ABCA4 with either the 3×flag (gactacaaagaccatgacggtgattataaagatcatgacatcgactacaaggatgacgatgacaag) or hemagglutinin (HA) tag (tatccgtatgatgtgccggattatgcg); MYO7A with the HA tag only. To generate trans-splicing and hybrid vector plasmids the CEP290 CDS was split at a natural exon-exon junction: between exons 29-30 (5' half: NM_025114, 345-3805; 3' half: NM_025114, 3806-7784). The CEP290 protein was tagged at its C-terminus with the hemagglutinin (HA) tag. The splice donor (SD) and splice acceptor (SA) signals contained in trans-splicing and hybrid dual AAV vector plasmids are as follows:

```
5'GTAAGTATCAAGGTTACAAGACAGGTTTAAGGAGACCAATAGAAACTG

GGCTTGTCGAGACAGAGAAGACTCTTGCGTTTCT-3' (SD) SEQ ID

No. 1;

5'GATAGGCACCTATTGGTCTTACTGACATCCACTTTGCCTTTCTCTCCA

CAG-3' (SA), SEQ ID No. 2.
```

The recombinogenic sequence contained in hybrid AP vector plasmids (present in both first and second plasmids) were derived from alkaline phosphate (AP) genes (NM_001632, bp 823-1100), as previously described (39). The recombinogenic sequence contained in hybrid AK vector plasmids (present in both first and second plasmids) were derived from the phage F1 genome (Gene Bank accession number: J02448.1; bp 5850-5926). The AK sequence is:

```
5'GGGATTTTGCCGATTTCGGCCTATTGGTTAAAAAATGAGCTGATTTAA

CAAAAATTTAACGCGAATTTTAACAAAAT-3', SEQ ID No. 3.
```

The ubiquitous CMV promoter is that contained in pZac2.1 (52) or pAAV2.1-CMV-EGFP (53); the ubiquitous CBA promoter was derived from pAAV2.1-CBA-EGFP (11), the PR-specific human RHO and RHOK promoters were derived from pAAV2.1-RHO-EGFP and pAAV2.1RHOK-EGFP, respectively (10); the RPE-specific Vmd2 promoter (NG_009033.1, 4870-5470 bp) corresponds to the previously described EcoRI-XcmI promoter fragment (41) and was amplified by human genomic DNA.

To generate dual AAV hybrid AK vectors with heterologous ITRs from AAV serotype 2 and 5 we exchanged the left ITR2 of the 5'-half plasmid and the right ITR2 of the 3'-half plasmid with the ITR5 (as depicted in FIG. 17*a*). The plasmids for the production of AAV2 vectors with heterologous ITRs are the following: pZac5:2-CMV-5'ABCA4-SD-AK, pZac2:5-AK-SD-3'ABCA4-3×flag, pAAV5:2-CBA-5'MYO7A-SD-AK and pAAV2:5-AK-SD-3'MYO7A-HA (Table 1).

```
Sequences
ABCA4 gene
pZac2.1-CMV-ABCA4_5'AK
Left ITR2
                                                   (SEQ ID No. 4)
CTGCGCGCTCGCTCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACTCCATCACTAGGG

GTTCCT
```

-continued

Left ITR5

(SEQ ID No. 5)

CTCTCCCCCCTGTCGCGTTCGCTCGCTCGCTGGCTCGTTTGGGGGGGTGGCAGCTCAAAGAG

CTGCCAGACGACGGCCCTCTGGCCGTCGCCCCCCCAAACGAGCCAGCGAGCGAGCGAACGCG

ACAGGGGGGAGAGTGCCACACTCTCAAGCAAGGGGGTTTTGTAAGCAGTGA

CMV enhancer (SEQ ID No. 6)

TCAATATTGGCCATTAGCCATATTATTCATTGGTTATATAGCATAAATCAATATTGGCTATT

GGCCATTGCATACGTTGTATCTATATCATAATATGTACATTTATATTGGCTCATGTCCAATA

TGACCGCCATGTTGGCATTGATTATTGAC

CMV promoter (SEQ ID No. 7)

TAGTTATTAATAGTAATCAATTACGGGGTCATTAGTTCATAGCCCATATATGGAGTTCCGCG

TTACATAACTTACGGTAAATGGCCCGCCTGGCTGACCGCCCAACGACCCCCGCCCATTGACG

TCAATAATGACGTATGTTCCCATAGTAACGCCAATAGGGACTTTCCATTGACGTCAATGGGT

GGAGTATTTACGGTAAACTGCCCACTTGGCAGTACATCAAGTGTATCATATGCCAAGTCCGC

CCCCTATTGACGTCAATGACGGTAAATGGCCCGCCTGGCATTATGCCCAGTACATGACCTTA

CGGGACTTTCCTACTTGGCAGTACATCTACGTATTAGTCATCGCTATTACCATGGTGATGCG

GTTTTGGCAGTACACCAATGGGCGTGGATAGCGGTTTGACTCACGGGGATTTCCAAGTCTCC

ACCCCATTGACGTCAATGGGAGTTTGTTTTGGCACCAAAATCAACGGGACTTTCCAAAATGT

CGTAATAACCCCGCCCCGTTGACGCAAATGGGCGGTAGGCGTGTACGGTGGGAGGTCTATAT

AAGCAGAGCTCGTTTAGTGAACCGT

Chimeric intron (SEQ ID No. 8)

GTAAGTATCAAGGTTACAAGACAGGTTTAAGGAGACCAATAGAAACTGGGCTTGTCGAGACA

GAGAAGACTCTTGCGTTTCTGATAGGCACCTATTGGTCTTACTGACATCCACTTTGCCTTTC

TCTCCACAG

Abca4 5'

(SEQ ID No. 9)

ATGGGCTTCGTGAGACAGATACAGCTTTTGCTCTGGAAGAACTGGACCCTGCGGAAAAGGCA

AAAGATTCGCTTTGTGGTGGAACTCGTGTGGCCTTTATCTTTATTTCTGGTCTTGATCTGGT

TAAGGAATGCCAACCCGCTCTACAGCCATCATGAATGCCATTTCCCCAACAAGGCGATGCCC

TCAGCAGGAATGCTGCCGTGGCTCCAGGGGATCTTCTGCAATGTGAACAATCCCTGTTTTCA

AAGCCCCACCCCAGGAGAATCTCCTGGAATTGTGTCAAACTATAACAACTCCATCTTGGCAA

GGGTATATCGAGATTTTCAAGAACTCCTCATGAATGCACCAGAGAGCCAGCACCTTGGCCGT

ATTTGGACAGAGCTACACATCTTGTCCCAATTCATGGACACCCTCCGGACTCACCCGGAGAG

AATTGCAGGAAGAGGAATTCGAATAAGGGATATCTTGAAAGATGAAGAAACACTGACACTAT

TTCTCATTAAAAACATCGGCCTGTCTGACTCAGTGGTCTACCTTCTGATCAACTCTCAAGTC

CGTCCAGAGCAGTTCGCTCATGGAGTCCCGGACCTGGCGCTGAAGGACATCGCCTGCAGCGA

GGCCCTCCTGGAGCGCTTCATCATCTTCAGCCAGAGACGCGGGGCAAAGACGGTGCGCTATG

CCCTGTGCTCCCTCTCCCAGGGCACCCTACAGTGGATAGAAGACACTCTGTATGCCAACGTG

GACTTCTTCAAGCTCTTCCGTGTGCTTCCCACACTCCTAGACAGCCGTTCTCAAGGTATCAA

TCTGAGATCTTGGGGAGGAATATTATCTGATATGTCACCAAGAATTCAAGAGTTTATCCATC

GGCCGAGTATGCAGGACTTGCTGTGGGTGACCAGGCCCCTCATGCAGAATGGTGGTCCAGAG

ACCTTTACAAAGCTGATGGGCATCCTGTCTGACCTCCTGTGTGGCTACCCCGAGGGAGGTGG

-continued

CTCTCGGGTGCTCTCCTTCAACTGGTATGAAGACAATAACTATAAGGCCTTTCTGGGGATTG

ACTCCACAAGGAAGGATCCTATCTATTCTTATGACAGAAGAACAACATCCTTTTGTAATGCA

TTGATCCAGAGCCTGGAGTCAAATCCTTTAACCAAAATCGCTTGGAGGGCGGCAAAGCCTTT

GCTGATGGGAAAAATCCTGTACACTCCTGATTCACCTGCAGCACGAAGGATACTGAAGAATG

CCAACTCAACTTTTGAAGAACTGGAACACGTTAGGAAGTTGGTCAAAGCCTGGGAAGAAGTA

GGGCCCCAGATCTGGTACTTCTTTGACAACAGCACACAGATGAACATGATCAGAGATACCCT

GGGGAACCCAACAGTAAAAGACTTTTTGAATAGGCAGCTTGGTGAAGAAGGTATTACTGCTG

AAGCCATCCTAAACTTCCTCTACAAGGGCCCTCGGGAAAGCCAGGCTGACGACATGGCCAAC

TTCGACTGGAGGGACATATTTAACATCACTGATCGCACCCTCCGCCTTGTCAATCAATACCT

GGAGTGCTTGGTCCTGGATAAGTTTGAAAGCTACAATGATGAAACTCAGCTCACCCAACGTG

CCCTCTCTCTACTGGAGGAAAACATGTTCTGGGCCGGAGTGGTATTCCCTGACATGTATCCC

TGGACCAGCTCTCTACCACCCCACGTGAAGTATAAGATCCGAATGGACATAGACGTGGTGGA

GAAAACCAATAAGATTAAAGACAGGTATTGGGATTCTGGTCCCAGAGCTGATCCCGTGGAAG

ATTTCCGGTACATCTGGGGCGGGTTTGCCTATCTGCAGGACATGGTTGAACAGGGGATCACA

AGGAGCCAGGTGCAGGCGGAGGCTCCAGTTGGAATCTACCTCCAGCAGATGCCCTACCCCTG

CTTCGTGGACGATTCTTTCATGATCATCCTGAACCGCTGTTTCCCTATCTTCATGGTGCTGG

CATGGATCTACTCTGTCTCCATGACTGTGAAGAGCATCGTCTTGGAGAAGGAGTTGCGACTG

AAGGAGACCTTGAAAAATCAGGGTGTCTCCAATGCAGTGATTTGGTGTACCTGGTTCCTGGA

CAGCTTCTCCATCATGTCGATGAGCATCTTCCTCCTGACGATATTCATCATGCATGGAAGAA

TCCTACATTACAGCGACCCATTCATCCTCTTCCTGTTCTTGTTGGCTTTCTCCACTGCCACC

ATCATGCTGTGCTTTCTGCTCAGCACCTTCTTCTCCAAGGCCAGTCTGGCAGCAGCCTGTAG

TGGTGTCATCTATTTCACCCTCTACCTGCCACACATCCTGTGCTTCGCCTGGCAGGACCGCA

TGACCGCTGAGCTGAAGAAGGCTGTGAGCTTACTGTCTCCGGTGGCATTTGGATTTGGCACT

GAGTACCTGGTTCGCTTTGAAGAGCAAGGCCTGGGGCTGCAGTGGAGCAACATCGGGAACAG

TCCCACGGAAGGGGACGAATTCAGCTTCCTGCTGTCCATGCAGATGATGCTCCTTGATGCTG

CTGTCTATGGCTTACTCGCTTGGTACCTTGATCAGGTGTTTCCAGGAGACTATGGAACCCCA

CTTCCTTGGTACTTTCTTCTACAAGAGTCGTATTGGCTTGGCGGTGAAGGGTGTTCAACCAG

AGAAGAAAGAGCCCTGGAAAAGACCGAGCCCCTAACAGAGGAAACGGAGGATCCAGAGCACC

CAGAAGGAATACACGACTCCTTCTTTGAACGTGAGCATCCAGGGTGGGTTCCTGGGGTATGC

GTGAAGAATCTGGTAAAGATTTTTGAGCCCTGTGGCCGGCCAGCTGTGGACCGTCTGAACAT

CACCTTCTACGAGAACCAGATCACCGCATTCCTGGGCCACAATGGAGCTGGGAAAACCACCA

CCTT

Splicing donor signal (SEQ ID No. 1)

GTAAGTATCAAGGTTACAAGACAGGTTTAAGGAGACCAATAGAAACTGGGCTTGTCGAGACA

GAGAAGACTCTTGCGTTTCT

AK (SEQ ID No. 3)

GGGATTTTGCCGATTTCGGCCTATTGGTTAAAAAATGAGCTGATTTAACAAAAATTTAACGC

GAATTTTAACAAAAT

-continued

Right ITR2 (or 5' ITR2)

(SEQ ID No. 10)

AGGAACCCCTAGTGATGGAGTTGGCCACTCCCTCTCTGCGCGCTCGCTCGCTCACTGAGGCC

GGGCGACCAAAGGTCGCCCGACGCCCGGGCTTTGCCCGGGCGGCCTCAGTGAGCGAGCGAGC

GCGCAG

Full length sequence of pZac2.1-CMV-ABCA4_5'AK (SEQ ID No. 11)

CTGCGCGCTCGCTCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACTCCATCACTAGGG

GTTCCTTGTAGTTAATGATTAACCCGCCATGCTACTTATCTACGTAGCCATGCTCTAGGAAG

ATCTTCAATATTGGCCATTAGCCATATTATTCATTGGTTATATAGCATAAATCAATATTGGC

TATTGGCCATTGCATACGTTGTATCTATATCATAATATGTACATTTATATTGGCTCATGTCC

AATATGACCGCCATGTTGGCATTGATTATTGACTAGTTATTAATAGTAATCAATTACGGGGT

CATTAGTTCATAGCCCATATATGGAGTTCCGCGTTACATAACTTACGGTAAATGGCCCGCCT

GGCTGACCGCCCAACGACCCCCGCCCATTGACGTCAATAATGACGTATGTTCCCATAGTAAC

GCCAATAGGGACTTTCCATTGACGTCAATGGGTGGAGTATTTACGGTAAACTGCCCACTTGG

CAGTACATCAAGTGTATCATATGCCAAGTCCGCCCCCTATTGACGTCAATGACGGTAAATGG

CCCGCCTGGCATTATGCCCAGTACATGACCTTACGGGACTTTCCTACTTGGCAGTACATCTA

CGTATTAGTCATCGCTATTACCATGGTGATGCGGTTTTGGCAGTACACCAATGGGCGTGGAT

AGCGGTTTGACTCACGGGGATTTCCAAGTCTCCACCCCATTGACGTCAATGGGAGTTTGTTT

TGGCACCAAAATCAACGGGACTTTCCAAAATGTCGTAATAACCCCGCCCCGTTGACGCAAAT

GGGCGGTAGGCGTGTACGGTGGGAGGTCTATATAAGCAGAGCTCGTTTAGTGAACCGTCAGA

TCACTAGAAGCTTTATTGCGGTAGTTTATCACAGTTAAATTGCTAACGCAGTCAGTGCTTCT

GACACAACAGTCTCGAACTTAAGCTGCAGAAGTTGGTCGTGAGGCACTGGGCAGGTAAGTAT

CAAGGTTACAAGACAGGTTTAAGGAGACCAATAGAAACTGGGCTTGTCGAGACAGAGAAGAC

TCTTGCGTTTCTGATAGGCACCTATTGGTCTTACTGACATCCACTTTGCCTTTCTCTCCACA

GGTGTCCACTCCCAGTTCAATTACAGCTCTTAAGGCTAGAGTACTTAATACGACTCACTATA

GGCTAGCCTCGAGAATTCACGCGTGGTACCTCTAGAGTCGACCCGGGCGGCCGCCATGGGCT

TCGTGAGACAGATACAGCTTTTGCTCTGGAAGAACTGGACCCTGCGGAAAAGGCAAAAGATT

CGCTTTGTGGTGGAACTCGTGTGGCCTTTATCTTTATTTCTGGTCTTGATCTGGTTAAGGAA

TGCCAACCCGCTCTACAGCCATCATGAATGCCATTTCCCCAACAAGGCGATGCCCTCAGCAG

GAATGCTGCCGTGGCTCCAGGGGATCTTCTGCAATGTGAACAATCCCTGTTTTCAAAGCCCC

ACCCCAGGAGAATCTCCTGGAATTGTGTCAAACTATAACAACTCCATCTTGGCAAGGGTATA

TCGAGATTTTCAAGAACTCCTCATGAATGCACCAGAGAGCCAGCACCTTGGCCGTATTTGGA

CAGAGCTACACATCTTGTCCCAATTCATGGACACCCTCCGGACTCACCCGGAGAGAATTGCA

GGAAGAGGAATTCGAATAAGGGATATCTTGAAAGATGAAGAAACACTGACACTATTTCTCAT

TAAAAACATCGGCCTGTCTGACTCAGTGGTCTACCTTCTGATCAACTCTCAAGTCCGTCCAG

AGCAGTTCGCTCATGGAGTCCCGGACCTGGCGCTGAAGGACATCGCCTGCAGCGAGGCCCTC

CTGGAGCGCTTCATCATCTTCAGCCAGAGACGCGGGGCAAAGACGGTGCGCTATGCCCTGTG

CTCCCTCTCCCAGGGCACCCTACAGTGGATAGAAGACACTCTGTATGCCAACGTGGACTTCT

TCAAGCTCTTCCGTGTGCTTCCCACACTCCTAGACAGCCGTTCTCAAGGTATCAATCTGAGA

TCTTGGGGAGGAATATTATCTGATATGTCACCAAGAATTCAAGAGTTTATCCATCGGCCGAG

-continued

TATGCAGGACTTGCTGTGGGTGACCAGGCCCCTCATGCAGAATGGTGGTCCAGAGACCTTTA

CAAAGCTGATGGGCATCCTGTCTGACCTCCTGTGTGGCTACCCCGAGGGAGGTGGCTCTCGG

GTGCTCTCCTTCAACTGGTATGAAGACAATAACTATAAGGCCTTTCTGGGGATTGACTCCAC

AAGGAAGGATCCTATCTATTCTTATGACAGAAGAACAACATCCTTTTGTAATGCATTGATCC

AGAGCCTGGAGTCAAATCCTTTAACCAAAATCGCTTGGAGGGCGGCAAAGCCTTTGCTGATG

GGAAAAATCCTGTACACTCCTGATTCACCTGCAGCACGAAGGATACTGAAGAATGCCAACTC

AACTTTTGAAGAACTGGAACACGTTAGGAAGTTGGTCAAAGCCTGGGAAGAAGTAGGGCCCC

AGATCTGGTACTTCTTTGACAACAGCACACAGATGAACATGATCAGAGATACCCTGGGGAAC

CCAACAGTAAAAGACTTTTTGAATAGGCAGCTTGGTGAAGAAGGTATTACTGCTGAAGCCAT

CCTAAACTTCCTCTACAAGGGCCCTCGGGAAAGCCAGGCTGACGACATGGCCAACTTCGACT

GGAGGGACATATTTAACATCACTGATCGCACCCTCCGCCTTGTCAATCAATACCTGGAGTGC

TTGGTCCTGGATAAGTTTGAAAGCTACAATGATGAAACTCAGCTCACCCAACGTGCCCTCTC

TCTACTGGAGGAAAACATGTTCTGGGCCGGAGTGGTATTCCCTGACATGTATCCCTGGACCA

GCTCTCTACCACCCCACGTGAAGTATAAGATCCGAATGGACATAGACGTGGTGGAGAAAACC

AATAAGATTAAAGACAGGTATTGGGATTCTGGTCCCAGAGCTGATCCCGTGGAAGATTTCCG

GTACATCTGGGGCGGGTTTGCCTATCTGCAGGACATGGTTGAACAGGGGATCACAAGGAGCC

AGGTGCAGGCGGAGGCTCCAGTTGGAATCTACCTCCAGCAGATGCCCTACCCCTGCTTCGTG

GACGATTCTTTCATGATCATCCTGAACCGCTGTTTCCCTATCTTCATGGTGCTGGCATGGAT

CTACTCTGTCTCCATGACTGTGAAGAGCATCGTCTTGGAGAAGGAGTTGCGACTGAAGGAGA

CCTTGAAAAATCAGGGTGTCTCCAATGCAGTGATTTGGTGTACCTGGTTCCTGGACAGCTTC

TCCATCATGTCGATGAGCATCTTCCTCCTGACGATATTCATCATGCATGGAAGAATCCTACA

TTACAGCGACCCATTCATCCTCTTCCTGTTCTTGTTGGCTTTCTCCACTGCCACCATCATGC

TGTGCTTTCTGCTCAGCACCTTCTTCTCCAAGGCCAGTCTGGCAGCAGCCTGTAGTGGTGTC

ATCTATTTCACCCTCTACCTGCCACACATCCTGTGCTTCGCCTGGCAGGACCGCATGACCGC

TGAGCTGAAGAAGGCTGTGAGCTTACTGTCTCCGGTGGCATTTGGATTTGGCACTGAGTACC

TGGTTCGCTTTGAAGAGCAAGGCCTGGGGCTGCAGTGGAGCAACATCGGGAACAGTCCCACG

GAAGGGGACGAATTCAGCTTCCTGCTGTCCATGCAGATGATGCTCCTTGATGCTGCTGTCTA

TGGCTTACTCGCTTGGTACCTTGATCAGGTGTTTCCAGGAGACTATGGAACCCCACTTCCTT

GGTACTTTCTTCTACAAGAGTCGTATTGGCTTGGCGGTGAAGGGTGTTCAACCAGAGAAGAA

AGAGCCCTGGAAAAGACCGAGCCCCTAACAGAGGAAACGGAGGATCCAGAGCACCCAGAAGG

AATACACGACTCCTTCTTTGAACGTGAGCATCCAGGGTGGGTTCCTGGGGTATGCGTGAAGA

ATCTGGTAAAGATTTTTGAGCCCTGTGGCCGGCCAGCTGTGGACCGTCTGAACATCACCTTC

TACGAGAACCAGATCACCGCATTCCTGGGCCACAATGGAGCTGGGAAAACCACCACCTTGTA

AGTATCAAGGTTACAAGACAGGTTTAAGGAGACCAATAGAAACTGGGCTTGTCGAGACAGAG

AAGACTCTTGCGTTTCTGGGATTTTGCCGATTTCGGCCTATTGGTTAAAAAATGAGCTGATT

TAACAAAAATTTAACGCGAATTTTAACAAAATATTAACGTTTATAATTTCAGGTGGCATCTT

TCCAATTGAGGAACCCCTAGTGATGGAGTTGGCCACTCCCTCTCTGCGCGCTCGCTCGCTCA

CTGAGGCCGGGCGACCAAAGGTCGCCCGACGCCCGGGCTTTGCCCGGGCGGCCTCAGTGAGC

GAGCGAGCGCGCAG

-continued pZac2.1-ABCA4_3'AK_SV40
Left ITR2

(SEQ ID No. 4)
CTGCGCGCTCGCTCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACTCCATCACTAGGG

GTTCCT

AK (SEQ ID No. 3)
GGGATTTTGCCGATTTCGGCCTATTGGTTAAAAAATGAGCTGATTTAACAAAAATTTAACGC

GAATTTTAACAAAAT

Splicing acceptor signal (SEQ ID No. 2)
GATAGGCACCTATTGGTCTTACTGACATCCACTTTGCCTTTCTCTCCACAG Abca4_3'

(SEQ ID No. 12)
GTCCATCCTGACGGGTCTGTTGCCACCAACCTCTGGGACTGTGCTCGTTGGGGGAAGGGACA

TTGAAACCAGCCTGGATGCAGTCCGGCAGAGCCTTGGCATGTGTCCACAGCACAACATCCTG

TTCCACCACCTCACGGTGGCTGAGCACATGCTGTTCTATGCCCAGCTGAAAGGAAAGTCCCA

GGAGGAGGCCCAGCTGGAGATGGAAGCCATGTTGGAGGACACAGGCCTCCACCACAAGCGGA

ATGAAGAGGCTCAGGACCTATCAGGTGGCATGCAGAGAAAGCTGTCGGTTGCCATTGCCTTT

GTGGGAGATGCCAAGGTGGTGATTCTGGACGAACCCACCTCTGGGGTGGACCCTTACTCGAG

ACGCTCAATCTGGGATCTGCTCCTGAAGTATCGCTCAGGCAGAACCATCATCATGTCCACTC

ACCACATGGACGAGGCCGACCTCCTTGGGGACCGCATTGCCATCATTGCCCAGGGAAGGCTC

TACTGCTCAGGCACCCCACTCTTCCTGAAGAACTGCTTTGGCACAGGCTTGTACTTAACCTT

GGTGCGCAAGATGAAAAACATCCAGAGCCAAAGGAAAGGCAGTGAGGGGACCTGCAGCTGCT

CGTCTAAGGGTTTCTCCACCACGTGTCCAGCCCACGTCGATGACCTAACTCCAGAACAAGTC

CTGGATGGGGATGTAAATGAGCTGATGGATGTAGTTCTCCACCATGTTCCAGAGGCAAAGCT

GGTGGAGTGCATTGGTCAAGAACTTATCTTCCTTCTTCCAAATAAGAACTTCAAGCACAGAG

CATATGCCAGCCTTTTCAGAGAGCTGGAGGAGACGCTGGCTGACCTTGGTCTCAGCAGTTTT

GGAATTTCTGACACTCCCCTGGAAGAGATTTTTCTGAAGGTCACGGAGGATTCTGATTCAGG

ACCTCTGTTTGCGGGTGGCGCTCAGCAGAAAAGAGAAAACGTCAACCCCCGACACCCCTGCT

TGGGTCCCAGAGAGAAGGCTGGACAGACACCCCAGGACTCCAATGTCTGCTCCCCAGGGGCG

CCGGCTGCTCACCCAGAGGGCCAGCCTCCCCCAGAGCCAGAGTGCCCAGGCCCGCAGCTCAA

CACGGGGACACAGCTGGTCCTCCAGCATGTGCAGGCGCTGCTGGTCAAGAGATTCCAACACA

CCATCCGCAGCCACAAGGACTTCCTGGCGCAGATCGTGCTCCCGGCTACCTTTGTGTTTTTG

GCTCTGATGCTTTCTATTGTTATCCCTCCTTTTGGCGAATACCCCGCTTTGACCCTTCACCC

CTGGATATATGGGCAGCAGTACACCTTCTTCAGCATGGATGAACCAGGCAGTGAGCAGTTCA

CGGTACTTGCAGACGTCCTCCTGAATAAGCCAGGCTTTGGCAACCGCTGCCTGAAGGAAGGG

TGGCTTCCGGAGTACCCCTGTGGCAACTCAACACCCTGGAAGACTCCTTCTGTGTCCCCAAA

CATCACCCAGCTGTTCCAGAAGCAGAAATGGACACAGGTCAACCCTTCACCATCCTGCAGGT

GCAGCACCAGGGAGAAGCTCACCATGCTGCCAGAGTGCCCCGAGGGTGCCGGGGGCCTCCCG

CCCCCCCAGAGAACACAGCGCAGCACGGAAATTCTACAAGACCTGACGGACAGGAACATCTC

CGACTTCTTGGTAAAAACGTATCCTGCTCTTATAAGAAGCAGCTTAAAGAGCAAATTCTGGG

TCAATGAACAGAGGTATGGAGGAATTTCCATTGGAGGAAAGCTCCCAGTCGTCCCCATCACG

GGGGAAGCACTTGTTGGGTTTTTAAGCGACCTTGGCCGGATCATGAATGTGAGCGGGGGCCC

-continued

TATCACTAGAGAGGCCTCTAAAGAAATACCTGATTTCCTTAAACATCTAGAAACTGAAGACA

ACATTAAGGTGTGGTTTAATAACAAAGGCTGGCATGCCCTGGTCAGCTTTCTCAATGTGGCC

CACAACGCCATCTTACGGGCCAGCCTGCCTAAGGACAGAAGCCCCGAGGAGTATGGAATCAC

CGTCATTAGCCAACCCCTGAACCTGACCAAGGAGCAGCTCTCAGAGATTACAGTGCTGACCA

CTTCAGTGGATGCTGTGGTTGCCATCTGCGTGATTTTCTCCATGTCCTTCGTCCCAGCCAGC

TTTGTCCTTTATTTGATCCAGGAGCGGGTGAACAAATCCAAGCACCTCCAGTTTATCAGTGG

AGTGAGCCCCACCACCTACTGGGTAACCAACTTCCTCTGGGACATCATGAATTATTCCGTGA

GTGCTGGGCTGGTGGTGGGCATCTTCATCGGGTTTCAGAAGAAAGCCTACACTTCTCCAGAA

AACCTTCCTGCCCTTGTGGCACTGCTCCTGCTGTATGGATGGGCGGTCATTCCCATGATGTA

CCCAGCATCCTTCCTGTTTGATGTCCCCAGCACAGCCTATGTGGCTTTATCTTGTGCTAATC

TGTTCATCGGCATCAACAGCAGTGCTATTACCTTCATCTTGGAATTATTTGAGAATAACCGG

ACGCTGCTCAGGTTCAACGCCGTGCTGAGGAAGCTGCTCATTGTCTTCCCCCACTTCTGCCT

GGGCCGGGGCCTCATTGACCTTGCACTGAGCCAGGCTGTGACAGATGTCTATGCCCGGTTTG

GTGAGGAGCACTCTGCAAATCCGTTCCACTGGGACCTGATTGGGAAGAACCTGTTTGCCATG

GTGGTGGAAGGGGTGGTGTACTTCCTCCTGACCCTGCTGGTCCAGCGCCACTTCTTCCTCTC

CCAATGGATTGCCGAGCCCACTAAGGAGCCCATTGTTGATGAAGATGATGATGTGGCTGAAG

AAAGACAAAGAATTATTACTGGTGGAAATAAAACTGACATCTTAAGGCTACATGAACTAACC

AAGATTTATCCAGGCACCTCCAGCCCAGCAGTGGACAGGCTGTGTGTCGGAGTTCGCCCTGG

AGAGTGCTTTGGCCTCCTGGGAGTGAATGGTGCCGGCAAAACAACCACATTCAAGATGCTCA

CTGGGGACACCACAGTGACCTCAGGGGATGCCACCGTAGCAGGCAAGAGTATTTTAACCAAT

ATTTCTGAAGTCCATCAAAATATGGGCTACTGTCCTCAGTTTGATGCAATCGATGAGCTGCT

CACAGGACGAGAACATCTTTACCTTTATGCCCGGCTTCGAGGTGTACCAGCAGAAGAAATCG

AAAAGGTTGCAAACTGGAGTATTAAGAGCCTGGGCCTGACTGTCTACGCCGACTGCCTGGCT

GGCACGTACAGTGGGGGCAACAAGCGGAAACTCTCCACAGCCATCGCACTCATTGGCTGCCC

ACCGCTGGTGCTGCTGGATGAGCCCACCACAGGGATGGACCCCCAGGCACGCCGCATGCTGT

GGAACGTCATCGTGAGCATCATCAGAGAAGGGAGGGCTGTGGTCCTCACATCCCACAGCATG

GAAGAATGTGAGGCACTGTGTACCCGGCTGGCCATCATGGTAAAGGGCGCCTTTCGATGTAT

GGGCACCATTCAGCATCTCAAGTCCAAATTTGGAGATGGCTATATCGTCACAATGAAGATCA

AATCCCCGAAGGACGACCTGCTTCCTGACCTGAACCCTGTGGAGCAGTTCTTCCAGGGGAAC

TTCCCAGGCAGTGTGCAGAGGGAGAGGCACTACAACATGCTCCAGTTCCAGGTCTCCTCCTC

CTCCCTGGCGAGGATCTTCCAGCTCCTCCTCTCCCACAAGGACAGCCTGCTCATCGAGGAGT

ACTCAGTCACACAGACCACACTGGACCAGGTGTTTGTAAATTTTGCTAAACAGCAGACTGAA

AGTCATGACCTCCCTCTGCACCCTCGAGCTGCTGGAGCCAGTCGACAAGCCCAGGACGACTA

CAAAGACCATGACGGTGATTATAAAGATCATGACATCGACTACAAGGATGACGATGACAAGT

GAGCGGCCGC

Sv40 polyA (SEQ ID No. 13)

TTCGAGCAGACATGATAAGATACATTGATGAGTTTGGACAAACCACAACTAGAATGCAGTGA

AAAAAATGCTTTATTTGTGAAATTTGTGATGCTATTGCTTTATTTGTAACCATTATAAGCTG

CAATAAACAAGTTAACAACAACAATTGCATTCATTTTATGTTTCAGGTTCAGGGGGAGATGT

-continued

GGGAGGTTTTTTAAAGCAAGTAAAACCTCTACAAATGTGGTAAAATCGATAAGGATCTTCCT

AGAGCATGGCTAC

Right ITR2

(SEQ ID No. 10)

AGGAACCCCTAGTGATGGAGTTGGCCACTCCCTCTCTGCGCGCTCGCTCGCTCACTGAGGCC

GGGCGACCAAAGGTCGCCCGACGCCCGGGCTTTGCCCGGGCGGCCTCAGTGAGCGAGCGAGC

GCGCAG

RIGHT ITR5

(SEQ ID No. 14)

TCACTGCTTACAAAACCCCCTTGCTTGAGAGTGTGGCACTCTCCCCCCTGTCGCGTTCGCTC

GCTCGCTGGCTCGTTTGGGGGGGCGACGGCCAGAGGGCCGTCGTCTGGCAGCTCTTTGAGCT

GCCACCCCCCCAAACGAGCCAGCGAGCGAGCGAACGCGACAGGGGGGAGAG

Full length sequence of pZac2.1-ABCA4_3'AK_SV40

(SEQ ID No. 15)

CTGCGCGCTCGCTCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACTCCATCACTAGGG

GTTCCTGGATCCGGGATTTTGCCGATTTCGGCCTATTGGTTAAAAAATGAGCTGATTTAACA

AAAATTTAACGCGAATTTTAACAAAATATTAACGTTTATAATTTCAGGTGGCATCTTTCGAT

AGGCACCTATTGGTCTTACTGACATCCACTTTGCCTTTCTCTCCACAGGTCCATCCTGACGG

GTCTGTTGCCACCAACCTCTGGGACTGTGCTCGTTGGGGGAAGGGACATTGAAACCAGCCTG

GATGCAGTCCGGCAGAGCCTTGGCATGTGTCCACAGCACAACATCCTGTTCCACCACCTCAC

GGTGGCTGAGCACATGCTGTTCTATGCCCAGCTGAAAGGAAAGTCCCAGGAGGAGGCCCAGC

TGGAGATGGAAGCCATGTTGGAGGACACAGGCCTCCACCACAAGCGGAATGAAGAGGCTCAG

GACCTATCAGGTGGCATGCAGAGAAAGCTGTCGGTTGCCATTGCCTTTGTGGGAGATGCCAA

GGTGGTGATTCTGGACGAACCCACCTCTGGGGTGGACCCTTACTCGAGACGCTCAATCTGGG

ATCTGCTCCTGAAGTATCGCTCAGGCAGAACCATCATCATGTCCACTCACCACATGGACGAG

GCCGACCTCCTTGGGGACCGCATTGCCATCATTGCCCAGGGAAGGCTCTACTGCTCAGGCAC

CCCACTCTTCCTGAAGAACTGCTTTGGCACAGGCTTGTACTTAACCTTGGTGCGCAAGATGA

AAAACATCCAGAGCCAAAGGAAAGGCAGTGAGGGGACCTGCAGCTGCTCGTCTAAGGGTTTC

TCCACCACGTGTCCAGCCCACGTCGATGACCTAACTCCAGAACAAGTCCTGGATGGGGATGT

AAATGAGCTGATGGATGTAGTTCTCCACCATGTTCCAGAGGCAAAGCTGGTGGAGTGCATTG

GTCAAGAACTTATCTTCCTTCTTCCAAATAAGAACTTCAAGCACAGAGCATATGCCAGCCTT

TTCAGAGAGCTGGAGGAGACGCTGGCTGACCTTGGTCTCAGCAGTTTTGGAATTTCTGACAC

TCCCCTGGAAGAGATTTTTCTGAAGGTCACGGAGGATTCTGATTCAGGACCTCTGTTTGCGG

GTGGCGCTCAGCAGAAAAGAGAAAACGTCAACCCCCGACACCCCTGCTTGGGTCCCAGAGAG

AAGGCTGGACAGACACCCCAGGACTCCAATGTCTGCTCCCCAGGGGCGCCGGCTGCTCACCC

AGAGGGCCAGCCTCCCCCAGAGCCAGAGTGCCCAGGCCCGCAGCTCAACACGGGGACACAGC

TGGTCCTCCAGCATGTGCAGGCGCTGCTGGTCAAGAGATTCCAACACACCATCCGCAGCCAC

AAGGACTTCCTGGCGCAGATCGTGCTCCCGGCTACCTTTGTGTTTTTGGCTCTGATGCTTTC

TATTGTTATCCCTCCTTTTGGCGAATACCCCGCTTTGACCCTTCACCCCTGGATATATGGGC

AGCAGTACACCTTCTTCAGCATGGATGAACCAGGCAGTGAGCAGTTCACGGTACTTGCAGAC

GTCCTCCTGAATAAGCCAGGCTTTGGCAACCGCTGCCTGAAGGAAGGGTGGCTTCCGGAGTA

CCCCTGTGGCAACTCAACACCCTGGAAGACTCCTTCTGTGTCCCCAAACATCACCCAGCTGT

-continued

TCCAGAAGCAGAAATGGACACAGGTCAACCCTTCACCATCCTGCAGGTGCAGCACCAGGGAG

AAGCTCACCATGCTGCCAGAGTGCCCCGAGGGTGCCGGGGGCCTCCCGCCCCCCCAGAGAAC

ACAGCGCAGCACGGAAATTCTACAAGACCTGACGGACAGGAACATCTCCGACTTCTTGGTAA

AAACGTATCCTGCTCTTATAAGAAGCAGCTTAAAGAGCAAATTCTGGGTCAATGAACAGAGG

TATGGAGGAATTTCCATTGGAGGAAAGCTCCCAGTCGTCCCCATCACGGGGGAAGCACTTGT

TGGGTTTTTAAGCGACCTTGGCCGGATCATGAATGTGAGCGGGGGCCCTATCACTAGAGAGG

CCTCTAAAGAAATACCTGATTTCCTTAAACATCTAGAAACTGAAGACAACATTAAGGTGTGG

TTTAATAACAAAGGCTGGCATGCCCTGGTCAGCTTTCTCAATGTGGCCCACAACGCCATCTT

ACGGGCCAGCCTGCCTAAGGACAGAAGCCCCGAGGAGTATGGAATCACCGTCATTAGCCAAC

CCCTGAACCTGACCAAGGAGCAGCTCTCAGAGATTACAGTGCTGACCACTTCAGTGGATGCT

GTGGTTGCCATCTGCGTGATTTTCTCCATGTCCTTCGTCCCAGCCAGCTTTGTCCTTTATTT

GATCCAGGAGCGGGTGAACAAATCCAAGCACCTCCAGTTTATCAGTGGAGTGAGCCCCACCA

CCTACTGGGTAACCAACTTCCTCTGGGACATCATGAATTATTCCGTGAGTGCTGGGCTGGTG

GTGGGCATCTTCATCGGGTTTCAGAAGAAAGCCTACACTTCTCCAGAAAACCTTCCTGCCCT

TGTGGCACTGCTCCTGCTGTATGGATGGGCGGTCATTCCCATGATGTACCCAGCATCCTTCC

TGTTTGATGTCCCCAGCACAGCCTATGTGGCTTTATCTTGTGCTAATCTGTTCATCGGCATC

AACAGCAGTGCTATTACCTTCATCTTGGAATTATTTGAGAATAACCGGACGCTGCTCAGGTT

CAACGCCGTGCTGAGGAAGCTGCTCATTGTCTTCCCCCACTTCTGCCTGGGCCGGGGCCTCA

TTGACCTTGCACTGAGCCAGGCTGTGACAGATGTCTATGCCCGGTTTGGTGAGGAGCACTCT

GCAAATCCGTTCCACTGGGACCTGATTGGGAAGAACCTGTTTGCCATGGTGGTGGAAGGGGT

GGTGTACTTCCTCCTGACCCTGCTGGTCCAGCGCCACTTCTTCCTCTCCCAATGGATTGCCG

AGCCCACTAAGGAGCCCATTGTTGATGAAGATGATGATGTGGCTGAAGAAAGACAAAGAATT

ATTACTGGTGGAAATAAAACTGACATCTTAAGGCTACATGAACTAACCAAGATTTATCCAGG

CACCTCCAGCCCAGCAGTGGACAGGCTGTGTGTCGGAGTTCGCCCTGGAGAGTGCTTTGGCC

TCCTGGGAGTGAATGGTGCCGGCAAAACAACCACATTCAAGATGCTCACTGGGGACACCACA

GTGACCTCAGGGGATGCCACCGTAGCAGGCAAGAGTATTTTAACCAATATTTCTGAAGTCCA

TCAAAATATGGGCTACTGTCCTCAGTTTGATGCAATCGATGAGCTGCTCACAGGACGAGAAC

ATCTTTACCTTTATGCCCGGCTTCGAGGTGTACCAGCAGAAGAAATCGAAAAGGTTGCAAAC

TGGAGTATTAAGAGCCTGGGCCTGACTGTCTACGCCGACTGCCTGGCTGGCACGTACAGTGG

GGGCAACAAGCGGAAACTCTCCACAGCCATCGCACTCATTGGCTGCCCACCGCTGGTGCTGC

TGGATGAGCCCACCACAGGGATGGACCCCCAGGCACGCCGCATGCTGTGGAACGTCATCGTG

AGCATCATCAGAGAAGGGAGGGCTGTGGTCCTCACATCCCACAGCATGGAAGAATGTGAGGC

ACTGTGTACCCGGCTGGCCATCATGGTAAAGGGCGCCTTTCGATGTATGGGCACCATTCAGC

ATCTCAAGTCCAAATTTGGAGATGGCTATATCGTCACAATGAAGATCAAATCCCCGAAGGAC

GACCTGCTTCCTGACCTGAACCCTGTGGAGCAGTTCTTCCAGGGGAACTTCCCAGGCAGTGT

GCAGAGGGAGAGGCACTACAACATGCTCCAGTTCCAGGTCTCCTCCTCCTCCCTGGCGAGGA

TCTTCCAGCTCCTCCTCTCCCACAAGGACAGCCTGCTCATCGAGGAGTACTCAGTCACACAG

ACCACACTGGACCAGGTGTTTGTAAATTTTGCTAAACAGCAGACTGAAAGTCATGACCTCCC

TCTGCACCCTCGAGCTGCTGGAGCCAGTCGACAAGCCCAGGACTGAGCGGCCGCTTCGAGCA

GACATGATAAGATACATTGATGAGTTTGGACAAACCACAACTAGAATGCAGTGAAAAAAATG

CTTTATTTGTGAAATTTGTGATGCTATTGCTTTATTTGTAACCATTATAAGCTGCAATAAAC

-continued

AAGTTAACAACAACAATTGCATTCATTTTATGTTTCAGGTTCAGGGGGAGATGTGGGAGGTT

TTTTAAAGCAAGTAAAACCTCTACAAATGTGGTAAAATCGATAAGGATCTTCCTAGAGCATG

GCTACGTAGATAAGTAGCATGGCGGGTTAATCATTAACTACAAGGAACCCCTAGTGATGGAG

TTGGCCACTCCCTCTCTGCGCGCTCGCTCGCTCACTGAGGCCGGGCGACCAAAGGTCGCCCG

ACGCCCGGGCTTTGCCCGGGCGGCCTCAGTGAGCGAGCGAGCGCGCAG pZac2.1-CMV-ABCA4_5'TS
Full length sequence of pZac2.1-CMV-ABCA4_5'TS (SEQ ID No. 16)

CTGCGCGCTCGCTCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACTCCATCACTAGGG

GTTCCTTGTAGTTAATGATTAACCCGCCATGCTACTTATCTACGTAGCCATGCTCTAGGAAG

ATCTTCAATATTGGCCATTAGCCATATTATTCATTGGTTATATAGCATAAATCAATATTGGC

TATTGGCCATTGCATACGTTGTATCTATATCATAATATGTACATTTATATTGGCTCATGTCC

AATATGACCGCCATGTTGGCATTGATTATTGACTAGTTATTAATAGTAATCAATTACGGGGT

CATTAGTTCATAGCCCATATATGGAGTTCCGCGTTACATAACTTACGGTAAATGGCCCGCCT

GGCTGACCGCCCAACGACCCCCGCCCATTGACGTCAATAATGACGTATGTTCCCATAGTAAC

GCCAATAGGGACTTTCCATTGACGTCAATGGGTGGAGTATTTACGGTAAACTGCCCACTTGG

CAGTACATCAAGTGTATCATATGCCAAGTCCGCCCCCTATTGACGTCAATGACGGTAAATGG

CCCGCCTGGCATTATGCCCAGTACATGACCTTACGGGACTTTCCTACTTGGCAGTACATCTA

CGTATTAGTCATCGCTATTACCATGGTGATGCGGTTTTGGCAGTACACCAATGGGCGTGGAT

AGCGGTTTGACTCACGGGGATTTCCAAGTCTCCACCCCATTGACGTCAATGGGAGTTTGTTT

TGGCACCAAAATCAACGGGACTTTCCAAAATGTCGTAATAACCCCGCCCCGTTGACGCAAAT

GGGCGGTAGGCGTGTACGGTGGGAGGTCTATATAAGCAGAGCTCGTTTAGTGAACCGTCAGA

TCACTAGAAGCTTTATTGCGGTAGTTTATCACAGTTAAATTGCTAACGCAGTCAGTGCTTCT

GACACAACAGTCTCGAACTTAAGCTGCAGAAGTTGGTCGTGAGGCACTGGGCAGGTAAGTAT

CAAGGTTACAAGACAGGTTTAAGGAGACCAATAGAAACTGGGCTTGTCGAGACAGAGAAGAC

TCTTGCGTTTCTGATAGGCACCTATTGGTCTTACTGACATCCACTTTGCCTTTCTCTCCACA

GGTGTCCACTCCCAGTTCAATTACAGCTCTTAAGGCTAGAGTACTTAATACGACTCACTATA

GGCTAGCCTCGAGAATTCACGCGTGGTACCTCTAGAGTCGACCCGGGCGGCCGCCATGGGCT

TCGTGAGACAGATACAGCTTTTGCTCTGGAAGAACTGGACCCTGCGGAAAAGGCAAAAGATT

CGCTTTGTGGTGGAACTCGTGTGGCCTTTATCTTTATTTCTGGTCTTGATCTGGTTAAGGAA

TGCCAACCCGCTCTACAGCCATCATGAATGCCATTTCCCCAACAAGGCGATGCCCTCAGCAG

GAATGCTGCCGTGGCTCCAGGGGATCTTCTGCAATGTGAACAATCCCTGTTTTCAAAGCCCC

ACCCCAGGAGAATCTCCTGGAATTGTGTCAAACTATAACAACTCCATCTTGGCAAGGGTATA

TCGAGATTTTCAAGAACTCCTCATGAATGCACCAGAGAGCCAGCACCTTGGCCGTATTTGGA

CAGAGCTACACATCTTGTCCCAATTCATGGACACCCTCCGGACTCACCCGGAGAGAATTGCA

GGAAGAGGAATTCGAATAAGGGATATCTTGAAAGATGAAGAAACACTGACACTATTTCTCAT

TAAAAACATCGGCCTGTCTGACTCAGTGGTCTACCTTCTGATCAACTCTCAAGTCCGTCCAG

AGCAGTTCGCTCATGGAGTCCCGGACCTGGCGCTGAAGGACATCGCCTGCAGCGAGGCCCTC

CTGGAGCGCTTCATCATCTTCAGCCAGAGACGCGGGGCAAAGACGGTGCGCTATGCCCTGTG

CTCCCTCTCCCAGGGCACCCTACAGTGGATAGAAGACACTCTGTATGCCAACGTGGACTTCT

TCAAGCTCTTCCGTGTGCTTCCCACACTCCTAGACAGCCGTTCTCAAGGTATCAATCTGAGA

-continued

TCTTGGGGAGGAATATTATCTGATATGTCACCAAGAATTCAAGAGTTTATCCATCGGCCGAG

TATGCAGGACTTGCTGTGGGTGACCAGGCCCCTCATGCAGAATGGTGGTCCAGAGACCTTTA

CAAAGCTGATGGGCATCCTGTCTGACCTCCTGTGTGGCTACCCCGAGGGAGGTGGCTCTCGG

GTGCTCTCCTTCAACTGGTATGAAGACAATAACTATAAGGCCTTTCTGGGGATTGACTCCAC

AAGGAAGGATCCTATCTATTCTTATGACAGAAGAACAACATCCTTTTGTAATGCATTGATCC

AGAGCCTGGAGTCAAATCCTTTAACCAAAATCGCTTGGAGGGCGGCAAAGCCTTTGCTGATG

GGAAAAATCCTGTACACTCCTGATTCACCTGCAGCACGAAGGATACTGAAGAATGCCAACTC

AACTTTTGAAGAACTGGAACACGTTAGGAAGTTGGTCAAAGCCTGGGAAGAAGTAGGGCCCC

AGATCTGGTACTTCTTTGACAACAGCACACAGATGAACATGATCAGAGATACCCTGGGGAAC

CCAACAGTAAAAGACTTTTTGAATAGGCAGCTTGGTGAAGAAGGTATTACTGCTGAAGCCAT

CCTAAACTTCCTCTACAAGGGCCCTCGGGAAAGCCAGGCTGACGACATGGCCAACTTCGACT

GGAGGGACATATTTAACATCACTGATCGCACCCTCCGCCTTGTCAATCAATACCTGGAGTGC

TTGGTCCTGGATAAGTTTGAAAGCTACAATGATGAAACTCAGCTCACCCAACGTGCCCTCTC

TCTACTGGAGGAAAACATGTTCTGGGCCGGAGTGGTATTCCCTGACATGTATCCCTGGACCA

GCTCTCTACCACCCCACGTGAAGTATAAGATCCGAATGGACATAGACGTGGTGGAGAAAACC

AATAAGATTAAAGACAGGTATTGGGATTCTGGTCCCAGAGCTGATCCCGTGGAAGATTTCCG

GTACATCTGGGGCGGGTTTGCCTATCTGCAGGACATGGTTGAACAGGGGATCACAAGGAGCC

AGGTGCAGGCGGAGGCTCCAGTTGGAATCTACCTCCAGCAGATGCCCTACCCCTGCTTCGTG

GACGATTCTTTCATGATCATCCTGAACCGCTGTTTCCCTATCTTCATGGTGCTGGCATGGAT

CTACTCTGTCTCCATGACTGTGAAGAGCATCGTCTTGGAGAAGGAGTTGCGACTGAAGGAGA

CCTTGAAAAATCAGGGTGTCTCCAATGCAGTGATTTGGTGTACCTGGTTCCTGGACAGCTTC

TCCATCATGTCGATGAGCATCTTCCTCCTGACGATATTCATCATGCATGGAAGAATCCTACA

TTACAGCGACCCATTCATCCTCTTCCTGTTCTTGTTGGCTTTCTCCACTGCCACCATCATGC

TGTGCTTTCTGCTCAGCACCTTCTTCTCCAAGGCCAGTCTGGCAGCAGCCTGTAGTGGTGTC

ATCTATTTCACCCTCTACCTGCCACACATCCTGTGCTTCGCCTGGCAGGACCGCATGACCGC

TGAGCTGAAGAAGGCTGTGAGCTTACTGTCTCCGGTGGCATTTGGATTTGGCACTGAGTACC

TGGTTCGCTTTGAAGAGCAAGGCCTGGGGCTGCAGTGGAGCAACATCGGGAACAGTCCCACG

GAAGGGGACGAATTCAGCTTCCTGCTGTCCATGCAGATGATGCTCCTTGATGCTGCTGTCTA

TGGCTTACTCGCTTGGTACCTTGATCAGGTGTTTCCAGGAGACTATGGAACCCCACTTCCTT

GGTACTTTCTTCTACAAGAGTCGTATTGGCTTGGCGGTGAAGGGTGTTCAACCAGAGAAGAA

AGAGCCCTGGAAAAGACCGAGCCCCTAACAGAGGAAACGGAGGATCCAGAGCACCCAGAAGG

AATACACGACTCCTTCTTTGAACGTGAGCATCCAGGGTGGGTTCCTGGGGTATGCGTGAAGA

ATCTGGTAAAGATTTTTGAGCCCTGTGGCCGGCCAGCTGTGGACCGTCTGAACATCACCTTC

TACGAGAACCAGATCACCGCATTCCTGGGCCACAATGGAGCTGGGAAAACCACCACCTTGTA

AGTATCAAGGTTACAAGACAGGTTTAAGGAGACCAATAGAAACTGGGCTTGTCGAGACAGAG

AAGACTCTTGCGTTTCTCAATTGAGGAACCCCTAGTGATGGAGTTGGCCACTCCCTCTCTGC

GCGCTCGCTCGCTCACTGAGGCCGGGCGACCAAAGGTCGCCCGACGCCCGGGCTTTGCCCGG

GCGGCCTCAGTGAGCGAGCGAGCGCGCAG

-continued pZac2.1-ABCA4_3'TS_SV40

Full length sequence of pZac2.1-ABCA4_3'TS_SV40

(SEQ ID No. 17)

CTGCGCGCTCGCTCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACTCCATCACTAGGG

GTTCCTGATAGGCACCTATTGGTCTTACTGACATCCACTTTGCCTTTCTCTCCACAGGTCCA

TCCTGACGGGTCTGTTGCCACCAACCTCTGGGACTGTGCTCGTTGGGGGAAGGGACATTGAA

ACCAGCCTGGATGCAGTCCGGCAGAGCCTTGGCATGTGTCCACAGCACAACATCCTGTTCCA

CCACCTCACGGTGGCTGAGCACATGCTGTTCTATGCCCAGCTGAAAGGAAAGTCCCAGGAGG

AGGCCCAGCTGGAGATGGAAGCCATGTTGGAGGACACAGGCCTCCACCACAAGCGGAATGAA

GAGGCTCAGGACCTATCAGGTGGCATGCAGAGAAAGCTGTCGGTTGCCATTGCCTTTGTGGG

AGATGCCAAGGTGGTGATTCTGGACGAACCCACCTCTGGGGTGGACCCTTACTCGAGACGCT

CAATCTGGGATCTGCTCCTGAAGTATCGCTCAGGCAGAACCATCATCATGTCCACTCACCAC

ATGGACGAGGCCGACCTCCTTGGGGACCGCATTGCCATCATTGCCCAGGGAAGGCTCTACTG

CTCAGGCACCCCACTCTTCCTGAAGAACTGCTTTGGCACAGGCTTGTACTTAACCTTGGTGC

GCAAGATGAAAAACATCCAGAGCCAAAGGAAAGGCAGTGAGGGGACCTGCAGCTGCTCGTCT

AAGGGTTTCTCCACCACGTGTCCAGCCCACGTCGATGACCTAACTCCAGAACAAGTCCTGGA

TGGGGATGTAAATGAGCTGATGGATGTAGTTCTCCACCATGTTCCAGAGGCAAAGCTGGTGG

AGTGCATTGGTCAAGAACTTATCTTCCTTCTTCCAAATAAGAACTTCAAGCACAGAGCATAT

GCCAGCCTTTTCAGAGAGCTGGAGGAGACGCTGGCTGACCTTGGTCTCAGCAGTTTTGGAAT

TTCTGACACTCCCCTGGAAGAGATTTTTCTGAAGGTCACGGAGGATTCTGATTCAGGACCTC

TGTTTGCGGGTGGCGCTCAGCAGAAAAGAGAAAACGTCAACCCCCGACACCCCTGCTTGGGT

CCCAGAGAGAAGGCTGGACAGACACCCCAGGACTCCAATGTCTGCTCCCCAGGGGCGCCGGC

TGCTCACCCAGAGGGCCAGCCTCCCCCAGAGCCAGAGTGCCCAGGCCCGCAGCTCAACACGG

GGACACAGCTGGTCCTCCAGCATGTGCAGGCGCTGCTGGTCAAGAGATTCCAACACACCATC

CGCAGCCACAAGGACTTCCTGGCGCAGATCGTGCTCCCGGCTACCTTTGTGTTTTTGGCTCT

GATGCTTTCTATTGTTATCCCTCCTTTTGGCGAATACCCCGCTTTGACCCTTCACCCCTGGA

TATATGGGCAGCAGTACACCTTCTTCAGCATGGATGAACCAGGCAGTGAGCAGTTCACGGTA

CTTGCAGACGTCCTCCTGAATAAGCCAGGCTTTGGCAACCGCTGCCTGAAGGAAGGGTGGCT

TCCGGAGTACCCCTGTGGCAACTCAACACCCTGGAAGACTCCTTCTGTGTCCCCAAACATCA

CCCAGCTGTTCCAGAAGCAGAAATGGACACAGGTCAACCCTTCACCATCCTGCAGGTGCAGC

ACCAGGGAGAAGCTCACCATGCTGCCAGAGTGCCCCGAGGGTGCCGGGGGCCTCCCGCCCCC

CCAGAGAACACAGCGCAGCACGGAAATTCTACAAGACCTGACGGACAGGAACATCTCCGACT

TCTTGGTAAAAACGTATCCTGCTCTTATAAGAAGCAGCTTAAAGAGCAAATTCTGGGTCAAT

GAACAGAGGTATGGAGGAATTTCCATTGGAGGAAAGCTCCCAGTCGTCCCCATCACGGGGGA

AGCACTTGTTGGGTTTTTAAGCGACCTTGGCCGGATCATGAATGTGAGCGGGGGCCCTATCA

CTAGAGAGGCCTCTAAAGAAATACCTGATTTCCTTAAACATCTAGAAACTGAAGACAACATT

AAGGTGTGGTTTAATAACAAAGGCTGGCATGCCCTGGTCAGCTTTCTCAATGTGGCCCACAA

CGCCATCTTACGGGCCAGCCTGCCTAAGGACAGAAGCCCCGAGGAGTATGGAATCACCGTCA

TTAGCCAACCCCTGAACCTGACCAAGGAGCAGCTCTCAGAGATTACAGTGCTGACCACTTCA

GTGGATGCTGTGGTTGCCATCTGCGTGATTTTCTCCATGTCCTTCGTCCCAGCCAGCTTTGT

CCTTTATTTGATCCAGGAGCGGGTGAACAAATCCAAGCACCTCCAGTTTATCAGTGGAGTGA

-continued

GCCCCACCACCTACTGGGTAACCAACTTCCTCTGGGACATCATGAATTATTCCGTGAGTGCT

GGGCTGGTGGTGGGCATCTTCATCGGGTTTCAGAAGAAAGCCTACACTTCTCCAGAAAACCT

TCCTGCCCTTGTGGCACTGCTCCTGCTGTATGGATGGGCGGTCATTCCCATGATGTACCCAG

CATCCTTCCTGTTTGATGTCCCCAGCACAGCCTATGTGGCTTTATCTTGTGCTAATCTGTTC

ATCGGCATCAACAGCAGTGCTATTACCTTCATCTTGGAATTATTTGAGAATAACCGGACGCT

GCTCAGGTTCAACGCCGTGCTGAGGAAGCTGCTCATTGTCTTCCCCCACTTCTGCCTGGGCC

GGGGCCTCATTGACCTTGCACTGAGCCAGGCTGTGACAGATGTCTATGCCCGGTTTGGTGAG

GAGCACTCTGCAAATCCGTTCCACTGGGACCTGATTGGGAAGAACCTGTTTGCCATGGTGGT

GGAAGGGGTGGTGTACTTCCTCCTGACCCTGCTGGTCCAGCGCCACTTCTTCCTCTCCCAAT

GGATTGCCGAGCCCACTAAGGAGCCCATTGTTGATGAAGATGATGATGTGGCTGAAGAAAGA

CAAAGAATTATTACTGGTGGAAATAAAACTGACATCTTAAGGCTACATGAACTAACCAAGAT

TTATCCAGGCACCTCCAGCCCAGCAGTGGACAGGCTGTGTGTCGGAGTTCGCCCTGGAGAGT

GCTTTGGCCTCCTGGGAGTGAATGGTGCCGGCAAAACAACCACATTCAAGATGCTCACTGGG

GACACCACAGTGACCTCAGGGGATGCCACCGTAGCAGGCAAGAGTATTTTAACCAATATTTC

TGAAGTCCATCAAAATATGGGCTACTGTCCTCAGTTTGATGCAATCGATGAGCTGCTCACAG

GACGAGAACATCTTTACCTTTATGCCCGGCTTCGAGGTGTACCAGCAGAAGAAATCGAAAAG

GTTGCAAACTGGAGTATTAAGAGCCTGGGCCTGACTGTCTACGCCGACTGCCTGGCTGGCAC

GTACAGTGGGGGCAACAAGCGGAAACTCTCCACAGCCATCGCACTCATTGGCTGCCCACCGC

TGGTGCTGCTGGATGAGCCCACCACAGGGATGGACCCCCAGGCACGCCGCATGCTGTGGAAC

GTCATCGTGAGCATCATCAGAGAAGGGAGGGCTGTGGTCCTCACATCCCACAGCATGGAAGA

ATGTGAGGCACTGTGTACCCGGCTGGCCATCATGGTAAAGGGCGCCTTTCGATGTATGGGCA

CCATTCAGCATCTCAAGTCCAAATTTGGAGATGGCTATATCGTCACAATGAAGATCAAATCC

CCGAAGGACGACCTGCTTCCTGACCTGAACCCTGTGGAGCAGTTCTTCCAGGGGAACTTCCC

AGGCAGTGTGCAGAGGGAGAGGCACTACAACATGCTCCAGTTCCAGGTCTCCTCCTCCTCCC

TGGCGAGGATCTTCCAGCTCCTCCTCTCCCACAAGGACAGCCTGCTCATCGAGGAGTACTCA

GTCACACAGACCACACTGGACCAGGTGTTTGTAAATTTTGCTAAACAGCAGACTGAAAGTCA

TGACCTCCCTCTGCACCCTCGAGCTGCTGGAGCCAGTCGACAAGCCCAGGACTGAGCGGCCG

CTTCGAGCAGACATGATAAGATACATTGATGAGTTTGGACAAACCACAACTAGAATGCAGTG

AAAAAAATGCTTTATTTGTGAAATTTGTGATGCTATTGCTTTATTTGTAACCATTATAAGCT

GCAATAAACAAGTTAACAACAACAATTGCATTCATTTTATGTTTCAGGTTCAGGGGGAGATG

TGGGAGGTTTTTTAAAGCAAGTAAAACCTCTACAAATGTGGTAAAATCGATAAGGATCTTCC

TAGAGCATGGCTACGTAGATAAGTAGCATGGCGGGTTAATCATTAACTACAAGGAACCCCTA

GTGATGGAGTTGGCCACTCCCTCTCTGCGCGCTCGCTCGCTCACTGAGGCCGGGCGACCAAA

GGTCGCCCGACGCCCGGGCTTTGCCCGGGCGGCCTCAGTGAGCGAGCGAGCGCGCAG

MYO7A
pAAV2.1-CBA-MYO7A_5'AK
5' ITR2

(SEQ ID No. 10)

AGGAACCCCTAGTGATGGAGTTGGCCACTCCCTCTCTGCGCGCTCGCTCGCTCACTGAGGCC

GGGCGACCAAAGGTCGCCCGACGCCCGGGCTTTGCCCGGGCGGCCTCAGTGAGCGAGCGAGC

GCGCAG

-continued

LEFT ITR5

(SEQ ID No. 18)

CTCTCCCCCCTGTCGCGTTCGCTCGCTCGCTGGCTCGTTTGGGGGGGTGGCAGCTCAAAGAG

CTGCCAGACGACGGCCCTCTGGCCGTCGCCCCCCCAAACGAGCCAGCGAGCGAGCGAACGCG

ACAGGGGGGAGAGTGCCACACTCTCAAGCAAGGGGGTTTTGTAAGCAGTGA

CMV enhancer (SEQ ID No. 19)

GCTAGCGTGCCACCTGGTCGACATTGATTATTGACTAGTTATTAATAGTAATCAATTACGGG

GTCATTAGTTCATAGCCCATATATGGAGTTCCGCGTTACATAACTTACGGTAAATGGCCCGC

CTGGCTGACCGCCCAACGACCCCCGCCCATTGACGTCAATAATGACGTATGTTCCCATAGTA

ACGCCAATAGGGACTTTCCATTGACGTCAATGGGTGGACTATTTACGGTAAACTGCCCACTT

GGCAGTACATCAAGTGTATCATATGCCAAGTACGCCCCCTATTGACGTCAATGACGGTAAAT

GGCCCGCCTGGCATTATGCCCAGTACATGACCTTATGGGACTTTCCTACTTGGCAGTACATC

TACGTATTAGTCATCGCTATTACCATGG

CBA promoter (SEQ ID No. 20)

TCGAGGTGAGCCCCACGTTCTGCTTCACTCTCCCCATCTCCCCCCCCTCCCCACCCCCAATT

TTGTATTTATTTATTTTTTAATTATTTTGTGCAGCGATGGGGGCGGGGGGGGGGGGGGCGCG

CGCCAGGCGGGGCGGGGCGGGGCGAGGGGCGGGGCGGGGCGAGGCGGAGAGGTGCGGCGGCA

GCCAATCAGAGCGGCGCGCTCCGAAAGTTTCCTTTTATGGCGAGGCGGCGGCGGCGGCGGCC

CTATAAAAAGCGAAGCGCGCGGCGGGCGG

SV40 intron (SEQ ID No. 21)

GTAAGTATCAAGGTTACAAGACAGGTTTAAGGAGACCAATAGAAACTGGGCTTGTCGAGACA

GAGAAGACTCTTGCGTTTCTGATAGGCACCTATTGGTCTTACTGACATCCACTTTGCCTTTC

TCTCCACAG

5'hMYO7A CDS (SEQ ID No. 22)

ATGGTGATTCTTCAGCAGGGGGACCATGTGTGGATGGACCTGAGATTGGGGCAGGAGTTCGA

CGTGCCCATCGGGGCGGTGGTGAAGCTCTGCGACTCTGGGCAGGTCCAGGTGGTGGATGATG

AAGACAATGAACACTGGATCTCTCCGCAGAACGCAACGCACATCAAGCCTATGCACCCCACG

TCGGTCCACGGCGTGGAGGACATGATCCGCCTGGGGGACCTCAACGAGGCGGGCATCTTGCG

CAACCTGCTTATCCGCTACCGGGACCACCTCATCTACACGTATACGGGCTCCATCCTGGTGG

CTGTGAACCCCTACCAGCTGCTCTCCATCTACTCGCCAGAGCACATCCGCCAGTATACCAAC

AAGAAGATTGGGGAGATGCCCCCCCACATCTTTGCCATTGCTGACAACTGCTACTTCAACAT

GAAACGCAACAGCCGAGACCAGTGCTGCATCATCAGTGGGGAATCTGGGGCCGGGAAGACGG

AGAGCACAAAGCTGATCCTGCAGTTCCTGGCAGCCATCAGTGGGCAGCACTCGTGGATTGAG

CAGCAGGTCTTGGAGGCCACCCCCATTCTGGAAGCATTTGGGAATGCCAAGACCATCCGCAA

TGACAACTCAAGCCGTTTCGGAAAGTACATCGACATCCACTTCAACAAGCGGGGCGCCATCG

AGGGCGCGAAGATTGAGCAGTACCTGCTGGAAAAGTCACGTGTCTGTCGCCAGGCCCTGGAT

GAAAGGAACTACCACGTGTTCTACTGCATGCTGGAGGGCATGAGTGAGGATCAGAAGAAGAA

GCTGGGCTTGGGCCAGGCCTCTGACTACAACTACTTGGCCATGGGTAACTGCATAACCTGTG

AGGGCCGGGTGGACAGCCAGGAGTACGCCAACATCCGCTCCGCCATGAAGGTGCTCATGTTC

ACTGACACCGAGAACTGGGAGATCTCGAAGCTCCTGGCTGCCATCCTGCACCTGGGCAACCT

GCAGTATGAGGCACGCACATTTGAAAACCTGGATGCCTGTGAGGTTCTCTTCTCCCCATCGC

-continued

TGGCCACAGCTGCATCCCTGCTTGAGGTGAACCCCCCAGACCTGATGAGCTGCCTGACTAGC

CGCACCCTCATCACCCGCGGGGAGACGGTGTCCACCCCACTGAGCAGGGAACAGGCACTGGA

CGTGCGCGACGCCTTCGTAAAGGGGATCTACGGGCGGCTGTTCGTGTGGATTGTGGACAAGA

TCAACGCAGCAATTTACAAGCCTCCCTCCCAGGATGTGAAGAACTCTCGCAGGTCCATCGGC

CTCCTGGACATCTTTGGGTTTGAGAACTTTGCTGTGAACAGCTTTGAGCAGCTCTGCATCAA

CTTCGCCAATGAGCACCTGCAGCAGTTCTTTGTGCGGCACGTGTTCAAGCTGGAGCAGGAGG

AATATGACCTGGAGAGCATTGACTGGCTGCACATCGAGTTCACTGACAACCAGGATGCCCTG

GACATGATTGCCAACAAGCCCATGAACATCATCTCCCTCATCGATGAGGAGAGCAAGTTCCC

CAAGGGCACAGACACCACCATGTTACACAAGCTGAACTCCCAGCACAAGCTCAACGCCAACT

ACATCCCCCCCAAGAACAACCATGAGACCCAGTTTGGCATCAACCATTTTGCAGGCATCGTC

TACTATGAGACCCAAGGCTTCCTGGAGAAGAACCGAGACACCCTGCATGGGGACATTATCCA

GCTGGTCCACTCCTCCAGGAACAAGTTCATCAAGCAGATCTTCCAGGCCGATGTCGCCATGG

GCGCCGAGACCAGGAAGCGCTCGCCCACACTTAGCAGCCAGTTCAAGCGGTCACTGGAGCTG

CTGATGCGCACGCTGGGTGCCTGCCAGCCCTTCTTTGTGCGATGCATCAAGCCCAATGAGTT

CAAGAAGCCCATGCTGTTCGACCGGCACCTGTGCGTGCGCCAGCTGCGGTACTCAGGAATGA

TGGAGACCATCCGAATCCGCCGAGCTGGCTACCCCATCCGCTACAGCTTCGTAGAGTTTGTG

GAGCGGTACCGTGTGCTGCTGCCAGGTGTGAAGCCGGCCTACAAGCAGGGCGACCTCCGCGG

GACTTGCCAGCGCATGGCTGAGGCTGTGCTGGGCACCCACGATGACTGGCAGATAGGCAAAA

CCAAGATCTTTCTGAAGGACCACCATGACATGCTGCTGGAAGTGGAGCGGGACAAAGCCATC

ACCGACAGAGTCATCCTCCTTCAGAAAGTCATCCGGGGATTCAAAGACAGGTCTAACTTTCT

GAAGCTGAAGAACGCTGCCACACTGATCCAGAGGCACTGGCGGGGTCACAACTGTAGGAAGA

ACTACGGGCTGATGCGTCTGGGCTTCCTGCGGCTGCAGGCCCTGCACCGCTCCCGGAAGCTG

CACCAGCAGTACCGCCTGGCCCGCCAGCGCATCATCCAGTTCCAGGCCCGCTGCCGCGCCTA

TCTGGTGCGCAAGGCCTTCCGCCACCGCCTCTGGGCTGTGCTCACCGTGCAGGCCTATGCCC

GGGGCATGATCGCCCGCAGGCTGCACCAACGCCTCAGGGCTGAGTATCTGTGGCGCCTCGAG

GCTGAGAAAATGCGGCTGGCGGAGGAAGAGAAGCTTCGGAAGGAGATGAGCGCCAAGAAGGC

CAAGGAGGAGGCCGAGCGCAAGCATCAGGAGCGCCTGGCCCAGCTGGCTCGTGAGGACGCTG

AGCGGGAGCTGAAGGAGAAGGAGGCCGCTCGGCGGAAGAAGGAGCTCCTGGAGCAGATGGAA

AGGGCCCGCCATGAGCCTGTCAATCACTCAGACATGGTGGACAAGATGTTTGGCTTCCTGGG

GACTTCAGGTGGCCTGCCAGGCCAGGAGGGCCAGGCACCTAGTGGCTTTGAGGACCTGGAGC

GAGGGCGGAGGGAGATGGTGGAGGAGGACCTGGATGCAGCCCTGCCCCTGCCTGACGAGGAT

GAGGAGGACCTCTCTGAGTATAAATTTGCCAAGTTCGCGGCCACCTACTTCCAGGGGACAAC

TACGCACTCCTACACCCGGCGGCCACTCAAACAGCCACTGCTCTACCATGACGACGAGGGTG

ACCAGCTG

Splice donor signal (SEQ ID No. 1)

GTAAGTATCAAGGTTACAAGACAGGTTTAAGGAGACCAATAGAAACTGGGCTTGTCGAGACA

GAGAAGACTCTTGCGTTTCT

AK (SEQ ID No. 3)

GGGATTTTGCCGATTTCGGCCTATTGGTTAAAAAATGAGCTGATTTAACAAAAATTTAACGC

GAATTTTAACAAAAT

-continued

3'ITR2

(SEQ ID No. 4)

CTGCGCGCTCGCTCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACTCCATCACTAGGG

GTTCCT

Full-sequence of pAAV2.1-CBA-MYO7A_5'AK (SEQ ID No. 23)

CTGCGCGCTCGCTCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACTCCATCACTAGGG

GTTCCTTGTAGTTAATGATTAACCCGCCATGCTACTTATCTACGTAGCCATGCTCTAGGAAG

ATCCTAATCGGGAATTCGCCCTTAAGCTAGCGTGCCACCTGGTCGACATTGATTATTGACTA

GTTATTAATAGTAATCAATTACGGGGTCATTAGTTCATAGCCCATATATGGAGTTCCGCGTT

ACATAACTTACGGTAAATGGCCCGCCTGGCTGACCGCCCAACGACCCCCGCCCATTGACGTC

AATAATGACGTATGTTCCCATAGTAACGCCAATAGGGACTTTCCATTGACGTCAATGGGTGG

ACTATTTACGGTAAACTGCCCACTTGGCAGTACATCAAGTGTATCATATGCCAAGTACGCCC

CCTATTGACGTCAATGACGGTAAATGGCCCGCCTGGCATTATGCCCAGTACATGACCTTATG

GGACTTTCCTACTTGGCAGTACATCTACGTATTAGTCATCGCTATTACCATGGGTCGAGGTG

AGCCCCACGTTCTGCTTCACTCTCCCCATCTCCCCCCCCTCCCCACCCCCAATTTTGTATTT

ATTTATTTTTTAATTATTTTGTGCAGCGATGGGGGCGGGGGGGGGGGGGGCGCGCGCCAGGC

GGGGCGGGGCGGGGCGAGGGGCGGGGCGGGGCGAGGCGGAGAGGTGCGGCGGCAGCCAATCA

GAGCGGCGCGCTCCGAAAGTTTCCTTTTATGGCGAGGCGGCGGCGGCGGCGGCCCTATAAAA

AGCGAAGCGCGCGGCGGGCGGCTGCAGAAGTTGGTCGTGAGGCACTGGGCAGGTAAGTATCA

AGGTTACAAGACAGGTTTAAGGAGACCAATAGAAACTGGGCTTGTCGAGACAGAGAAGACTC

TTGCGTTTCTGATAGGCACCTATTGGTCTTACTGACATCCACTTTGCCTTTCTCTCCACAGG

TGTCCAGGCGGCCGCCATGGTGATTCTTCAGCAGGGGGACCATGTGTGGATGGACCTGAGAT

TGGGGCAGGAGTTCGACGTGCCCATCGGGGCGGTGGTGAAGCTCTGCGACTCTGGGCAGGTC

CAGGTGGTGGATGATGAAGACAATGAACACTGGATCTCTCCGCAGAACGCAACGCACATCAA

GCCTATGCACCCCACGTCGGTCCACGGCGTGGAGGACATGATCCGCCTGGGGGACCTCAACG

AGGCGGGCATCTTGCGCAACCTGCTTATCCGCTACCGGGACCACCTCATCTACACGTATACG

GGCTCCATCCTGGTGGCTGTGAACCCCTACCAGCTGCTCTCCATCTACTCGCCAGAGCACAT

CCGCCAGTATACCAACAAGAAGATTGGGGAGATGCCCCCCCACATCTTTGCCATTGCTGACA

ACTGCTACTTCAACATGAAACGCAACAGCCGAGACCAGTGCTGCATCATCAGTGGGGAATCT

GGGGCCGGGAAGACGGAGAGCACAAAGCTGATCCTGCAGTTCCTGGCAGCCATCAGTGGGCA

GCACTCGTGGATTGAGCAGCAGGTCTTGGAGGCCACCCCCATTCTGGAAGCATTTGGGAATG

CCAAGACCATCCGCAATGACAACTCAAGCCGTTTCGGAAAGTACATCGACATCCACTTCAAC

AAGCGGGGCGCCATCGAGGGCGCGAAGATTGAGCAGTACCTGCTGGAAAAGTCACGTGTCTG

TCGCCAGGCCCTGGATGAAAGGAACTACCACGTGTTCTACTGCATGCTGGAGGGCATGAGTG

AGGATCAGAAGAAGAAGCTGGGCTTGGGCCAGGCCTCTGACTACAACTACTTGGCCATGGGT

AACTGCATAACCTGTGAGGGCCGGGTGGACAGCCAGGAGTACGCCAACATCCGCTCCGCCAT

GAAGGTGCTCATGTTCACTGACACCGAGAACTGGGAGATCTCGAAGCTCCTGGCTGCCATCC

TGCACCTGGGCAACCTGCAGTATGAGGCACGCACATTTGAAAACCTGGATGCCTGTGAGGTT

CTCTTCTCCCCATCGCTGGCCACAGCTGCATCCCTGCTTGAGGTGAACCCCCCAGACCTGAT

-continued

GAGCTGCCTGACTAGCCGCACCCTCATCACCCGCGGGGAGACGGTGTCCACCCCACTGAGCA

GGGAACAGGCACTGGACGTGCGCGACGCCTTCGTAAAGGGGATCTACGGGCGGCTGTTCGTG

TGGATTGTGGACAAGATCAACGCAGCAATTTACAAGCCTCCCTCCCAGGATGTGAAGAACTC

TCGCAGGTCCATCGGCCTCCTGGACATCTTTGGGTTTGAGAACTTTGCTGTGAACAGCTTTG

AGCAGCTCTGCATCAACTTCGCCAATGAGCACCTGCAGCAGTTCTTTGTGCGGCACGTGTTC

AAGCTGGAGCAGGAGGAATATGACCTGGAGAGCATTGACTGGCTGCACATCGAGTTCACTGA

CAACCAGGATGCCCTGGACATGATTGCCAACAAGCCCATGAACATCATCTCCCTCATCGATG

AGGAGAGCAAGTTCCCCAAGGGCACAGACACCACCATGTTACACAAGCTGAACTCCCAGCAC

AAGCTCAACGCCAACTACATCCCCCCCAAGAACAACCATGAGACCCAGTTTGGCATCAACCA

TTTTGCAGGCATCGTCTACTATGAGACCCAAGGCTTCCTGGAGAAGAACCGAGACACCCTGC

ATGGGGACATTATCCAGCTGGTCCACTCCTCCAGGAACAAGTTCATCAAGCAGATCTTCCAG

GCCGATGTCGCCATGGGCGCCGAGACCAGGAAGCGCTCGCCCACACTTAGCAGCCAGTTCAA

GCGGTCACTGGAGCTGCTGATGCGCACGCTGGGTGCCTGCCAGCCCTTCTTTGTGCGATGCA

TCAAGCCCAATGAGTTCAAGAAGCCCATGCTGTTCGACCGGCACCTGTGCGTGCGCCAGCTG

CGGTACTCAGGAATGATGGAGACCATCCGAATCCGCCGAGCTGGCTACCCCATCCGCTACAG

CTTCGTAGAGTTTGTGGAGCGGTACCGTGTGCTGCTGCCAGGTGTGAAGCCGGCCTACAAGC

AGGGCGACCTCCGCGGGACTTGCCAGCGCATGGCTGAGGCTGTGCTGGGCACCCACGATGAC

TGGCAGATAGGCAAAACCAAGATCTTTCTGAAGGACCACCATGACATGCTGCTGGAAGTGGA

GCGGGACAAAGCCATCACCGACAGAGTCATCCTCCTTCAGAAAGTCATCCGGGGATTCAAAG

ACAGGTCTAACTTTCTGAAGCTGAAGAACGCTGCCACACTGATCCAGAGGCACTGGCGGGGT

CACAACTGTAGGAAGAACTACGGGCTGATGCGTCTGGGCTTCCTGCGGCTGCAGGCCCTGCA

CCGCTCCCGGAAGCTGCACCAGCAGTACCGCCTGGCCCGCCAGCGCATCATCCAGTTCCAGG

CCCGCTGCCGCGCCTATCTGGTGCGCAAGGCCTTCCGCCACCGCCTCTGGGCTGTGCTCACC

GTGCAGGCCTATGCCCGGGGCATGATCGCCCGCAGGCTGCACCAACGCCTCAGGGCTGAGTA

TCTGTGGCGCCTCGAGGCTGAGAAAATGCGGCTGGCGGAGGAAGAGAAGCTTCGGAAGGAGA

TGAGCGCCAAGAAGGCCAAGGAGGAGGCCGAGCGCAAGCATCAGGAGCGCCTGGCCCAGCTG

GCTCGTGAGGACGCTGAGCGGGAGCTGAAGGAGAAGGAGGCCGCTCGGCGGAAGAAGGAGCT

CCTGGAGCAGATGGAAAGGGCCCGCCATGAGCCTGTCAATCACTCAGACATGGTGGACAAGA

TGTTTGGCTTCCTGGGGACTTCAGGTGGCCTGCCAGGCCAGGAGGGCCAGGCACCTAGTGGC

TTTGAGGACCTGGAGCGAGGGCGGAGGGAGATGGTGGAGGAGGACCTGGATGCAGCCCTGCC

CCTGCCTGACGAGGATGAGGAGGACCTCTCTGAGTATAAATTTGCCAAGTTCGCGGCCACCT

ACTTCCAGGGGACAACTACGCACTCCTACACCCGGCGGCCACTCAAACAGCCACTGCTCTAC

CATGACGACGAGGGTGACCAGCTGGTAAGTATCAAGGTTACAAGACAGGTTTAAGGAGACCA

ATAGAAACTGGGCTTGTCGAGACAGAGAAGACTCTTGCGTTTCTGGGATTTTGCCGATTTCG

GCCTATTGGTTAAAAAATGAGCTGATTTAACAAAAATTTAACGCGAATTTTAACAAAATATT

AACGTTTATAATTTCAGGTGGCATCTTTCCAATTGAAGGGCGAATTCCGATCTTCCTAGAGC

ATGGCTACGTAGATAAGTAGCATGGCGGGTTAATCATTAACTACAAGGAACCCCTAGTGATG

GAGTTGGCCACTCCCTCTCTGCGCGCTCGCTCGCTCACTGAGGCCGGGCGACCAAAGGTCGC

CCGACGCCCGGGCTTTGCCCGGGCGGCCTCAGTGAGCGAGCGAGCGCGCAG

-continued pAAV2.1-MYO7A_3'AK_BGH
5' ITR2

(SEQ ID No. 10)
AGGAACCCCTAGTGATGGAGTTGGCCACTCCCTCTCTGCGCGCTCGCTCGCTCACTGAGGCC

GGGCGACCAAAGGTCGCCCGACGCCCGGGCTTTGCCCGGGCGGCCTCAGTGAGCGAGCGAGC

GCGCAG

AK (SEQ ID No. 3)
GGGATTTTGCCGATTTCGGCCTATTGGTTAAAAAATGAGCTGATTTAACAAAAATTTAACGC

GAATTTTAACAAAAT

Splice acceptor signal (SEQ ID No. 1)
GATAGGCACCTATTGGTCTTACTGACATCCACTTTGCCTTTCTCTCCACAG 3'hMYO7A CDS (SEQ ID No. 24)
GCAGCCCTGGCGGTCTGGATCACCATCCTCCGCTTCATGGGGGACCTCCCTGAGCCCAAGTA

CCACACAGCCATGAGTGATGGCAGTGAGAAGATCCCTGTGATGACCAAGATTTATGAGACCC

TGGGCAAGAAGACGTACAAGAGGGAGCTGCAGGCCCTGCAGGGCGAGGGCGAGGCCCAGCTC

CCCGAGGGCCAGAAGAAGAGCAGTGTGAGGCACAAGCTGGTGCATTTGACTCTGAAAAAGAA

GTCCAAGCTCACAGAGGAGGTGACCAAGAGGCTGCATGACGGGGAGTCCACAGTGCAGGGCA

ACAGCATGCTGGAGGACCGGCCCACCTCCAACCTGGAGAAGCTGCACTTCATCATCGGCAAT

GGCATCCTGCGGCCAGCACTCCGGGACGAGATCTACTGCCAGATCAGCAAGCAGCTGACCCA

CAACCCCTCCAAGAGCAGCTATGCCCGGGGCTGGATTCTCGTGTCTCTCTGCGTGGGCTGTT

TCGCCCCCTCCGAGAAGTTTGTCAAGTACCTGCGGAACTTCATCCACGGGGGCCCGCCCGGC

TACGCCCCGTACTGTGAGGAGCGCCTGAGAAGGACCTTTGTCAATGGGACACGGACACAGCC

GCCCAGCTGGCTGGAGCTGCAGGCCACCAAGTCCAAGAAGCCAATCATGTTGCCCGTGACAT

TCATGGATGGGACCACCAAGACCCTGCTGACGGACTCGGCAACCACGGCCAAGGAGCTCTGC

AACGCGCTGGCCGACAAGATCTCTCTCAAGGACCGGTTCGGGTTCTCCCTCTACATTGCCCT

GTTTGACAAGGTGTCCTCCCTGGGCAGCGGCAGTGACCACGTCATGGACGCCATCTCCCAGT

GCGAGCAGTACGCCAAGGAGCAGGGCGCCCAGGAGCGCAACGCCCCCTGGAGGCTCTTCTTC

CGCAAAGAGGTCTTCACGCCCTGGCACAGCCCCTCCGAGGACAACGTGGCCACCAACCTCAT

CTACCAGCAGGTGGTGCGAGGAGTCAAGTTTGGGGAGTACAGGTGTGAGAAGGAGGACGACC

TGGCTGAGCTGGCCTCCCAGCAGTACTTTGTAGACTATGGCTCTGAGATGATCCTGGAGCGC

CTCCTGAACCTCGTGCCCACCTACATCCCCGACCGCGAGATCACGCCCCTGAAGACGCTGGA

GAAGTGGGCCCAGCTGGCCATCGCCGCCCACAAGAAGGGGATTTATGCCCAGAGGAGAACTG

ATGCCCAGAAGGTCAAAGAGGATGTGGTCAGTTATGCCCGCTTCAAGTGGCCCTTGCTCTTC

TCCAGGTTTTATGAAGCCTACAAATTCTCAGGCCCCAGTCTCCCCAAGAACGACGTCATCGT

GGCCGTCAACTGGACGGGTGTGTACTTTGTGGATGAGCAGGAGCAGGTACTTCTGGAGCTGT

CCTTCCCAGAGATCATGGCCGTGTCCAGCAGCAGGGAGTGCCGTGTCTGGCTCTCACTGGGC

TGCTCTGATCTTGGCTGTGCTGCGCCTCACTCAGGCTGGGCAGGACTGACCCCGGCGGGGCC

CTGTTCTCCGTGTTGGTCCTGCAGGGGAGCGAAAACGACGGCCCCCAGCTTCACGCTGGCCA

CCATCAAGGGGGACGAATACACCTTCACCTCCAGTAATGCTGAGGACATTCGTGACCTGGTG

GTCACCTTCCTAGAGGGGCTCCGGAAGAGATCTAAGTATGTTGTGGCCCTGCAGGATAACCC

CAACCCCGCAGGCGAGGAGTCAGGCTTCCTCAGCTTTGCCAAGGGAGACCTCATCATCCTGG

ACCATGACACGGGCGAGCAGGTCATGAACTCGGGCTGGGCCAACGGCATCAATGAGAGGACC

-continued

AAGCAGCGTGGGGACTTCCCCACCGACTGTGTGTACGTCATGCCCACTGTCACCATGCCACC

TCGTGAGATTGTGGCCCTGGTCACCATGACTCCCGATCAGAGGCAGGACGTTGTCCGGCTCT

TGCAGCTGCGAACGGCGGAGCCCGAGGTGCGTGCCAAGCCCTACACGCTGGAGGAGTTTTCC

TATGACTACTTCAGGCCCCCACCCAAGCACACGCTGAGCCGTGTCATGGTGTCCAAGGCCCG

AGGCAAGGACCGGCTGTGGAGCCACACGCGGGAACCGCTCAAGCAGGCGCTGCTCAAGAAGC

TCCTGGGCAGTGAGGAGCTCTCGCAGGAGGCCTGCCTGGCCTTCATTGCTGTGCTCAAGTAC

ATGGGCGACTACCCGTCCAAGAGGACACGCTCCGTCAATGAGCTCACCGACCAGATCTTTGA

GGGTCCCCTGAAAGCCGAGCCCCTGAAGGACGAGGCATATGTGCAGATCCTGAAGCAGCTGA

CCGACAACCACATCAGGTACAGCGAGGAGCGGGGTTGGGAGCTGCTCTGGCTGTGCACGGGC

CTTTTCCCACCCAGCAACATCCTCCTGCCCCACGTGCAGCGCTTCCTGCAGTCCCGAAAGCA

CTGCCCACTCGCCATCGACTGCCTGCAACGGCTCCAGAAAGCCCTGAGAAACGGGTCCCGGA

AGTACCCTCCGCACCTGGTGGAGGTGGAGGCCATCCAGCACAAGACCACCCAGATTTTCCAC

AAGGTCTACTTCCCTGATGACACTGACGAGGCCTTCGAAGTGGAGTCCAGCACCAAGGCCAA

GGACTTCTGCCAGAACATCGCCACCAGGCTGCTCCTCAAGTCCTCAGAGGGATTCAGCCTCT

TTGTCAAAATTGCAGACAAGGTCATCAGCGTTCCTGAGAATGACTTCTTCTTTGACTTTGTT

CGACACTTGACAGACTGGATAAAGAAAGCTCGGCCCATCAAGGACGGAATTGTGCCCTCACT

CACCTACCAGGTGTTCTTCATGAAGAAGCTGTGGACCACCACGGTGCCAGGGAAGGATCCCA

TGGCCGATTCCATCTTCCACTATTACCAGGAGTTGCCCAAGTATCTCCGAGGCTACCACAAG

TGCACGCGGGAGGAGGTGCTGCAGCTGGGGGCGCTGATCTACAGGGTCAAGTTCGAGGAGGA

CAAGTCCTACTTCCCCAGCATCCCCAAGCTGCTGCGGGAGCTGGTGCCCCAGGACCTTATCC

GGCAGGTCTCACCTGATGACTGGAAGCGGTCCATCGTCGCCTACTTCAACAAGCACGCAGGG

AAGTCCAAGGAGGAGGCCAAGCTGGCCTTCCTGAAGCTCATCTTCAAGTGGCCCACCTTTGG

CTCAGCCTTCTTCGAGGTGAAGCAAACTACGGAGCCAAACTTCCCTGAGATCCTCCTAATTG

CCATCAACAAGTATGGGGTCAGCCTCATCGATCCCAAAACGAAGGATATCCTCACCACTCAT

CCCTTCACCAAGATCTCCAACTGGAGCAGCGGCAACACCTACTTCCACATCACCATTGGGAA

CTTGGTGCGCGGGAGCAAACTGCTCTGCGAGACGTCACTGGGCTACAAGATGGATGACCTCC

TGACTTCCTACATTAGCCAGATGCTCACAGCCATGAGCAAACAGCGGGGCTCCAGGAGCGGC

AAGTGA

BGH poly A (SEQ ID No. 25)

GCCTCGACTGTGCCTTCTAGTTGCCAGCCATCTGTTGTTTGCCCCTCCCCCGTGCCTTCCTT

GACCCTGGAAGGTGCCACTCCCACTGTCCTTTCCTAATAAAATGAGGAAATTGCATCGCATT

GTCTGAGTAGGTGTCATTCTATTCTGGGGGGTGGGGTGGGGCAGGACAGCAAGGGGGAGGAT

TGGGAAGACAATAGCAGGCATGCTGGGGA

3'ITR2

(SEQ ID No. 4)

CTGCGCGCTCGCTCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACTCCATCACTAGGG

GTTCCT

-continued

RIGHT ITR5

(SEQ ID No. 14)

TCACTGCTTACAAAACCCCCTTGCTTGAGAGTGTGGCACTCTCCCCCCTGTCGCGTTCGCTC

GCTCGCTGGCTCGTTTGGGGGGGCGACGGCCAGAGGGCCGTCGTCTGGCAGCTCTTTGAGCT

GCCACCCCCCCAAACGAGCCAGCGAGCGAGCGAACGCGACAGGGGGGAGAG

Full-sequence of pAAV2.1-MYO7A_3'AK_BGH (SEQ ID No. 26)

CTGCGCGCTCGCTCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACTCCATCACTAGGG

GTTCCTTGTAGTTAATGATTAACCCGCCATGCTACTTATCTACGTAGCCATGCTCTAGGAAG

ATCGGAATTCGCCCTTTGATCAGGGATTTTGCCGATTTCGGCCTATTGGTTAAAAAATGAGC

TGATTTAACAAAAATTTAACGCGAATTTTAACAAAATATTAACGTTTATAATTTCAGGTGGC

ATCTTTCGATAGGCACCTATTGGTCTTACTGACATCCACTTTGCCTTTCTCTCCACAGGCAG

CCCTGGCGGTCTGGATCACCATCCTCCGCTTCATGGGGGACCTCCCTGAGCCCAAGTACCAC

ACAGCCATGAGTGATGGCAGTGAGAAGATCCCTGTGATGACCAAGATTTATGAGACCCTGGG

CAAGAAGACGTACAAGAGGGAGCTGCAGGCCCTGCAGGGCGAGGGCGAGGCCCAGCTCCCCG

AGGGCCAGAAGAAGAGCAGTGTGAGGCACAAGCTGGTGCATTTGACTCTGAAAAAGAAGTCC

AAGCTCACAGAGGAGGTGACCAAGAGGCTGCATGACGGGGAGTCCACAGTGCAGGGCAACAG

CATGCTGGAGGACCGGCCCACCTCCAACCTGGAGAAGCTGCACTTCATCATCGGCAATGGCA

TCCTGCGGCCAGCACTCCGGGACGAGATCTACTGCCAGATCAGCAAGCAGCTGACCCACAAC

CCCTCCAAGAGCAGCTATGCCCGGGGCTGGATTCTCGTGTCTCTCTGCGTGGGCTGTTTCGC

CCCCTCCGAGAAGTTTGTCAAGTACCTGCGGAACTTCATCCACGGGGGCCCGCCCGGCTACG

CCCCGTACTGTGAGGAGCGCCTGAGAAGGACCTTTGTCAATGGGACACGGACACAGCCGCCC

AGCTGGCTGGAGCTGCAGGCCACCAAGTCCAAGAAGCCAATCATGTTGCCCGTGACATTCAT

GGATGGGACCACCAAGACCCTGCTGACGGACTCGGCAACCACGGCCAAGGAGCTCTGCAACG

CGCTGGCCGACAAGATCTCTCTCAAGGACCGGTTCGGGTTCTCCCTCTACATTGCCCTGTTT

GACAAGGTGTCCTCCCTGGGCAGCGGCAGTGACCACGTCATGGACGCCATCTCCCAGTGCGA

GCAGTACGCCAAGGAGCAGGGCGCCCAGGAGCGCAACGCCCCCTGGAGGCTCTTCTTCCGCA

AAGAGGTCTTCACGCCCTGGCACAGCCCCTCCGAGGACAACGTGGCCACCAACCTCATCTAC

CAGCAGGTGGTGCGAGGAGTCAAGTTTGGGGAGTACAGGTGTGAGAAGGAGGACGACCTGGC

TGAGCTGGCCTCCCAGCAGTACTTTGTAGACTATGGCTCTGAGATGATCCTGGAGCGCCTCC

TGAACCTCGTGCCCACCTACATCCCCGACCGCGAGATCACGCCCCTGAAGACGCTGGAGAAG

TGGGCCCAGCTGGCCATCGCCGCCCACAAGAAGGGGATTTATGCCCAGAGGAGAACTGATGC

CCAGAAGGTCAAAGAGGATGTGGTCAGTTATGCCCGCTTCAAGTGGCCCTTGCTCTTCTCCA

GGTTTTATGAAGCCTACAAATTCTCAGGCCCCAGTCTCCCCAAGAACGACGTCATCGTGGCC

GTCAACTGGACGGGTGTGTACTTTGTGGATGAGCAGGAGCAGGTACTTCTGGAGCTGTCCTT

CCCAGAGATCATGGCCGTGTCCAGCAGCAGGGAGTGCCGTGTCTGGCTCTCACTGGGCTGCT

CTGATCTTGGCTGTGCTGCGCCTCACTCAGGCTGGGCAGGACTGACCCCGGCGGGGCCCTGT

TCTCCGTGTTGGTCCTGCAGGGGAGCGAAAACGACGGCCCCCAGCTTCACGCTGGCCACCAT

CAAGGGGGACGAATACACCTTCACCTCCAGTAATGCTGAGGACATTCGTGACCTGGTGGTCA

CCTTCCTAGAGGGGCTCCGGAAGAGATCTAAGTATGTTGTGGCCCTGCAGGATAACCCCAAC

CCCGCAGGCGAGGAGTCAGGCTTCCTCAGCTTTGCCAAGGGAGACCTCATCATCCTGGACCA

-continued

TGACACGGGCGAGCAGGTCATGAACTCGGGCTGGGCCAACGGCATCAATGAGAGGACCAAGC

AGCGTGGGGACTTCCCCACCGACTGTGTGTACGTCATGCCCACTGTCACCATGCCACCTCGT

GAGATTGTGGCCCTGGTCACCATGACTCCCGATCAGAGGCAGGACGTTGTCCGGCTCTTGCA

GCTGCGAACGGCGGAGCCCGAGGTGCGTGCCAAGCCCTACACGCTGGAGGAGTTTTCCTATG

ACTACTTCAGGCCCCCACCCAAGCACACGCTGAGCCGTGTCATGGTGTCCAAGGCCCGAGGC

AAGGACCGGCTGTGGAGCCACACGCGGGAACCGCTCAAGCAGGCGCTGCTCAAGAAGCTCCT

GGGCAGTGAGGAGCTCTCGCAGGAGGCCTGCCTGGCCTTCATTGCTGTGCTCAAGTACATGG

GCGACTACCCGTCCAAGAGGACACGCTCCGTCAATGAGCTCACCGACCAGATCTTTGAGGGT

CCCCTGAAAGCCGAGCCCCTGAAGGACGAGGCATATGTGCAGATCCTGAAGCAGCTGACCGA

CAACCACATCAGGTACAGCGAGGAGCGGGGTTGGGAGCTGCTCTGGCTGTGCACGGGCCTTT

TCCCACCCAGCAACATCCTCCTGCCCCACGTGCAGCGCTTCCTGCAGTCCCGAAAGCACTGC

CCACTCGCCATCGACTGCCTGCAACGGCTCCAGAAAGCCCTGAGAAACGGGTCCCGGAAGTA

CCCTCCGCACCTGGTGGAGGTGGAGGCCATCCAGCACAAGACCACCCAGATTTTCCACAAGG

TCTACTTCCCTGATGACACTGACGAGGCCTTCGAAGTGGAGTCCAGCACCAAGGCCAAGGAC

TTCTGCCAGAACATCGCCACCAGGCTGCTCCTCAAGTCCTCAGAGGGATTCAGCCTCTTTGT

CAAAATTGCAGACAAGGTCATCAGCGTTCCTGAGAATGACTTCTTCTTTGACTTTGTTCGAC

ACTTGACAGACTGGATAAAGAAAGCTCGGCCCATCAAGGACGGAATTGTGCCCTCACTCACC

TACCAGGTGTTCTTCATGAAGAAGCTGTGGACCACCACGGTGCCAGGGAAGGATCCCATGGC

CGATTCCATCTTCCACTATTACCAGGAGTTGCCCAAGTATCTCCGAGGCTACCACAAGTGCA

CGCGGGAGGAGGTGCTGCAGCTGGGGGCGCTGATCTACAGGGTCAAGTTCGAGGAGGACAAG

TCCTACTTCCCCAGCATCCCCAAGCTGCTGCGGGAGCTGGTGCCCCAGGACCTTATCCGGCA

GGTCTCACCTGATGACTGGAAGCGGTCCATCGTCGCCTACTTCAACAAGCACGCAGGGAAGT

CCAAGGAGGAGGCCAAGCTGGCCTTCCTGAAGCTCATCTTCAAGTGGCCCACCTTTGGCTCA

GCCTTCTTCGAGGTGAAGCAAACTACGGAGCCAAACTTCCCTGAGATCCTCCTAATTGCCAT

CAACAAGTATGGGGTCAGCCTCATCGATCCCAAAACGAAGGATATCCTCACCACTCATCCCT

TCACCAAGATCTCCAACTGGAGCAGCGGCAACACCTACTTCCACATCACCATTGGGAACTTG

GTGCGCGGGAGCAAACTGCTCTGCGAGACGTCACTGGGCTACAAGATGGATGACCTCCTGAC

TTCCTACATTAGCCAGATGCTCACAGCCATGAGCAAACAGCGGGGCTCCAGGAGCGGCAAGT

GACCGCGGCCTGCTGCCGGCTCTGCGGCCTCTTCCGCGTCTTCGAGATCTGCCTCGACTGTG

CCTTCTAGTTGCCAGCCATCTGTTGTTTGCCCCTCCCCCGTGCCTTCCTTGACCCTGGAAGG

TGCCACTCCCACTGTCCTTTCCTAATAAAATGAGGAAATTGCATCGCATTGTCTGAGTAGGT

GTCATTCTATTCTGGGGGGTGGGGTGGGGCAGGACAGCAAGGGGGAGGATTGGGAAGACAAT

AGCAGGCATGCTGGGGACTCGAGTTAAGGGCGCAATTCCCGATTAGGATCTTCCTAGAGCAT

GGCTACGTAGATAAGTAGCATGGCGGGTTAATCATTAACTACAAGGAACCCCTAGTGATGGA

GTTGGCCACTCCCTCTCTGCGCGCTCGCTCGCTCACTGAGGCCGGGCGACCAAAGGTCGCCC

GACGCCCGGGCTTTGCCCGGGCGGCCTCAGTGAGCGAGCGAGCGCGCAG pAAV2.1-CBA-MYO7A_5'TS
Full-sequence (SEQ ID No. 27)

CTGCGCGCTCGCTCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACTCCATCACTAGGG

GTTCCTTGTAGTTAATGATTAACCCGCCATGCTACTTATCTACGTAGCCATGCTCTAGGAAG

-continued

ATCCTAATCGGGAATTCGCCCTTAAGCTAGCGTGCCACCTGGTCGACATTGATTATTGACTA

GTTATTAATAGTAATCAATTACGGGGTCATTAGTTCATAGCCCATATATGGAGTTCCGCGTT

ACATAACTTACGGTAAATGGCCCGCCTGGCTGACCGCCCAACGACCCCCGCCCATTGACGTC

AATAATGACGTATGTTCCCATAGTAACGCCAATAGGGACTTTCCATTGACGTCAATGGGTGG

ACTATTTACGGTAAACTGCCCACTTGGCAGTACATCAAGTGTATCATATGCCAAGTACGCCC

CCTATTGACGTCAATGACGGTAAATGGCCCGCCTGGCATTATGCCCAGTACATGACCTTATG

GGACTTTCCTACTTGGCAGTACATCTACGTATTAGTCATCGCTATTACCATGGTCGAGGTG

AGCCCCACGTTCTGCTTCACTCTCCCCATCTCCCCCCCCTCCCCACCCCCAATTTTGTATTT

ATTTATTTTTTAATTATTTTGTGCAGCGATGGGGGCGGGGGGGGGGGGGGCGCGCGCCAGGC

GGGGCGGGGCGGGGCGAGGGGCGGGGCGGGGCGAGGCGGAGAGGTGCGGCGGCAGCCAATCA

GAGCGGCGCGCTCCGAAAGTTTCCTTTTATGGCGAGGCGGCGGCGGCGGCGGCCCTATAAAA

AGCGAAGCGCGCGGCGGGCGGCTGCAGAAGTTGGTCGTGAGGCACTGGGCAGGTAAGTATCA

AGGTTACAAGACAGGTTTAAGGAGACCAATAGAAACTGGGCTTGTCGAGACAGAGAAGACTC

TTGCGTTTCTGATAGGCACCTATTGGTCTTACTGACATCCACTTTGCCTTTCTCTCCACAGG

TGTCCAGGCGGCCGCCATGGTGATTCTTCAGCAGGGGGACCATGTGTGGATGGACCTGAGAT

TGGGGCAGGAGTTCGACGTGCCCATCGGGGCGGTGGTGAAGCTCTGCGACTCTGGGCAGGTC

CAGGTGGTGGATGATGAAGACAATGAACACTGGATCTCTCCGCAGAACGCAACGCACATCAA

GCCTATGCACCCCACGTCGGTCCACGGCGTGGAGGACATGATCCGCCTGGGGGACCTCAACG

AGGCGGGCATCTTGCGCAACCTGCTTATCCGCTACCGGGACCACCTCATCTACACGTATACG

GGCTCCATCCTGGTGGCTGTGAACCCCTACCAGCTGCTCTCCATCTACTCGCCAGAGCACAT

CCGCCAGTATACCAACAAGAAGATTGGGGAGATGCCCCCCCACATCTTTGCCATTGCTGACA

ACTGCTACTTCAACATGAAACGCAACAGCCGAGACCAGTGCTGCATCATCAGTGGGGAATCT

GGGGCCGGGAAGACGGAGAGCACAAAGCTGATCCTGCAGTTCCTGGCAGCCATCAGTGGGCA

GCACTCGTGGATTGAGCAGCAGGTCTTGGAGGCCACCCCCATTCTGGAAGCATTTGGGAATG

CCAAGACCATCCGCAATGACAACTCAAGCCGTTTCGGAAAGTACATCGACATCCACTTCAAC

AAGCGGGGCGCCATCGAGGGCGCGAAGATTGAGCAGTACCTGCTGGAAAAGTCACGTGTCTG

TCGCCAGGCCCTGGATGAAAGGAACTACCACGTGTTCTACTGCATGCTGGAGGGCATGAGTG

AGGATCAGAAGAAGAAGCTGGGCTTGGGCCAGGCCTCTGACTACAACTACTTGGCCATGGGT

AACTGCATAACCTGTGAGGGCCGGGTGGACAGCCAGGAGTACGCCAACATCCGCTCCGCCAT

GAAGGTGCTCATGTTCACTGACACCGAGAACTGGGAGATCTCGAAGCTCCTGGCTGCCATCC

TGCACCTGGGCAACCTGCAGTATGAGGCACGCACATTTGAAAACCTGGATGCCTGTGAGGTT

CTCTTCTCCCCATCGCTGGCCACAGCTGCATCCCTGCTTGAGGTGAACCCCCCAGACCTGAT

GAGCTGCCTGACTAGCCGCACCCTCATCACCCGCGGGGAGACGGTGTCCACCCCACTGAGCA

GGGAACAGGCACTGGACGTGCGCGACGCCTTCGTAAAGGGGATCTACGGGCGGCTGTTCGTG

TGGATTGTGGACAAGATCAACGCAGCAATTTACAAGCCTCCCTCCCAGGATGTGAAGAACTC

TCGCAGGTCCATCGGCCTCCTGGACATCTTTGGGTTTGAGAACTTTGCTGTGAACAGCTTTG

AGCAGCTCTGCATCAACTTCGCCAATGAGCACCTGCAGCAGTTCTTTGTGCGGCACGTGTTC

AAGCTGGAGCAGGAGGAATATGACCTGGAGAGCATTGACTGGCTGCACATCGAGTTCACTGA

CAACCAGGATGCCCTGGACATGATTGCCAACAAGCCCATGAACATCATCTCCCTCATCGATG

AGGAGAGCAAGTTCCCCAAGGGCACAGACACCACCATGTTACACAAGCTGAACTCCCAGCAC

AAGCTCAACGCCAACTACATCCCCCCCAAGAACAACCATGAGACCCAGTTTGGCATCAACCA

-continued

TTTTGCAGGCATCGTCTACTATGAGACCCAAGGCTTCCTGGAGAAGAACCGAGACACCCTGC

ATGGGGACATTATCCAGCTGGTCCACTCCTCCAGGAACAAGTTCATCAAGCAGATCTTCCAG

GCCGATGTCGCCATGGGCGCCGAGACCAGGAAGCGCTCGCCCACACTTAGCAGCCAGTTCAA

GCGGTCACTGGAGCTGCTGATGCGCACGCTGGGTGCCTGCCAGCCCTTCTTTGTGCGATGCA

TCAAGCCCAATGAGTTCAAGAAGCCCATGCTGTTCGACCGGCACCTGTGCGTGCGCCAGCTG

CGGTACTCAGGAATGATGGAGACCATCCGAATCCGCCGAGCTGGCTACCCCATCCGCTACAG

CTTCGTAGAGTTTGTGGAGCGGTACCGTGTGCTGCTGCCAGGTGTGAAGCCGGCCTACAAGC

AGGGCGACCTCCGCGGGACTTGCCAGCGCATGGCTGAGGCTGTGCTGGGCACCCACGATGAC

TGGCAGATAGGCAAAACCAAGATCTTTCTGAAGGACCACCATGACATGCTGCTGGAAGTGGA

GCGGGACAAAGCCATCACCGACAGAGTCATCCTCCTTCAGAAAGTCATCCGGGGATTCAAAG

ACAGGTCTAACTTTCTGAAGCTGAAGAACGCTGCCACACTGATCCAGAGGCACTGGCGGGGT

CACAACTGTAGGAAGAACTACGGGCTGATGCGTCTGGGCTTCCTGCGGCTGCAGGCCCTGCA

CCGCTCCCGGAAGCTGCACCAGCAGTACCGCCTGGCCCGCCAGCGCATCATCCAGTTCCAGG

CCCGCTGCCGCGCCTATCTGGTGCGCAAGGCCTTCCGCCACCGCCTCTGGGCTGTGCTCACC

GTGCAGGCCTATGCCCGGGGCATGATCGCCCGCAGGCTGCACCAACGCCTCAGGGCTGAGTA

TCTGTGGCGCCTCGAGGCTGAGAAAATGCGGCTGGCGGAGGAAGAGAAGCTTCGGAAGGAGA

TGAGCGCCAAGAAGGCCAAGGAGGAGGCCGAGCGCAAGCATCAGGAGCGCCTGGCCCAGCTG

GCTCGTGAGGACGCTGAGCGGGAGCTGAAGGAGAAGGAGGCCGCTCGGCGGAAGAAGGAGCT

CCTGGAGCAGATGGAAAGGGCCCGCCATGAGCCTGTCAATCACTCAGACATGGTGGACAAGA

TGTTTGGCTTCCTGGGGACTTCAGGTGGCCTGCCAGGCCAGGAGGGCCAGGCACCTAGTGGC

TTTGAGGACCTGGAGCGAGGGCGGAGGGAGATGGTGGAGGAGGACCTGGATGCAGCCCTGCC

CCTGCCTGACGAGGATGAGGAGGACCTCTCTGAGTATAAATTTGCCAAGTTCGCGGCCACCT

ACTTCCAGGGGACAACTACGCACTCCTACACCCGGCGGCCACTCAAACAGCCACTGCTCTAC

CATGACGACGAGGGTGACCAGCTGGTAAGTATCAAGGTTACAAGACAGGTTTAAGGAGACCA

ATAGAAACTGGGCTTGTCGAGACAGAGAAGACTCTTGCGTTTCTCAATTGAAGGGCGAATTC

CGATCTTCCTAGAGCATGGCTACGTAGATAAGTAGCATGGCGGGTTAATCATTAACTACAAG

GAACCCCTAGTGATGGAGTTGGCCACTCCCTCTCTGCGCGCTCGCTCGCTCACTGAGGCCGG

GCGACCAAAGGTCGCCCGACGCCCGGGCTTTGCCCGGGCGGCCTCAGTGAGCGAGCGAGCGC

GCAG pAAV2.1-MYO7A_3'TS_BGH
Full-sequence (SEQ ID No. 28)

CTGCGCGCTCGCTCGCTCACTGAGGCCGCCCGGGCAAAGCCCGGGCGTCGGGCGACCTTTGG

TCGCCCGGCCTCAGTGAGCGAGCGAGCGCGCAGAGAGGGAGTGGCCAACTCCATCACTAGGG

GTTCCTTGTAGTTAATGATTAACCCGCCATGCTACTTATCTACGTAGCCATGCTCTAGGAAG

ATCGGAATTCGATAGGCACCTATTGGTCTTACTGACATCCACTTTGCCTTTCTCTCCACAGG

CAGCCCTGGCGGTCTGGATCACCATCCTCCGCTTCATGGGGGACCTCCCTGAGCCCAAGTAC

CACACAGCCATGAGTGATGGCAGTGAGAAGATCCCTGTGATGACCAAGATTTATGAGACCCT

GGGCAAGAAGACGTACAAGAGGGAGCTGCAGGCCCTGCAGGGCGAGGGCGAGGCCCAGCTCC

CCGAGGGCCAGAAGAAGAGCAGTGTGAGGCACAAGCTGGTGCATTTGACTCTGAAAAAGAAG

TCCAAGCTCACAGAGGAGGTGACCAAGAGGCTGCATGACGGGGAGTCCACAGTGCAGGGCAA

CAGCATGCTGGAGGACCGGCCCACCTCCAACCTGGAGAAGCTGCACTTCATCATCGGCAATG

-continued

GCATCCTGCGGCCAGCACTCCGGGACGAGATCTACTGCCAGATCAGCAAGCAGCTGACCCAC

AACCCCTCCAAGAGCAGCTATGCCCGGGGCTGGATTCTCGTGTCTCTCTGCGTGGGCTGTTT

CGCCCCCTCCGAGAAGTTTGTCAAGTACCTGCGGAACTTCATCCACGGGGGCCCGCCCGGCT

ACGCCCCGTACTGTGAGGAGCGCCTGAGAAGGACCTTTGTCAATGGGACACGGACACAGCCG

CCCAGCTGGCTGGAGCTGCAGGCCACCAAGTCCAAGAAGCCAATCATGTTGCCCGTGACATT

CATGGATGGGACCACCAAGACCCTGCTGACGGACTCGGCAACCACGGCCAAGGAGCTCTGCA

ACGCGCTGGCCGACAAGATCTCTCTCAAGGACCGGTTCGGGTTCTCCCTCTACATTGCCCTG

TTTGACAAGGTGTCCTCCCTGGGCAGCGGCAGTGACCACGTCATGGACGCCATCTCCCAGTG

CGAGCAGTACGCCAAGGAGCAGGGCGCCCAGGAGCGCAACGCCCCCTGGAGGCTCTTCTTCC

GCAAAGAGGTCTTCACGCCCTGGCACAGCCCCTCCGAGGACAACGTGGCCACCAACCTCATC

TACCAGCAGGTGGTGCGAGGAGTCAAGTTTGGGGAGTACAGGTGTGAGAAGGAGGACGACCT

GGCTGAGCTGGCCTCCCAGCAGTACTTTGTAGACTATGGCTCTGAGATGATCCTGGAGCGCC

TCCTGAACCTCGTGCCCACCTACATCCCCGACCGCGAGATCACGCCCCTGAAGACGCTGGAG

AAGTGGGCCCAGCTGGCCATCGCCGCCCACAAGAAGGGGATTTATGCCCAGAGGAGAACTGA

TGCCCAGAAGGTCAAAGAGGATGTGGTCAGTTATGCCCGCTTCAAGTGGCCCTTGCTCTTCT

CCAGGTTTTATGAAGCCTACAAATTCTCAGGCCCCAGTCTCCCCAAGAACGACGTCATCGTG

GCCGTCAACTGGACGGGTGTGTACTTTGTGGATGAGCAGGAGCAGGTACTTCTGGAGCTGTC

CTTCCCAGAGATCATGGCCGTGTCCAGCAGCAGGGAGTGCCGTGTCTGGCTCTCACTGGGCT

GCTCTGATCTTGGCTGTGCTGCGCCTCACTCAGGCTGGGCAGGACTGACCCCGGCGGGGCCC

TGTTCTCCGTGTTGGTCCTGCAGGGGAGCGAAAACGACGGCCCCCAGCTTCACGCTGGCCAC

CATCAAGGGGGACGAATACACCTTCACCTCCAGTAATGCTGAGGACATTCGTGACCTGGTGG

TCACCTTCCTAGAGGGGCTCCGGAAGAGATCTAAGTATGTTGTGGCCCTGCAGGATAACCCC

AACCCCGCAGGCGAGGAGTCAGGCTTCCTCAGCTTTGCCAAGGGAGACCTCATCATCCTGGA

CCATGACACGGGCGAGCAGGTCATGAACTCGGGCTGGGCCAACGGCATCAATGAGAGGACCA

AGCAGCGTGGGGACTTCCCCACCGACTGTGTGTACGTCATGCCCACTGTCACCATGCCACCT

CGTGAGATTGTGGCCCTGGTCACCATGACTCCCGATCAGAGGCAGGACGTTGTCCGGCTCTT

GCAGCTGCGAACGGCGGAGCCCGAGGTGCGTGCCAAGCCCTACACGCTGGAGGAGTTTTCCT

ATGACTACTTCAGGCCCCCACCCAAGCACACGCTGAGCCGTGTCATGGTGTCCAAGGCCCGA

GGCAAGGACCGGCTGTGGAGCCACACGCGGGAACCGCTCAAGCAGGCGCTGCTCAAGAAGCT

CCTGGGCAGTGAGGAGCTCTCGCAGGAGGCCTGCCTGGCCTTCATTGCTGTGCTCAAGTACA

TGGGCGACTACCCGTCCAAGAGGACACGCTCCGTCAATGAGCTCACCGACCAGATCTTTGAG

GGTCCCCTGAAAGCCGAGCCCCTGAAGGACGAGGCATATGTGCAGATCCTGAAGCAGCTGAC

CGACAACCACATCAGGTACAGCGAGGAGCGGGGTTGGGAGCTGCTCTGGCTGTGCACGGGCC

TTTTCCCACCCAGCAACATCCTCCTGCCCCACGTGCAGCGCTTCCTGCAGTCCCGAAAGCAC

TGCCCACTCGCCATCGACTGCCTGCAACGGCTCCAGAAAGCCCTGAGAAACGGGTCCCGGAA

GTACCCTCCGCACCTGGTGGAGGTGGAGGCCATCCAGCACAAGACCACCCAGATTTTCCACA

AGGTCTACTTCCCTGATGACACTGACGAGGCCTTCGAAGTGGAGTCCAGCACCAAGGCCAAG

GACTTCTGCCAGAACATCGCCACCAGGCTGCTCCTCAAGTCCTCAGAGGGATTCAGCCTCTT

TGTCAAAATTGCAGACAAGGTCATCAGCGTTCCTGAGAATGACTTCTTCTTTGACTTTGTTC

GACACTTGACAGACTGGATAAAGAAAGCTCGGCCCATCAAGGACGGAATTGTGCCCTCACTC

-continued

```
ACCTACCAGGTGTTCTTCATGAAGAAGCTGTGGACCACCACGGTGCCAGGGAAGGATCCCAT

GGCCGATTCCATCTTCCACTATTACCAGGAGTTGCCCAAGTATCTCCGAGGCTACCACAAGT

GCACGCGGGAGGAGGTGCTGCAGCTGGGGGCGCTGATCTACAGGGTCAAGTTCGAGGAGGAC

AAGTCCTACTTCCCCAGCATCCCCAAGCTGCTGCGGGAGCTGGTGCCCCAGGACCTTATCCG

GCAGGTCTCACCTGATGACTGGAAGCGGTCCATCGTCGCCTACTTCAACAAGCACGCAGGGA

AGTCCAAGGAGGAGGCCAAGCTGGCCTTCCTGAAGCTCATCTTCAAGTGGCCCACCTTTGGC

TCAGCCTTCTTCGAGGTGAAGCAAACTACGGAGCCAAACTTCCCTGAGATCCTCCTAATTGC

CATCAACAAGTATGGGGTCAGCCTCATCGATCCCAAAACGAAGGATATCCTCACCACTCATC

CCTTCACCAAGATCTCCAACTGGAGCAGCGGCAACACCTACTTCCACATCACCATTGGGAAC

TTGGTGCGCGGGAGCAAACTGCTCTGCGAGACGTCACTGGGCTACAAGATGGATGACCTCCT

GACTTCCTACATTAGCCAGATGCTCACAGCCATGAGCAAACAGCGGGGCTCCAGGAGCGGCA

AGTGACCGCGGCCTGCTGCCGGCTCTGCGGCCTCTTCCGCGTCTTCGAGATCTGCCTCGACT

GTGCCTTCTAGTTGCCAGCCATCTGTTGTTTGCCCCTCCCCCGTGCCTTCCTTGACCCTGGA

AGGTGCCACTCCCACTGTCCTTTCCTAATAAAATGAGGAAATTGCATCGCATTGTCTGAGTA

GGTGTCATTCTATTCTGGGGGGTGGGGTGGGGCAGGACAGCAAGGGGGAGGATTGGGAAGAC

AATAGCAGGCATGCTGGGGACTCGAGTTAAGGGCGCAATTCCCGATTAGGATCTTCCTAGAG

CATGGCTACGTAGATAAGTAGCATGGCGGGTTAATCATTAACTACAAGGAACCCCTAGTGAT

GGAGTTGGCCACTCCCTCTCTGCGCGCTCGCTCGCTCACTGAGGCCGGGCGACCAAAGGTCG

CCCGACGCCCGGGCTTTGCCCGGGCGGCCTCAGTGAGCGAGCGAGCGCGCAG

AP:
                                                          (SEQ ID No. 29)
GTGATCCTAGGTGGAGGCCGAAAGTACATGTTTCGCATGGGAACCCCAGACCCTGAGTACCC

AGATGACTACAGCCAAGGTGGGACCAGGCTGGACGGGAAGAATCTGGTGCAGGAATGGCTGG

CGAAGCGCCAGGGTGCCCGGTACGTGTGGAACCGCACTGAGCTCATGCAGGCTTCCCTGGAC

CCGTCTGTGACCCATCTCATGGGTCTCTTTGAGCCTGGAGACATGAAATACGAGATCCACCG

AGACTCCACACTGGACCCCTCCCTGATGGA

3XFLAG TAG:
                                                          (SEQ ID No. 30)
GACTACAAAGACCATGACGGTGATTATAAAGATCATGACATCGACTACAAGGATGACGATGA

CAAG

HA:
                                                          (SEQ ID No. 31)
ATGTATGATGTTCCTGATTATGCTAGCCTC
```

For the purposes of this invention, a coding sequence of ABCA4, MYO7A and CEP290 which are preferably respectively selected from the sequences herein enclosed, or sequences encoding the same amino acid sequence due to the degeneracy of the genetic code, is functionally linked to a promoter sequence able to regulate the expression thereof in a mammalian retinal cell, particularly in photoreceptor cells. Suitable promoters that can be used according to the invention include the cytomegalovirus promoter, Rhodopsin promoter, Rhodopsin kinase promoter, Interphotoreceptor retinoid binding protein promoter, vitelliform macular dystrophy 2 promoter, fragments and variants thereof retaining a transcription promoter activity.

Viral delivery systems include but are not limited to adenoviral vectors, adeno-associated viral (AAV) vectors, pseudotyped AAV vectors, herpes viral vectors, retroviral vectors, lentiviral vectors, baculoviral vectors. Pseudotyped AAV vectors are those which contain the genome of one AAV serotype in the capsid of a second AAV serotype; for example an AAV2/8 vector contains the AAV8 capsid and the AAV 2 genome (Auricchio et al. (2001) Hum. Mol. Genet. 10(26):3075-81). Such vectors are also known as chimeric vectors. Other examples of delivery systems include ex vivo delivery systems, which include but are not limited to DNA transfection methods such as electroporation, DNA biolistics, lipid-mediated transfection, compacted DNA-mediated transfection.

The construction of an AAV vector can be carried out following procedures and using techniques which are known to a person skilled in the art. The theory and practice for adeno-associated viral vector construction and use in therapy are illustrated in several scientific and patent publications (the following bibliography is herein incorporated by reference: Flotte T R. Adeno-associated virus-based gene therapy for inherited disorders. Pediatr Res. 2005 December; 58(6):1143-7; Goncalves M A. Adeno-associated virus: from defective virus to effective vector, Virol J. 2005 May 6; 2:43; Surace E M, Auricchio A. Adeno-associated viral vectors for retinal gene transfer. Prog Retin Eye Res. 2003 November; 22(6):705-19; Mandel R J, Manfredsson F P, Foust K D, Rising A, Reimsnider S, Nash K, Burger C. Recombinant adeno-associated viral vectors as therapeutic agents to treat neurological disorders. Mol Ther. 2006 March; 13(3):463-83).

Suitable administration forms of a pharmaceutical composition containing AAV vectors include, but are not limited to, injectable solutions or suspensions, eye lotions and ophthalmic ointment. In a preferred embodiment, the AAV vector is administered by subretinal injection, e.g. by injection in the subretinal space, in the anterior chamber or in the retrobulbar space. Preferably the viral vectors are delivered via subretinal approach (as described in Bennicelli J, et al Mol Ther. 2008 Jan. 22; Reversal of Blindness in Animal Models of Leber Congenital Amaurosis Using Optimized AAV2-mediated Gene Transfer).

The doses of virus for use in therapy shall be determined on a case by case basis, depending on the administration route, the severity of the disease, the general conditions of the patients, and other clinical parameters. In general, suitable dosages will vary from $10^8$ to $10^{13}$ vg (vector genomes)/eye.

AAV Vector Production

AAV vectors were produced by the TIGEM AAV Vector Core by triple transfection of HEK293 cells followed by two rounds of CsCl2 purification (54). For each viral preparation, physical titers [genome copies (GC)/ml] were determined by averaging the titer achieved by dot-blot analysis (55) and by PCR quantification using TaqMan (54) (Applied Biosystems, Carlsbad, Calif.).

AAV Infection of HEK293 Cells

HEK293 cells were maintained in Dulbecco's modified Eagle's medium (DMEM) containing 10% fetal bovine serum and 2 mM L-glutamine (GIBCO, Invitrogen S.R.L., Milan, Italy). Cells were plated in six-well plates at a density of $2\times10^6$ cells/well and transfected 16 hours later with 1.3 μg of pDeltaF6 helper plasmid which contains the Ad helper genes (56) using the calcium phosphate method. After 5 hours, cells were washed once with DMEM and incubated with AAV2/2 vectors (m.o.i: $10^5$ GC/cell of each vector; 1:1 co-infection with dual AAV vectors resulted in of $2\times10^5$ total GC/cell) in a final volume of 700 μL serum-free DMEM. Two hours later 2 ml of complete DMEM was added to the cells. Cells were harvested 72 hours following infection for Western blot analysis.

Animal Models

This study was carried out in accordance with the NIH Guide for the Care and Use of Laboratory Animals, the Association for Research in Vision and Ophthalmology Statement for the Use of Animals in Ophthalmic and Vision Research, and the Italian Ministry of Health regulation for animal procedures. Mice were housed at the Institute of Genetics and Biophysics animal house (Naples, Italy) and maintained under a 12-hour light/dark cycle (10-50 lux exposure during the light phase). C57BL/6 and BALB/c mice were purchased from Harlan Italy SRL (Udine, Italy). Albino Abca4−/− mice were generated through successive crosses and backcrosses with BALB/c mice (homozygous for Rpe65 Leu450) (57) and maintained inbred. Breeding was performed crossing homozygous mice. Pigmented sh14626SB/4626SB (referred to as sh1−/−) mice were imported from the Wellcome Trust Sanger Institute (Cambridge, UK, a kind gift of Dr. Karen Steel) and back-crossed twice with CBA/Ca mice purchased from Harlan Italy SRL (Udine, Italy) to obtain heterozygous sh1+/4626SB (referred to as sh1+/−) mice to expand the colony. The mice were maintained intercrossed; breeding was performed crossing heterozygous females with heterozygous males. The pigmented sh1 mice used in this study were either Usher 1B affected (sh1−/−) or unaffected (sh1+/− and sh1+/+). The genotype for the $MYO7A^{4626SB}$ allele was performed by PCR analysis of genomic DNA (extracted from the mouse tail tip) followed by DNA sequencing. The primers used for the PCR amplification are as follows: Fw1 (GTGGAGCTTGACATCTACTTGACC) and Rev3 (AGCTGACCCTCATGACTCTGC), which generate a product of 712 bp that was sequenced with the Fw1 primer. The Large White Female pigs used in this study were registered as purebred in the LWHerd Book of the Italian National Pig Breeders' Association (Azienda Agricola Pasotti, Imola, Italy).

Subretinal Injection of AAV Vectors in Mice and Pigs

Mice (4-5 weeks-old) were anesthetized with an intraperitoneal injection of 2 ml/100 g body weight of avertin [1.25% w/v of 2,2,2-tribromoethanol and 2.5% v/v of 2-methyl-2-butanol (Sigma-Aldrich, Milan, Italy)] (58), then AAV2/8 vectors were delivered subretinally via a trans-scleral transchoroidal approach as described by Liang et al (59). All eyes were treated with 1 μL of vector solution. The AAV2/8 doses (GC/eye) delivered vary across the different mouse experiments as it is described in the "RESULTS" section. AAV2/1-CMV-human Tyrosinase (60) (dose: $2\times10^8$ GC/eye) or AAV2/5-CMV-EGFP (encoding normal size EGFP, dose: $4\times10^8$ GC/eye) was added to the AAV2/8 vector solution that was subretinally delivered to albino (Abca4−/− and BALB/c) (FIG. 6B, 7-8) or pigmented sh1 mice (FIG. 10-11), respectively. This allowed us to mark the RPE within the transduced part of the eyecup, which was subsequently dissected and analyzed. (FIG. 6B, 7-8, 10-11). Subretinal delivery of AAV vectors to the pig retina was performed as previously described (11). All eyes were treated with 100 μL of AAV2/8 vector solution. The AAV2/8 dose was $1\times10^{10}$ (FIG. 3B) or $1\times10^{11}$ GC of each vector/eye (FIGS. 5B and 16) and co-injection of dual AAV vectors resulted in a total dose of $2\times10^{10}$ GC/eye or $2\times10^{11}$ GC/eye, respectively.

Western Blot Analysis

Samples (HEK293 cells, retinas or eyecups) for Western blot analysis were lysed in RIPA buffer (50 mM Tris-Hcl pH 8.0, 150 mM NaCl, 1% NP40, 0.5% Na-Deoxycholate, 1 mM EDTA pH 8.0, 0.1% SDS) to extract EGFP and MYO7A proteins, or in SIE buffer (250 mM sucrose, 3 mM imidazole pH 7.4, 1% ethanol, and 1% NP-40) to extract ABCA4 protein.

Pig samples (the treated areas of the retina as well as whole RPE sheets) were lysed in RIPA buffer to extract MYO7A from RPE sheets, and in SIE buffer to extract MYO7A and ABCA4 from retinas.

Lysis buffers were supplemented with protease inhibitors (Complete Protease inhibitor cocktail tablets, Roche, Milan, Italy) and 1 mM phenylmethylsulfonyl. After lysis EGFP and MYO7A samples were denatured at 99° C. for 5 minutes in 1× Laemli Sample buffer; ABCA4 samples were denatured at 37° C. for 15 minutes in 1× Laemli sample buffer supplemented with 4M urea. Lysates were separated by 7% (ABCA4 and MYO7A samples) or 12% (EGFP samples) SDS-polyacrylamide gel electrophoresis. The antibodies used for immuno-blotting are as follows: anti EGFP (sc-8334, Santa Cruz, Dallas, Tex., USA, 1:500); anti-3×flag (A8592, Sigma-Aldrich, 1:1000); anti-Myo7a (polyclonal, Primm Srl, Milan, Italy, 1:500) generated using a peptide corresponding to aminoacids 941-1070 of the human MYO7A protein; anti-HA antibody (PRB-101P-200, HA.11, Covance, Princeton, N.J., USA, 1:2000); anti-β Tubulin (T5201, Sigma Aldrich, 1:10000); anti-Filamin A (catalog#4762, Cell Signaling Technology, Danvers, Mass., USA, 1:1000); anti-Dysferlin (Dysferlin, clone Ham1/7B6, MONX10795, Tebu-bio, Le Perray-en-Yveline, France, 1:500). The quantification of EGFP, ABCA4 and MYO7A bands detected by Western blot was performed using ImageJ software (free download is available at http://rsbweb.nih.gov/ij/). ABCA4 and MYO7A expression was normalized to Filamin A or Dysferlin for the in vitro and in vivo experiments, respectively. EGFP expression was normalized to β-Tubulin or μg of proteins for in vitro and in vivo experiments, respectively. Different proteins were used for normalization based on the similarity of their molecular weight to those of the different transgene products.

Fundus Photography

The fundus live-imaging was performed by dilating the eye of C57BL/6 with a drop of tropicamide 1% (Visufarma, Rome, Italy) and subsequent eye stimulation with a 300 W flash. Fundus photographs were taken using a Topcon TRC-50IX retinal camera connected to a charge-coupled-device Nikon D1H digital camera (Topcon Medical System, Oakland, N.J., USA).

Histology, Light and Fluorescence Microscopy

To evaluate EGFP expression in histological sections, eyes from C57BL/6 mice or Large White pigs (11) were enucleated one month after AAV2/8 injection. Mouse eyes were fixed in 4% paraformaldehyde over-night and infiltrated with 30% sucrose over-night; the cornea and the lens were then dissected and the eyecups were embedded in optimal cutting temperature compound (O.C.T. matrix, Kaltek, Padua, Italy). Pig eyes were fixed in 4% paraformaldehyde for 48 hours, infiltrated with 10% sucrose for 4 hours, 20% sucrose for 4 hours and finally 30% sucrose overnight. Then, the cornea, the lens, and the vitreous body were dissected and the EGFP-positive portions of the eyecups were embedded in optimal cutting temperature compound (O.C.T. matrix, Kaltek). Serial cryosections (10 μm thick) were cut along the horizontal meridian and progressively distributed on slides. Retinal histology pictures were captured using a Zeiss Axiocam (Carl Zeiss, Oberkochen, Germany). To analyze melanosome localization in the RPE of pigmented sh1 mice, eyes were enucleated 2 months following the AAV injection, fixed in 2% glutaraldehyde-2% paraformaldehyde in 0.1M phosphate buffer over-night, rinsed in 0.1M phosphate buffer, and dissected under a florescence microscope. The EGFP-positive portions of the eyecups were embedded in Araldite 502/EMbed 812 (catalog #13940, Araldite 502/EMbed 812 KIT, Electron Microscopy Sciences, Hatfield, Pa., USA). Semi-thin (0.5-μm) sections were transversally cut on a Leica Ultratome RM2235 (Leica Microsystems, Bannockburn, Ill., USA), mounted on slides, and stained with Epoxy tissue stain (catalog #14950, Electron Microscopy Sciences). Melanosomes were counted by a masked operator analyzing 10 different fields/eye under a light microscope at 100× magnification. Retinal pictures were captured using a Zeiss Axiocam (Carl Zeiss).

Electron Microscopy and Immuno-Gold Labelling

For electron microscopy analyses eyes were harvested from Abca4−/− or sh1 mice at 3 and 2 months after AAV injection, respectively. Eyes were fixed in 0.2% glutaraldehyde-2% paraformaldehyde in 0.1M PHEM buffer pH 6.9 (240 mM PIPES, 100 mM HEPES, 8 mM $MgCl_2$, 40 mM EGTA) for 2 hours and then rinsed in 0.1 M PHEM buffer. Eyes were then dissected under light or fluorescence microscope to select the Tyrosinase- or EGFP-positive portions of the eyecups of albino (Abca4−/− and BALB/c) and pigmented sh1 mice, respectively. The transduced portion of the eyecups were subsequently embedded in 12% gelatin, infused with 2.3M sucrose and frozen in liquid nitrogen. Cryosections (50 nm) were cut using a Leica Ultramicrotome EM FC7 (Leica Microsystems) and extreme care was taken to align PR connecting cilia longitudinally. Measurements of RPE thickness and counts of lipofuscin granules in Abca4−/− eyes were performed by a masked operator (Roman Polishchuk) using the iTEM software (Olympus SYS, Hamburg, Germany). Briefly, RPE thickness was measured in at least 30 different areas along the specimen length using the “Arbitrary Line” tool of iTEM software. The “Touch count” module of the iTEM software was utilized to count the number of lipofuscin granules in the 25 $\mu m^2$ areas distributed randomly across the RPE layer. The granule density was expressed as number of granules per 25 $\mu m^2$. The immuno-gold analysis aimed at testing the expression of ABCA4-HA in Abca4−/− samples after AAV vector delivery was performed by incubating cryosections successively with monoclonal anti-HA antibody (MMS-101P-50, Covance, 1:50), rabbit anti-mouse IgG, and 10-nm gold particle-conjugated protein A. To quantify rhodopsin localization to the connecting cilium of sh1 PR, cryosections of sh1 mice were successively incubated with anti-rhodopsin antibody (1D4, ab5417, Abcam, Cambridge, UK, 1:100), rabbit anti-mouse IgG, and 10-nm gold particle-conjugated protein A. The quantification of gold density of rhodospin in the connecting cilia was performed by a masked operator using iTEM software (Olympus SYS). Briefly, the “Touch count” module of the iTEM software was used to count the number of gold particles per cilium that were normalized to the cilium perimeter (nm) that was measured using the “Closed polygon tool”. Gold density was expressed as gold particles/nm. Immunogold labelled cryosections were analyzed under FEI Tecnai-12 (FEI, Eindhoven, The Netherlands) electron microscope equipped with a Veletta CCD camera for digital image acquisition.

Electrophysiological Analyses

To assess the recovery from light desensitization eyes were stimulated with 3 light flashes of 1 cd s/m2 and then desensitized by exposure to constant light (300 cd/m2) for 3 minutes. Then, eyes were stimulated over time using the pre-desensitization flash (1 cd s/m2) at 0, 5, 15, 30, 45 and 60 minutes post-desensitization. The recovery of rod activity was evaluated by performing the ratio between the b-wave generated post-desensitization (at the different time points) and that generated pre-desensitization. The recovery from light desensitization was evaluated in 2-month-old Abca4−/− mice at 6 weeks post treatment (FIG. 13).

Statistical Analysis

Data are presented as mean±standard error of the mean (s.e.m.). Statistical p values<0.05 were considered significant. One-way ANOVA with post-hoc Multiple Comparison Procedure was used to compare data depicted in: FIG. 2 (p ANOVA: A. 0.0002; B. 0.0015; C. $2\times10^{-7}$); FIG. 8B (p ANOVA: 0.076); FIG. 11B (p ANOVA: 0.5). As lipofuscin granules (FIG. 7B) and melanosomes (FIG. 10B) were counted, counts were analyzed by deviance from a Negative Binomial generalized linear models (61) (FIG. 7B: p value analysis of deviance 0.03794; FIG. 10B: p value analysis of deviance$<<2\times10^{-10}$). The statistically significant differences between groups determined with the post-hoc Multiple Comparison Procedure are marked by asterisks in the Figures.

Results

Generation of Normal Size, Oversize and Dual AAV Vectors.

The inventors generated oversize (OZ), dual AAV trans-splicing (TS), and hybrid vectors that included either the reporter EGFP, the therapeutic ABCA4-3×flag or the MYO7A-HA coding sequences. The inventors also generated dual AAV trans-splicing (TS), and hybrid vectors that included the therapeutic CEP290 tagged at its C-terminus with HA tag. The recombinogenic sequences included in the dual AAV hybrid vectors were based on either a previously reported region of the alkaline phosphatase transgene (AP, dual AAV hybrid AP) (39) or a 77 bp sequence from the F1 phage genome (AK, dual AAV hybrid AK) that the inventors found to be recombinogenic in previous experiments (Colella and Auricchio, unpublished data). The inventors also generated dual AAV overlapping (OV) vectors for ABCA4, MYO7A and CEP290. The inventors did not generate dual AAV OV vectors for EGFP because the efficiency of this approach relies on transgene-specific overlaps for reconstitution (38) and therefore cannot be extrapolated from one gene to another. Instead, for EGFP the inventors generated single AAV vectors of normal size (NS) to compare levels of transgene expression from the various strategies. The constructs generated for production of all AAV vectors used in this study are listed in Table 1 and a schematic representation of the various approaches is depicted in FIG. 1.

The inventors used AAV2/2 vectors for the in vitro experiments, with the ubiquitous cytomegalovirus (CMV) or chicken beta-actin (CBA) promoters, which efficiently transduce HEK293 cells (40). In addition, since the use of heterologous ITRs from AAV serotypes 2 and 5 can increase the productive reassembly of dual AAV vectors (51), the inventors also generated dual AAV AK vectors with heterologous ITRs (FIG. 17*a*) encoding ABCA4 and MYO7A. AAV vectors with heterologous ITRs were packaged in AAV capsids from serotype 2 and tested in vitro.

In the experiments performed in vivo in the retina, The inventors used AAV2/8 vectors, which efficiently transduce RPE and PR (10-12) but poorly infect HEK293 cells, and either the ubiquitous CBA and CMV promoters (11), or the RPE-specific vitelliform macular dystrophy 2 (VMD2) (41) or the PR-specific Rhodopsin (RHO) and Rhodopsin kinase (RHOK) promoters (10) (Table 1).

Dual AAV Vectors Allow High Levels of Transduction In Vitro.

The inventors initially compared the efficiency of the various OZ, dual AAV OV, TS and hybrid AP and AK strategies for AAV-mediated large gene transduction in vitro by infecting HEK293 cells with the AAV2/2 vectors [multiplicity of infection, m.o.i.: $10^5$ genome copies (GC)/cell of each vector] with ubiquitous promoters (CMV for EGFP, ABCA4-3×flag, and CEP290-HA, and CBA for MYO7A-HA).

Cell lysates were analyzed by Western blot with anti-EGFP (FIG. 2A), -3×flag (to detect ABCA4-3×flag, FIG. 2B), -MYO7A (FIG. 2C) and -HA (to detect CEP290-HA) (FIG. 12A) antibodies. Representative Western blots are shown in FIGS. 2A-C and 12A. All strategies resulted in the expression of proteins of the expected size. As predicted, no bands of the expected size were observed when only one of the dual AAV vectors was used for infection (FIGS. 2A-C and 12A). Quantification of transgene expression (FIG. 2D-F) showed that the dual AAV hybrid AP approach resulted in the lowest levels of transgene expression, while the dual AAV OV, TS and hybrid AK approaches were more efficient than the AAV OZ approach. Dual AAV TS and hybrid AK approaches confirmed their ability to efficiently express large genes also in the case of CEP290 (FIG. 12B). In addition, the use of dual AAV AK vectors with heterologous ITRs resulted in expression of full-length ABCA4 and MYO7A proteins in vitro (FIG. 17).

Dual AAV TS and Hybrid AK but not OV Vectors Transduce Mouse and Pig Photoreceptors.

The inventors then evaluated each of the AAV-based systems for large gene transduction in the mouse retina. To test the dual AAV OV, which was transgene-specific, The inventors used the therapeutic ABCA4 and MYO7A genes (FIG. 3). The inventors used EGFP to evaluate the AAV OZ and the dual AAV TS, hybrid AP and AK approaches (FIG. 4). Western blot analysis on retinal lysates, one month after subretinal delivery in C57BL/6 mice of the dual AAV OV vectors (dose of each vector/eye: $1.3\times10^9$ GC), encoding ABCA4-3×flag from the ubiquitous CMV promoter, revealed robust protein expression (FIG. 3A). To determine which cell type in the retina expressed ABCA4, The inventors used dual AAV OV vectors that contained either the PR-specific RHO and RHOK, or the RPE-specific VMD2 (dose of each vector/eye: $1\times10^9$ GC) promoters. The inventors detected ABCA4 protein expression in retinas injected with the VMD2 but not in those containing the RHO and RHOK promoters (FIG. 3A). These results were also confirmed in the Large White pig retina. The pig retina is an excellent model to evaluate vector efficiency because of its size, which is similar to the human retina, and because it is enriched with cones that are concentrated in a streak-like region whose cone density is comparable to that of the primate macula (11). The inventors injected Large White pig subretinally with dual AAV OV vectors encoding ABCA4-3×flag (dose of each vector/eye: $1\times10^{10}$ GC), and observed ABCA4 protein expression with the CMV but not the RHO promoter (FIG. 3B). Similarly, subretinal administration of dual AAV OV vectors encoding MYO7A-HA resulted in weak MYO7A protein expression in the mouse retina with the ubiquitous CBA (dose of each vector/eye: $2.5\times10^9$ GC) and no detectable expression with the RHO (dose of each vector/eye: $3.2\times10^9$ GC) promoter (FIG. 3C). Overall, these data suggested that the dual AAV OV approach was more efficient for large gene transfer to RPE than to PR, which are a major target of gene therapy for IRDs, such as STGD and USH1B.

To find an AAV-based strategy that efficiently transduces large genes in PR, the inventors evaluated the retinal transduction properties of the AAV OZ and dual AAV TS, hybrid AP, and AK approaches. The inventors initially used EGFP, which allowed us to easily localize transgene expression in the various retinal cell types including PR as well as to properly compare the levels of AAV-based large transgene transduction to those of a single AAV NS vector. C57BL/6 mice were subretinally injected with AAV NS, OZ and dual AAV TS, and hybrid AP and AK vectors (dose of each vector/eye: $1.7\times10^9$ GC), all encoding EGFP under the transcriptional control of the CMV promoter. One month later, fundus photographs showed that the highest levels of fluorescence were obtained with the AAV NS, and dual AAV TS and hybrid AK approaches (FIG. 15). Fluorescence microscope analysis of retinal cryosections showed that detectable levels of RPE or PR transduction could be observed in: 77% (10/13) retinas injected with AAV NS and OZ vectors; 92% (12/13) retinas injected with dual AAV TS, hybrid AP and AK vectors. FIG. 4 shows the best transduced retinas from each of these groups. The most robust levels of PR transduction were obtained with the AAV NS and dual AAV TS and hybrid AK approaches.

The inventors then assessed PR-specific transduction levels in C57BL/6 mice following subretinal administration of dual AAV TS and hybrid AK vectors, which appears the most promising for large gene reconstitution in PR, as well as AAV NS vectors for comparison (dose of each vector/eye: $2.4\times10^9$ GC). All vectors encoded EGFP under the transcriptional control of the PR-specific RHO promoter. One month after vector administration retinas were cryosectioned and analyzed under a fluorescence microscope (FIG. 5A). All approaches resulted in high levels of PR transduction, which seemed more consistent with the single AAV NS vector. The inventors found PR transduction in: 100% (6/6) of the retinas injected with AAV NS; 60% (9/15) of the retinas injected with dual AAV TS; 71% (10/14) of the retinas injected with dual AAV hybrid AK. FIG. 5A shows the best transduced retinas from each of these groups. Thus, the inventors conclude that dual AAV TS and hybrid AK strategies allow efficient mouse PR transduction although at levels which are lower than those obtained with a NS AAV. The inventors then confirmed that subretinal administration of dual AAV TS and hybrid AK vectors (dose of each vector/eye: $1\times10^{11}$ GC; EGFP-positive retinas out of total injected: 2/2 dual AAV TS; 2/2 dual AAV hybrid AK) transduced PR of White Large pigs (FIG. 5B).

In addition, subretinal delivery to the pig retina of dual AAV TS and hybrid AK vectors (dose of each vector/eye: $1\times10^{11}$) resulted in efficient expression of both full-length ABCA4-3×flag specifically in PRs (FIG. 16*a*) and full-length MYO7A-HA in RPE and PRs (FIG. 16*b*) Interestingly, dual AAV hybrid AK vectors resulted in more consistent expression of the large ABCA4 and MYO7A proteins in PRs, compared with dual AAV TS vectors (FIG. 16).

Dual AAV Vectors Improve the Retinal Phenotype of STGD and USH1B Mouse Models.

To understand whether the levels of PR transduction obtained with the dual AAV TS and hybrid AK approaches may be therapeutically relevant, the inventors investigated them in the retina of two mouse models of IRDs, STGD and USH1B caused by mutations in the large ABCA4 and MYO7A genes, respectively.

Although the Abca4−/− mouse model does not undergo severe PR degeneration (42), the absence of the ABCA4-encoded all-trans retinal transporter in PR outer segments (43-44) causes an accumulation of lipofuscin in PR as well as in RPE, as result of PR phagocytosis by RPE (45). As a consequence, both the number of lipofuscin granules in the RPE and the thickness of RPE cells are greater in Abca4−/− mice than in control mice (45). Moreover the Abca4−/− mouse model is characterized by delayed dark adaptation (57, 62). Since ABCA4 is expressed specifically in PR, the inventors generated dual AAV TS and hybrid AK vectors encoding ABCA4-3×flag under the transcriptional control of the RHO promoter. These vectors were subretinally injected in wild-type C57BL/6 mice (dose of each vector/eye: $3\text{-}5\times10^9$ GC) and one month later retinas were lysed and analyzed by Western blot with anti-3×flag antibodies. Both approaches resulted in robust yet variable levels of ABCA4-3×flag expression. ABCA4-3×flag expression levels were more consistent in retina treated with the dual AAV hybrid AK vectors (FIG. 6A). These results were confirmed in Large White pigs (data not shown). In addition, one month-old albino Abca4−/− mice were injected subretinally with the dual AAV hybrid AK RHO-ABCA4-HA vectors (dose of each vector/eye: $1\text{-}3\times10^9$ GC). Three months later, eyes were harvested and immuno-electron microscopy analysis with anti-hemagglutinin (HA) antibodies of retinal sections confirmed that immunogold particles were correctly localized in PR outer segments only in animals that were injected with the combination of 5' and 3' dual AAV hybrid AK vectors (FIG. 6B). To assess the functionality of the ABCA4 protein expressed by the dual vectors, the inventors also performed transmission electron microscopy to assess the presence and number of RPE lipofuscin granules (FIG. 7) and RPE thickness (FIG. 8). Both were greater in the retina of Abca4−/− mice injected with control vectors than in the retina of wild-type, age-matched Balb/C controls, and were reduced or normalized in the eyes injected with the therapeutic dual AAV TS or hybrid AK vectors (FIGS. 7B and 8B). In addition, the ability of Abca4−/− photoreceptors to recover from light desensitization was significantly improved in the retinas treated with the therapeutic vectors when compared to control retinas (FIG. 13).

The inventors then tested PR transduction levels and efficacy of dual AAV-mediated MYO7A gene transfer in the retina of sh1 mice, the most commonly used model of USH1B (23-24, 46-48). In sh1 mice, a deficiency in the motor Myo7a causes the mis-localization of RPE melanosomes (47), which do not enter into the RPE microvilli, and the accumulation of rhodopsin at the PR connecting cilium (48). Since MYO7A is expressed in both RPE and PR (22-23), the inventors then used dual AAV TS and hybrid AK vectors expressing MYO7A-HA under the transcriptional control of the ubiquitous CBA promoter. One month-old wild-type C57BL/6 mice were injected with the dual AAV vectors (dose of each vector/eye: $1.7\times10^9$ GC) and eyecup lysates were evaluated one month later using Western blot analysis with anti-HA antibodies. Results showed similarly robust and consistent levels of MYO7A expression in retinas treated with both approaches (FIG. 9). Taking advantage of our anti-MYO7A antibody able to recognize both murine and human MYO7A, we compared the levels of MYO7A achieved following delivery of dual AAV vectors to the sh1−/− eye to those expressed endogenously in the sh1+/+ eye (FIG. 14). We used both the CBA (FIG. 14, left panel, dose of each vector/eye: $1\text{-}6\times10^9$GC) and the RHO promoters (FIG. 14, right panel, dose of each vector/eye: $2\times10^9$GC) to distinguish MYO7A expression achieved in both PR and RPE from that in PR alone: the former is about 20% (FIG. 14, left panel) and the latter up to about 50% of endogenous Myo7a (FIG. 14, right panel). Our analysis additionally shows that the levels of MYO7A expression achieved in PR by dual AAV hybrid AK are higher than those obtained with the dual AAV TS vectors despite the number of transduced retinas is similar (TS-MYO7A: 3 retinas positive out of 8 injected; AK-MYO7A: 4 retinas positive out of 8 treated; FIG. 14, right panel).

To test the ability of MYO7A expressed from dual AAV vectors to rescue the defects of the sh1−/− retina, the inventors then subretinally injected the CBA sets of dual AAV TS and hybrid AK vectors (dose of each vector/eye: $2.5\times10^9$ GC) in one month-old sh1 mice. The inventors assessed RPE melanosome (FIG. 10) and rhodopsin localization (FIG. 11) by analysis of semi-thin retinal section and by immuno-electron microscopy, respectively. Unlike unaffected sh1+/−, the sh1−/− melanosomes do not enter the RPE microvilli after delivery of control vectors (each single 5' half of the dual-AAV strategies, FIG. 10). The number of RPE melanosomes correctly localized apically was significantly improved after the delivery of either dual AAV TS or hybrid AK vectors encoding MYO7A (FIG. 10B). Remarkably, the inventors also found that the MYO7A expression mediated by dual AAV TS and hybrid AK vectors reduced the accumulation of rhodopsin at the connecting cilium of sh1−/− PR (FIG. 11).

Discussion

While AAV-mediated gene therapy is effective in animal models and in patients with inherited blinding conditions (5-9, 49), its application to diseases affecting the retina and requiring a transfer of genes larger than 5 kb (referred to as large genes) is inhibited by AAV limited cargo capacity. To overcome this, the inventors compared the efficiency of various AAV-based strategies for large gene transduction including: AAV OZ and dual AAV OV, TS and hybrid approaches in vitro and in mouse and pig retina. In previous experiments, inventors selected a 77 bp sequence from the F1 phage genome that the inventors identified for its recombinogenic properties and used in the dual hybrid approach (AK, dual AAV hybrid AK).

The inventors' in vitro and in vivo results show that the dual AAV hybrid AK surprisingly outperforms the dual AAV hybrid AP and that all dual AAV strategies the inventors tested (with the exception of the dual AAV hybrid AP) outperform AAV OZ vectors in terms of transduction levels. This may be explained by the homogenous size of the dual AAV genome population when compared to OZ genomes, which may favor the generation of transcriptionally active large transgene expression cassettes.

The dual AAV OV approach seems particularly interesting when compared to the TS or hybrid AK approaches as dual AAV OV vectors only contain sequences belonging to the therapeutic transgene expression cassette. However, when the inventors administered dual AAV OV vectors to the subretinal space of adult mice and pigs, the inventors were only able to detect expression of the large ABCA4 protein when the ubiquitous or the RPE-specific promoters, but not the PR-specific promoters, were used. This may suggest that the homologous recombination required for dual AAV OV reconstitution is more efficient in RPE than PR. This is consistent with the low levels of homologous recombination reported in post-mitotic neurons (50) and may partially explain the lack of dual AAV OV-mediated MYO7A transduction recently reported by other groups (30). The inventors conclude that subretinal administration of dual AAV OV vectors should not be used for large gene transfer to PR, although the inventors cannot exclude that sequences that are more recombinogenic than those included in the inventors' dual AAV OV ABCA4 and MYO7A vectors may allow efficient homologous recombination in PR.

Dual AAV TS and hybrid AK approaches efficiently transduce mouse and pig PR, differently from what the inventors observed with dual AAV OV. This is consistent with the knowledge that the mechanism of large gene reconstitution mediated by dual AAV TS and hybrid AK approaches may be via ITR-mediated head-to-tail rejoining (32, 35, 51) rather than homologous recombination.

The levels of mouse PR transduction the inventors achieved with dual AAV TS and hybrid AK is lower and less consistent than with single NS vectors. However, dual AAV may be effective for treating inherited blinding conditions that require relatively low levels of transgene expression, i.e. diseases inherited as autosomal recessive. Indeed, the inventors show that subretinal delivery of dual AAV TS and hybrid AK improves and even normalizes the retinal defects of two animal models of inherited retinal diseases, STGD and USH1B, which are due to mutations in large genes and are attractive targets of gene therapy.

The genome size of dual AAV vectors is homogenous, which means identity and safety issues related to their use should be less considerable than those related to AAV OZ vectors, which have heterogeneous genome sizes. In contrast, the inventors detected neither ERG or retinal histological abnormalities in the mice that the inventors followed up to 1-2 months after dual AAV vector delivery (data not shown).

In conclusion, the inventors identified a new recombinogenic sequence (AK) that strikingly improves the performance of the AAV dual hybrid vector system. In fact they found that dual AAV vectors are efficient both in vitro and in the retina in vivo. While dual AAV OV vectors efficiently transduce RPE, they do not transduce PR, whereas dual AAV TS and hybrid AK approaches drive efficient large gene reconstitution in both cell types. Administration of dual AAV TS and hybrid AK approaches improved the retinal phenotype of mouse models of STGD and USH1B, providing evidence of the efficacy of these strategies for gene therapy for these and other blinding conditions, which require large gene transfer to retinal PR as well as RPE. These findings will greatly broaden the application of AAV vectors for gene therapies not only to eyes, but also to muscle as well as to other organs and tissues. Diseases other than IRD caused by defective genes larger than 5 kb include non-limiting examples of muscular dystrophies, dysferlin deficiencies (limb-girdle muscular dystrophy type 2B and Miyoshi myopathy), Cystic Fibrosis, Hemophilia.

REFERENCES

1. M. M. Sohocki, et al. *Hum. Mutat.* 17, 42-51 (2001).
2. T. Dryja, in *The Online Metabolic & Molecular Bases of Inherited Diseases* C. Scriver, A. Beaudet, W. Sly, D. Valle, Eds. (McGraw-Hill, New York, N.Y., 2001), vol 4, pp. 5903-5933.
3. P. Colella, et al. *Trends Mol. Med.* 15, 23-31 (2009).
4. L. H. Vandenberghe, A. Auricchio, *Gene Ther.* 19, 162-168 (2012).
5. J. W. Bainbridge, et al. *N. Engl. J. Med.* 358, 2231-2239 (2008).
6. A. V. Cideciyan, et al. *N. Engl. J. Med.* 361, 725-727 (2009).
7. A. M. Maguire, et al. *N. Engl. J. Med.* 358, 2240-2248 (2008).
8. A. M. Maguire, et al. *Lancet* 374, 1597-1605 (2009).
9. F. Simonelli, et al. *Mol. Ther.* 18, 643-650 (2010).
10. M. Allocca, et al. *J. Virol.* 81, 11372-11380 (2007).
11. C. Mussolino, et al. *Gene Ther.* 18, 637-645 (2011).
12. L. H. Vandenberghe, et al. *Sci. Transl. Med.* 3, 88ra54 (2011).
13. A. Auricchio, *Hum. Gene Ther.* 22, 1169-1170 (2011).
14. M. Natkunarajah, et al. *Gene Ther.* 15, 463-467 (2008).
15. B. Dong, et al. *Mol. Ther.* 18, 87-92 (2010).
16. Y. Lai, et al. *Mol. Ther.* 18, 75-79 (2010).
17. Z. Wu, et al. *Mol. Ther.* 18, 80-86 (2010).
18. Y. Wang, et al. *Hum. Gene Ther. Methods* 23, 225-233 (2012).
19. P. L. Hermonat, et al. *FEBS Lett.* 407, 78-84 (1997).
20. R. Allikmets, *Nat. Genet.* 17, 122 (1997).
21. J. M. Millan, et al. *J. Ophthalmol.* 2011, 417217 (2011).
22. T. Hasson, et al. *Proc. Natl. Acad. Sci. USA* 92, 9815-9819 (1995).
23. X. Liu, et al. *Cell. Motif. Cytoskeleton* 37, 240-252 (1997).
24. D. Gibbs, et al. *Invest. Ophthalmol. Vis. Sci.* 51, 1130-1135 (2010).

25. J. C. Grieger, et al. *J. Virol.* 79, 9933-9944 (2005).
26. J. Wu, et al. *Hum. Gene Ther.* 18, 171-182 (2007).
27. M. Allocca, et al. *J. Clin. Invest.* 118, 1955-1964 (2008).
28. P. E. Monahan, et al. *Mol. Ther.* 18, 1907-1916 (2010).
29. W. E. Grose, et al. *PLoS One* 7, e39233 (2012).
30. V. S. Lopes, et al. *Gene Ther*. (2013).
31. M. L. Hirsch, et al. *Mol. Ther.* 18, 6-8 (2010).
32. D. Duan, et al. *J. Virol.* 72, 8568-8577 (1998).
33. Z. Yan, et al. *Proc. Natl. Acad. Sci. USA* 97, 6716-6721 (2000).
34. D. Duan, et al. *Mol. Ther.* 4, 383-391 (2001).
35. A. Ghosh, et al. *Mol. Ther.* 16, 124-130 (2008).
36. Y. Lai, et al. *Nat. Biotechnol.* 23, 1435-1439 (2005).
37. S. J. Reich, et al. *Hum. Gene. Ther.* 14, 37-44 (2003).
38. A. Ghosh, et al. *J. Gene Med.* 8, 298-305 (2006).
39. A. Ghosh, et al. *Hum. Gene Ther.* 22, 77-83 (2011).
40. X. Dong, et al. *PLoS One* 5, e13479 (2010).
41. N. Esumi, et al. *J. Biol. Chem.* 279, 19064-19073 (2004).
42. L. Wu, et al. *Adv. Exp. Med. Biol.* 664, 533-539 (2010).
43. M. Illing, et al. *J. Biol. Chem.* 272, 10303-10310 (1997).
44. H. Sun, et al. *Nat. Genet.* 17, 15-16 (1997).
45. N. L. Mata, et al. *Invest. Ophthalmol. Vis. Sci.* 42, 1685-1690 (2001).
46. C. Lillo, et al. *Adv. Exp. Med. Biol.* 533, 143-150 (2003).
47. X. Liu, et al. *Nat. Genet.* 19, 117-118 (1998).
48. X. Liu, et al. *J. Neurosci.* 19, 6267-6274 (1999).
49. S. G. Jacobson, et al. *Mol. Ther.* 13, 1074-1084 (2006).
50. M. L. Fishel, et al. *Mutat. Res.* 614, 24-36 (2007).
51. Z. Yan, et al. *J. Virol.* 79, 364-379 (2005).
52. G. Gao, et al. *Hum. Gene Ther.* 11, 2079-2091 (2000).
53. A. Auricchio, et al. *Hum. Gene Ther.* 12, 71-76 (2001).
54. C. Mueller, et al. *Curr. Protoc. Microbiol. Chapter* 14, Unit 14D 11 (2012).
55. L. Drittanti, et al. *Gene Ther.* 7, 924-929 (2000).
56. Y. Zhang, et al. *J. Virol.* 74, 8003-8010 (2000).
57. R. A. Radu, et al. *Proc. Natl. Acad. Sci. USA* 101, 5928-5933 (2004).
58. V. E. Papaioannou, J. G. Fox, *Lab. Anim. Sci.* 43, 189-192 (1993).
59. F. Q. Liang, et al. in *Methods in Molecular Medicine: Vision Research Protocols*, P. E. Rakoczy, Ed. (Humana Press Inc, Totowa, N.J., 2000), vol. 47, pp. 125-139.
60. A. Gargiulo, et al. *Mol. Ther.* 17, 1347-1354 (2009).
61. V. N. Venables, B. D. Ripley, Modern Applied Statistics with S, S. J. Chambers, W. Eddy, W. Hardle, Sheater S, L. Tierney, Eds., (Springer Science+Business Media, New York, USA, 2002). [fourth edition].
Weng, J., et al. I *Cell* 98, 13-23 (1999).

The invention claimed is:

1. A dual construct system to express the coding sequence of a gene of interest in a host cell, said coding sequence consisting of a 5'end portion and of a 3'end portion, said dual construct system comprising:

a) a first plasmid comprising, in a 5'-3' direction:
 a 5'-inverted terminal repeat (5'-ITR) sequence;
 a promoter sequence;
 the 5' end portion of said coding sequence, said 5'end portion being operably linked to and under control of said promoter;
a nucleic acid sequence of a splicing donor signal; and
a 3'-inverted terminal repeat (3'-ITR) sequence; and
b) a second plasmid comprising, in a 5'-3' direction:
 a 5'-inverted terminal repeat (5'-ITR) sequence;
 a nucleic acid sequence of a splicing acceptor signal;
 the 3'end of said coding sequence;
 a poly-adenylation signal nucleic acid sequence;
 a 3'-inverted terminal repeat (3'-ITR) sequence;
wherein the nucleotide sequence of the respective ITRs is obtained from an adeno-associated virus (AAV) of the same AAV serotype or from an AAV of a different serotype;
wherein said first plasmid further comprises a nucleic acid sequence of a recombinogenic region in 5' position of the 3'ITR of said first plasmid, and wherein said second plasmid further comprises a nucleic acid sequence of a recombinogenic region in 3' position of the 5'-ITR of said second plasmid; and
wherein the recombinogenic region is an F1 phage recombinogenic region that consists of the sequence:

```
                                                   (SEQ ID NO: 3)
GGGATTTTGCCGATTTCGGCCTATTGGTTAAAAAATGAGCTGATTTAACA

AAAATTTAACGCGAATTTTAACAAAAT.
```

2. The dual construct system according to claim 1, wherein upon introduction of said first plasmid and said second plasmid into the host cell, said coding sequence reconstitutes by means of the splicing donor and the splicing acceptor signals.

3. The dual construct system according to claim 1, wherein the 3'-ITR of the first plasmid and the 5'-ITR of the second plasmid are from the same AAV serotype.

4. The dual construct system according to claim 1, wherein the 5'-ITR and 3'-ITR of the first plasmid and the 5'-ITR and 3'-ITR of the second plasmid are respectively from different AAV serotypes.

5. The dual construct system according to claim 1, wherein the 5'-ITR of the first plasmid and the 3'-ITR of the second plasmid are from different AAV serotypes.

6. The dual construct system according to claim 1, wherein the coding sequence is split into the 5' end portion and the 3' end portion at a natural exon-exon junction.

7. The dual construct system according to claim 1, wherein the nucleic acid sequence of the splicing donor signal comprises the sequence:

```
                                                   (SEQ ID NO: 1)
GTAAGTATCAAGGTTACAAGACAGGTTTAAGGAGACCAATAGAAACTGGG

CTTGTCGAGACAGAGAAGACTCTTGCGTTTCT.
```

8. The dual construct system according to claim 1, wherein the nucleic acid sequence of the splicing acceptor signal comprises the sequence

```
                                                   (SEQ ID NO: 2)
GATAGGCACCTATTGGTCTTACTGACATCCACTTTGCCTTTCTCTCCACA

G.
```

9. The dual construct system according to claim 1, wherein the first plasmid further comprises at least one enhancer sequence, operably linked to the coding sequence.

10. The dual construct system according to claim 1, wherein the coding sequence is a nucleotide sequence encoding a protein able to correct an inherited retinal degeneration.

11. The dual construct system according to claim 10, wherein the coding sequence is selected from the group consisting of: ABCA4, MYO7A, CEP290, CDH23, EYS, USH2a, GPR98 and ALMS1.

12. A dual viral vector system comprising:
a) a first viral vector containing the first plasmid, and
b) a second viral vector containing the second plasmid,
wherein said first and said second plasmids are as defined in claim 1, and
wherein the vectors are adeno-associated virus (AAV) vectors.

13. The dual viral vector system according to claim 12, wherein the adeno-associated virus (AAV) vectors are the same or different AAV serotypes.

14. The dual viral vector system according to claim 12, wherein the AAV vectors have a serotype selected from the group consisting of serotype 2, serotype 8, serotype 5, serotype 7 and serotype 9.

15. An isolated host cell transformed with the dual viral vector system according to claim 12.

16. A pharmaceutical composition comprising the dual construct system according to claim 1, and a pharmaceutically acceptable vehicle.

17. A method for treating a subject having a disease characterized by a retinal degeneration comprising subretinally administering to said subject an effective amount of the dual viral vector system according to claim 12.

18. A pharmaceutical composition comprising the dual viral vector system according to claim 12 and a pharmaceutically acceptable vehicle.

19. A pharmaceutical composition comprising the isolated host cell according to claim 15 and a pharmaceutically acceptable vehicle.

* * * * *